(12) United States Patent
Brittain et al.

(10) Patent No.: US 6,344,570 B1
(45) Date of Patent: Feb. 5, 2002

(54) SUBSTITUTED UREA DERIVATIVES AS CELL ADHESION INHIBITORS

(75) Inventors: David R Brittain; Craig Johnstone, both of Macclesfield (GB)

(73) Assignee: AstraZeneca UK Limited, London (GB)

(*) Notice: Subject to any disclaimer, the term of this patent is extended or adjusted under 35 U.S.C. 154(b) by 0 days.

(21) Appl. No.: 09/554,224
(22) PCT Filed: Nov. 9, 1998
(86) PCT No.: PCT/GB98/03334
§ 371 Date: Jul. 11, 2000
§ 102(e) Date: Jul. 11, 2000
(87) PCT Pub. No.: WO99/24398
PCT Pub. Date: May 20, 1999

(30) Foreign Application Priority Data

Nov. 12, 1997 (GB) ............................................. 9723789

(51) Int. Cl.$^7$ ..................... C07D 317/48; A61K 31/36
(52) U.S. Cl. ..................... 549/441; 514/307; 514/338; 514/363; 514/393; 514/394; 514/419; 514/464; 514/465; 514/533; 514/535; 546/146; 546/284.1; 548/140; 548/305.1; 548/454; 560/9; 560/12; 560/42; 564/133
(58) Field of Search ..................... 514/307, 338, 514/363, 393, 394, 419, 464, 465, 533, 535; 564/133; 546/146, 284.1; 548/140, 305.1, 454; 549/441; 560/9, 12, 42

(56) References Cited

FOREIGN PATENT DOCUMENTS

| WO | WO96/22966 A | 8/1996 |
|---|---|---|
| WO | WO 97/03094 | 1/1997 |
| WO | WO97/08145 A | 3/1997 |
| WO | WO 98/04247 | 5/1998 |
| WO | WO 98/04913 | 5/1998 |

Primary Examiner—Shailendra Kumar
(74) Attorney, Agent, or Firm—Pillsbury Winthrop LLP

(57) ABSTRACT

Compounds of formula (II)

(II)

where $R^1$ is in the para or meta position and is (A); $R^2$ and $R^3$ are each independently selected from hydrogen, nitro, $C_{1-6}$alkyl, $C_{3-6}$cycloalkyl, $C_{2-6}$alkenyl, $C_{2-6}$alkynyl, $C_{1-4}$alkoxyl, $C_{1-6}$alkylamino, $C_{1-6}$dialkylamino, $C_{1-6}$akylC$_{1-4}$alkoxyl, $C_{1-6}$alkylaminoC$_{1-6}$alkyl, amino, cyano, halogeno, trifluoromethyl, —CO$_2$R$^{12}$ and —CONR$^{12}$R$^{13}$, where $R^{12}$ and $R^{13}$ are independently selected from hydrogen or $C_{1-6}$alkyl, or $R^2$ and $R^3$ together with the phenyl to which they are attached form a 9 or 10 membered bicyclic ring system; $R^4$ is $C_{1-4}$alkyl; $R^5$ is selected from hydrogen and $C_{1-4}$alkyl; $R^6$ is selected from $C_{1-6}$alkyl, $C_{1-4}$alkyl(C$_{4-6}$)cycloalkyl, $C_{1-6}$alkyl(C$_{1-6}$)alkoxyl, $C_{1-6}$alkylS(C$_{1-6}$)alkyl, $C_{1-4}$alkylsulphonyl(C$_{1-4}$)alkyl; (B) where q is an integer from 1 to 6 and $R^{14}$ is halogeno; $R^7$ is selected from $C_{1-6}$alkyl, $C_{1-8}$alkoxylcarbonyl, $C_{2-6}$alkenyl, 1,3-benzodioxol-5-yl and aryl each optionally substituted by one or more substituents selected from $C_{1-4}$alkoxy, $C_{1-6}$alkyl, cyano, halogeno, and trifluoromethyl; $R^8$ is aryl, heteroaryl, a bicyclic heteroaryl ring system linked to the nitrogen via a ring carbon or a 9 or 10 membered bicyclic ring system linked to the nitrogen via a ring carbon and each ring is optionally substituted with up to two substituents, which may be the same or different, and are selected from $C_{1-6}$alkyl, $C_{1-4}$alkoxy, $C_{1-4}$alkylthio, $C_{1-6}$alkylC$_{1-4}$alkoxyl, $C_{1-6}$alkylaminoC$_{1-6}$alkyl, hydroxy, —CO$_2$H, —(CH$_2$)$_p$OH where p is 1 or 2, cyano, halogeno, and trifluoromethyl; $R^9$ and $R^{10}$ are each independently selected from hydrogen and $C_{1-4}$alkyl or $R^8$ and $R^9$ together with the nitrogen to which they are attached form a dihydroindolyl, or a dihidroquinolinyl group; $R^{11}$ is selected from carboxyl, tetrazolyl, alkyl sulphonylcarbamyl, sulfo and sulfino; Y is oxygen, sulphur or sulfonyl; m is 0 or 1; and n is 0 or an integer from 1 to 4 with the proviso that when m and n cannot both be 0 and when m is 1, n is 0; or a pharmaceutically acceptable salt or in vivo hydrolyzable ester thereof. The compounds inhibit the interaction of vascular cell-adhesion molecule-1 and fibronectin with integrin very late antigen 4 ($\alpha_4\beta_1$). They have therapeutic applications such as in multiple sclerosis, rheumatoid arthritis, asthma, coronary artery disease and psoriasis.

9 Claims, No Drawings

SUBSTITUTED UREA DERIVATIVES AS CELL ADHESION INHIBITORS

This application is a 371 of PCT/GB98/03334, filed Nov. 9, 1998.

This invention relates to compounds which are inhibitors of the interaction between the integrin $\alpha_4\beta_1$, also known as Very Late Antigen-4 (VLA-4) or CD49d/CD29, and its protein ligands, for example Vascular Cell Adhesion Molecule-1 (VCAM-1) and fibronectin. This invention further relates to processes for preparing such compounds, to pharmaceutical compositions containing them and to their use in methods of therapeutic application.

$\alpha_4\beta_1$ is a member of the integrin family of heterodimeric cell surface receptors that are composed of noncovalently associated glycoprotein subunits ($\alpha$ and $\beta$) and are involved in cell adhesion to other cells or to extracellular matrix. There are at least 14 different human integrin $\alpha$ subunits and at least 8 different $\beta$ subunits and each $\beta$ subunit can form a heterodimer with one or more $\alpha$ subunits. Integrins can be subdivided based on their $\beta$ subunit composition. $\alpha_4\beta_1$ is one of several $\beta_1$ integrins, also known as Very Late Antigens (VLA).

The interactions between integrins and their protein ligands are fundamental for maintaining cell function, for example by tethering cells at a particular location, facilitating cell migration, or providing survival signals to cells from their environment. Ligands recognised by integrins include extracellular matrix proteins, such as collagen and fibronectin; plasma proteins, such as fibrinogen; and cell surface molecules, such as transmembrane proteins of the immunoglobulin superfamily and cell-bound complement. The specificity of the interaction between integrin and ligand is governed by the $\alpha$ and $\beta$ subunit composition.

Integrin $\alpha_4\beta_1$ is expressed on numerous hematopoietic cells and established cell lines, including hematopoietic precursors, peripheral and cytotoxic T lymphocytes, B lymphocytes, monocytes, thymocytes and eosinophils [Hemler, M. E. et al (1987), J. Biol. Chem., 262, 11478–11485; Bochner, B. S. et al (1991), J. Exp. Med., 173, 1553–1556]. Unlike other $\beta_1$ integrins that bind only to cell-extracellular matrix proteins, $\alpha_4\beta_1$ binds to VCAM-1, an immunoglobulin superfamily member expressed on the cell surface, for example on vascular endothelial cells, and to fibronectin containing the alternatively spliced type III connecting segment (CS-1 fibronectin) [Elices, M. J. et al (1990), Cell, 60, 577–584; Wayner, E. A. et al (1989). J. Cell Biol., 109, 1321–1330].

The activation and extravasation of blood leukocytes plays a major role in the development and progression of inflammatory diseases. Cell adhesion to the vascular endothelium is required before cells migrate from the blood into inflamed tissue and is mediated by specific interactions between cell adhesion molecules on the surface of vascular endothelial cells and circulating leukocytes [Sharar, S. R. et al (1995). Springer Semin. Immunopathol., 16, 359–378]. $\alpha_4\beta_1$ is believed to have an important role in the recruitment of lymphocytes, monocytes and eosinophils during inflammation. $\alpha_4\beta_1$/ligand binding has also been implicated in T-cell proliferation, B-cell localisation to germinal centres, haemopoeitic progenitor cell localisation in the bone marrow, placental development, muscle development and tumour cell metastasis.

The affinity of $\alpha_4\beta_1$ for its ligands is normally low but chemokines expressed by inflamed vascular endothelium act via receptors on the leukocyte surface to upregulate $\alpha_4\beta_1$ function [Weber, C. et al (1996), J. Cell Biol., 134, 1063–1073]. VCAM-1 expression is upregulated on endothelial cells in vitro by inflammatory cytokines [Osbom, L. et al (1989) Cell, 59, 1203–1211] and in human inflammatory diseases such as rheumatoid arthritis [Morales-Ducret, J. et al (1992). J. Immunol., 149, 1424–1431], multiple sclerosis [Cannella, B. et al., (1995). Ann. Neurol., 37, 424–435], allergic asthma [Fukuda, T. et al (1996), Am. J. Respir. Cell Mol. Biol., 14, 84–94] and atherosclerosis [O'Brien, K. D. et al (1993). J. Clin. Invest., 92, 945–951].

Monoclonal antibodies directed against the $\alpha_4$ integrin subunit have been shown to be effective in a number of animal models of human inflammatory diseases including multiple sclerosis, rheumatoid arthritis, allergic asthma, contact dermatitis, transplant rejection, insulin-dependent diabetes, inflammatory bowel disease, and glomerulonephritis.

Integrins recognise short peptide motifs in their ligands. The minimal $\alpha_4\beta_1$ binding epitope in CS-1 is the tripeptide leucine-aspartic acid-valine (Leu-Asp-Val) [Komoriya, A., et al (1991). J. Biol. Chem., 266, 15075–15079] while VCAM-1 contains the similar sequence isoleucine-aspartic acid-serine [Clements, J. M., et al (1994). J. Cell Sci., 107, 2127–2135]. The 25-amino acid fibronectin fragment, CS-1 peptide, which contains the Leu Asp-Val motif, is a competitive inhibitor of $\alpha_4\beta_1$ binding to VCAM-1 [Makarem, R., et al (1994). J. Biol. Chem., 269, 4005–4011]. Small molecule $\alpha_4\beta_1$ inhibitors based on the Leu-Asp-Val sequence in CS-1 have been described, for example the linear molecule phenylacetic acid-Leu-Asp-Phe-D-Pro-amide [Molossi, S. et al (1995). J. Clin. Invest., 95, 2601–2610] and the disulphide cyclic peptide Cys-Trp-Leu-Asp-Val-Cys [Vanderslice, P., et al (1997). J. Immunol., 158, 1710–1718].

More recently, in WO 96/00581, Publi. date Jan. 11, 1996, and WO96/20216, Publi. date Jul. 4, 1996, cyclic peptides containing the Leu-Asp-Val sequence have been reported to inhibit the binding of $\alpha_4\beta_1$ integrin to VCAM-1 or fibronectin.

A few small non-peptidic Leu-Asp-Val surrogate compounds have been reported in WO 94/02445, Publ. date Feb. 3, 1994 to inhibit $\alpha_4\beta_1$-induced adhesion.

More recently, non-peptidic compounds of formula I which can be orally adminstered, and which inhibit VCAM/VLA4 binding have been reported in PCT application WO96/22966.

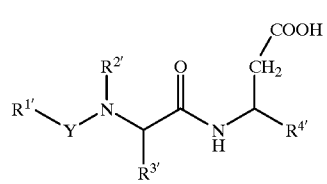

(I)

The preferred compounds are those in which in formula I, $R^{1'}$ is an urea derivative, $R^{2'}$ is hydrogen, $R^{3'}$ is an alkyl or substituted alkyl, $R^{4'}$ is dimethoxyl phenyl or benzo dioxol-5-yl and Y is CO.

There remains a continuing need for alternative compounds which inhibit the interaction between VCAM-1 and fibronectin with integrin VLA-4 and, in particular, for compounds which can be adminstered by an oral route.

We have now found a group of compounds containing a substituted phenoxy group which inhibit this interaction.

According to one aspect of the present invention there is provided a compound of formula (II)

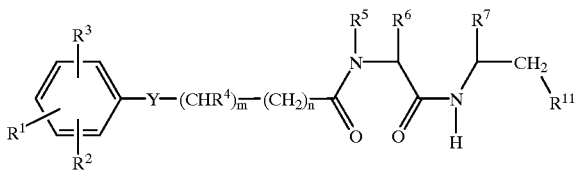

(II)

wherein:
R$^1$ is in the para or meta position and is

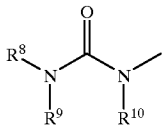

where R$^2$ and R$^3$ are each independently selected from hydrogen, nitro, C$_{1-6}$ alkyl, C$_{3-6}$ cycloalkyl, C$_{2-6}$alkenyl, C$_{2-6}$alkynyl, C$_{1-4}$ alkoxy, C$_{1-6}$ alkylamino, C$_{1-6}$dialkylamino, C$_{1-6}$alkylC$_{1-4}$alkoxyl, C$_{1-6}$alkylaminoC$_{1-6}$alkyl, amino, cyano, halogeno, trifluoromethyl, —CO$_2$R$^{12}$, and —CONR$^{12}$R$^{13}$, where R$^{12}$ and R$^{13}$ are independently selected from hydrogen or C$_{1-6}$ alkyl, or R$^2$ and R$^3$ together with the phenyl to which they are attached form a 9 or 10 membered bicyclic ring system;

R$^4$ is C$_{1-4}$alkyl;

R$^5$ is selected from hydrogen and C$_{1-4}$alkyl;

R$^6$ is selected from C$_{1-6}$ alkyl, C$_{1-4}$alkyl(C$_{4-6}$)cycloalkyl, C$_{1-6}$alkyl(C$_{1-6}$)alkoxyl, C$_{1-6}$alkylS(C$_{1-6}$)alkyl, C$_{1-4}$alkylsulphonyl(C$_{1-4}$)alkyl,

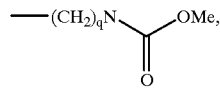

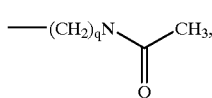

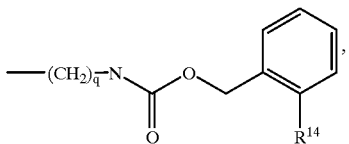

where q is an integer from 1 to 6 and R$^{14}$ is halogeno;

R$^7$ is selected from C$_{1-6}$alkyl, C$_{1-8}$alkoxylcarbonyl, C$_{2-6}$ alkenyl, 1,3-benzodioxol-5-yl and aryl optionally substituted by one or more substituents selected from C$_{1-4}$ alkoxy, C$_{1-6}$ alkyl, cyano, halogeno, and trifluoromethyl;

R$^8$ is aryl, heteroaryl, a bicyclic heteroaryl ring system linked to the nitrogen via a ring carbon or a 9 or 10 membered bicyclic ring system linked to the nitrogen via a ring carbon and each ring is optionally substituted with up to two substituents, which may be the same or different, and are selected from C$_{1-6}$ alkyl, C$_{1-4}$ alkoxy, C$_{1-4}$alkylthio, C$_{1-6}$alkylC$_{1-4}$alkoxyl, C$_{1-6}$alkylaminoC$_{1-6}$alkyl, hydroxy, —CO$_2$H, (CH$_2$)$_p$OH, where p is 1 or 2, cyano, halogeno, and trifluoromethyl;

R$^9$ and R$^{10}$ are each independently selected from hydrogen and C$_{1-4}$alkyl or R$^8$ and R$^9$ together with the nitrogen to which they are attached form a dihydroindolyl, or a dihydroquinolinyl group;

R$^{11}$ is selected from carboxyl, tetrazolyl, alkyl sulphonyl carbamoyl, sulfo and sulfino;

Y is oxygen, sulphur or sulfonyl;

m is 0 or 1 and n is 0 or an integer from 1 to 4 with the proviso that m and n cannot both be 0 and when m is 1, n is 0;

or a pharmaceutically acceptable salt or in vivo hydrolysable ester thereof.

'C$_{1-6}$alkylC$_{1-4}$alkoxy' typically means —(C$_{1-6}$)alkylO(C$_{1-4}$)alkyl, a preferred example of which is —CH$_2$OCH$_3$. 'C$_{1-6}$alkylaminoC$_{1-6}$alkyl' typically means —(C$_{1-6}$)alkylNH(C$_{1-6}$)alkyl, a preferred example of which is —CH$_2$NHC$_2$H$_5$.

'Aryl' typically means phenyl or naphthyl, preferably phenyl. 'Heteroaryl' means an aromatic 5 or 6 membered ring with up to four ring heteroatoms selected from nitrogen, oxygen and sulphur. Examples of 'heteroaryl' include pyrrolyl, fluranyl, thienyl, imidazolyl, thiadiazolyl, thiazolyl, isoxazolyl, pyridinyl, pyridyl and pyrimidimyl.

Bicyclic heteroaryl ring system means an aromatic 5,6-, 6,5 or 6,6 fused ring system wherein one or both rings contain ring heteroatoms. The ring system may contain up to three heteroatoms, independently selected from oxygen, nitrogen and sulphur. When the ring system contains more than one heteroatom at least one such heteroatom is nitrogen. An example of preferred bicyclic heteroaryl ring systems are isoquinolyl, benzothiazolyl or benzoimidazolyl.

9 or 10 membered bicyclic ring system means an aromatic 6 membered ring fused to a 5 or 6 membered ring, preferably a 5 or 6 membered saturated ring, optionally substituted with at least one heteroatom, preferably oxyygen, and linked to the nitrogen to which it is attached via a ring carbon on the aromatic 6 membered ring. A preferred example for R$^8$ is tetrahydronaphthalyl. When R$^2$, R$^3$ and the phenyl to which they are attached form such a 9 or 10 membered bicyclic ring system, preferred groups are dihydrobenzofuranyl and dihydrobenzopyranyl.

R$^2$ and R$^3$ are preferably independently selected from hydrogen, C$_{1-6}$ alkyl, C$_{1-4}$alkoxy, trifluoromethyl and halogeno and, more preferably are independently selected from methyl, methoxy, isopropoxy, trifluoromethyl, fluoro, bromo and chloro.

A preferred group for R$^4$ is C$_{1-2}$alkyl. R$^5$ is preferably selected from hydrogen, methyl and isopropyl. Preferably R$^6$ is selected from C$_{1-4}$ alkyl and C$_{1-4}$alkylS(C$_{1-4}$)alkyl and is, more preferably, selected from —CH$_2$CH(CH$_3$)(CH$_3$) and —CH$_2$CH$_2$SCH$_3$. R$^7$ is preferably selected from C$_{2-6}$ alkenyl, 1,3-benzodioxol-5-yl, and 1-isopropyl-2-methylpropyl acetyl and is, more preferably, selected from allyl and 1,3-benzodioxol-5-yl.

R$^8$ is preferably phenyl, thienyl, pyridyl, thiadiazol, isoxazolyl, thiazolyl, 5,6,7,8-tetrahydronapthalyl, isoquinolyl, 1,3-benzoimidazolyl and 1,3-benzothiazolyl each optionally substituted with up to two substituents which are preferably and independently selected from C$_{1-4}$alkyl, more preferably methyl, halogeno, more preferably fluoro, chloro and bromo; —COOH, —CH$_2$OH, hydroxy and methylthio.

R$^9$ and R$^{10}$ are each independently preferably selected from hydrogen and methyl or R$^8$ and R$^9$ together with the nitrogen to which they are attached form 2,3-dihydro-1H-indol-1-yl, or 3,4-dihydro-1 (2H)-quinolinyl. R$^{11}$ is preferably COOH. In a preferred embodiment n is 1 and m is 0. Y is preferably oxygen.

Preferred compounds according to the invention are those of formula (III)

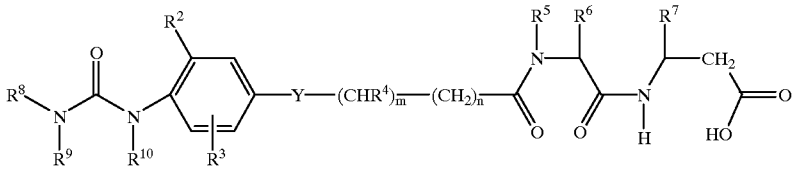

(III)

where $R^2$ to $R^8$, Y, m and n are as hereinbefore defined.

More preferred are those compounds where $R^2$ is $C_{1-4}$alkoxy, especially methoxy, $R^3$, $R^5$ and $R^{10}$ are each independently hydrogen; $R^4$ is $C_{1-4}$ alkyl; $R^6$ is selected from $C_{1-4}$alkyl and $C_{1-4}$alkylS($C_{1-4}$)alkyl and is especially —$CH_2CH(CH_3)(CH_3)$ or —$CH_2CH_2SCH_3$; $R^7$ is 1,3-benzodioxol-5-yl; $R^8$ is aryl or heteroaryl each optionally substituted with one substitutent selected from $C_{1-6}$alkyl, especially methyl, $CH_2OH$, halogeno, especially chloro or fluoro, and hydroxy and $R^9$ is hydrogen or $C_{1-4}$alkyl or $R^8$ and $R^9$ together with the nitrogen to which they are attached form a dihydroindolyl or a dihydroquinolinyl; and m and n are 0 or 1 with the proviso that n and m cannot both be 0 or 1 and most preferably m is 0 and n is 1.

Particularly preferred compounds include 4-N'-(2-methylphenyl)urea)-3-methoxy phenoxyacetyl (leucine-3-amino-(3,4-methylenedioxy)phenylpropionic acid)amide;

4-(N'-phenylurea)-3-methoxy phenoxyacetyl (leucine-3-amino-(3,4-methylenedioxy)phenylpropionic acid)amide; 4-(N'-(2-chlorophenyl)urea)-3-methoxy phenoxyacetyl (leucine-3-amino-(3,4-methylenedioxy) phenylpropionic acid)amide;

7-(N'-(2-methylphenyl)urea)-2,3-dihydrobenzofuranyl-4-oxyacetyl(leucine-3-amino-(3,4-methylenedioxy) phenylpropionic acid)amide; 4-(N'-(2-hydroxymethylphenyl)urea)-3-methoxy phenoxyacetyl (leucine-3-amino-(3,4-methylenedioxy) phenylpropionic acid)amide;

4-[(2,3-dihydro-1H-indol-1ylcarbonyl)amino]-3-methoxy phenoxyacetyl (leucine-3-amino-(3,4-methylenedioxy)phenylpropionic acid)amide; 4-(N'-(2-fluorophenyl)urea)-3-methoxy phenoxyacetyl (leucine-3-amino-(3,4-methylenedioxy) phenylpropionic acid)amide;

4-(N'-(2-hydroxy-6-methylphenyl)urea)-3-methoxy phenoxyacetyl (leucine-3-amino-(3,4-methylenedioxy) phenylpropionic acid)amide; and 4-(N'-(2-methylphenyl)urea)-3-isopropoxy phenoxyacetyl (leucine-3-amino-(3,4-methylenedioxy) phenylpropionic acid)amide.

The compounds of formulae (II) and (III) possess chiral centres, at —$CHR^6$, and at —$CHR^7$. When $R^6$ is either —$CH_2CH(CH_3)(CH_3)$ or —$CH_2CH_2SCH_3$ and, therefore, the compounds of the invention of formulae (II) and (III) contains leucine or methionine as a sub-unit, the latter are in their proteinogenic (or natural) configuration. The present invention covers all diastereoisomers that inhibit the interaction between VCAM-1 and fibronectin with integrin VLA-4.

According to another aspect of the present invention there is provided a compound of formula (IV)

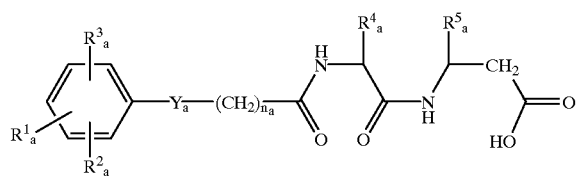

(IV)

wherein:

$R^1_a$ is in the para or meta position and is

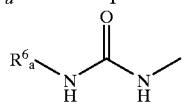

where $R^2_a$ and $R^3_a$ are each independently selected from hydrogen, nitro, $C_{1-6}$ alkyl, $C_{3-6}$ cycloalkyl, $C_{2-6}$alkenyl, $C_{2-6}$alkynyl, $C_{1-4}$ alkoxy, $C_{1-6}$ alkylamino, $C_{1-4}$alkoxyl$C_{1-6}$alkyl, $C_{1-6}$alkylamino$C_{1-6}$alkyl, cyano, halogeno, trifluoromethyl, —$CO_2R^7_a$ and —$CON R^7_a R^8_a$ where $R^7_a$ and $R^8_a$ are independently selected from hydrogen or $C_{1-6}$ alkyl;

$R^4_a$ is selected from $C_{1-6}$ alkyl, $C_{1-6}$alkoxy-substituted ($C_{1-6}$)alkyl, and $C_{1-6}$alkylS($C_{1-6}$)alkyl;

$R^5_a$ is selected from $C_{1-6}$alkyl, $C_{2-6}$ alkenyl, 1,3-benzodioxol-5-yl and aryl optionally substituted by at least one substituent selected from $C_{1-4}$ alkoxy, $C_{1-6}$ alkyl, cyano, halogeno, and trifluoromethyl;

$R^6_a$ is aryl or heteroaryl and the ring is optionally substituted with up to two substituents, which may be same or different, selected from $C_{1-6}$ alkyl, $C_{1-4}$ alkoxy, $C_{1-4}$alkoxy$C_{1-6}$alkyl, $C_{1-6}$alkylamino$C_{1-6}$alkyl, cyano, halogeno, and trifluoromethyl;

$Y_a$ is oxygen or sulphur; and $n_a$ is an integer from 1 to 4;

or a pharmaceutically acceptable salt or in vivo hydrolysable ester thereof.

In compounds of formula (IV), 'aryl' typically means phenyl or naphthyl, preferably phenyl. 'Heteroaryl' means an aromatic 5 or 6 membered ring with up to four ring heteroatoms selected from nitrogen, oxygen and sulphur. Examples of 'heteroaryl' include pyrrolyl, furanyl, thienyl, imidazolyl, thiazolyl, pyridinyl and pyrimidimyl.

$R^2_a$ and $R^3_a$ are preferably independently selected from hydrogen, $C_{1-6}$ alkyl, trifluoromethyl and halogeno and, most preferably, are independently selected from methyl, trifluoromethyl and chloro. $R^4_a$ is preferably selected from $C_{1-4}$ alkyl and $C_{1-4}$alkylS($C_{1-4}$)alkyl and is, more preferably, selected from —$CH_2CH(CH_3)(CH_3)$ and —$CH_2CH_2SCH_3$. Preferably, $R^5_a$ is selected from $C_{2-6}$ alkenyl, more preferably allyl, and 1,3-benzodioxol-5-yl. $R^6_a$ is preferably phenyl with up to two substituents which are preferably and independently selected from $C_{1-4}$ alkyl, most preferably methyl, and halogeno, most preferably chloro and bromo. The preferred value for n is 1.

The compounds of formula (IV) of the present invention possess chiral centres, at —CHR$^4_a$, and at —CHR$^5_a$. When R$^4_a$ is either —CH$_2$CH(CH$_3$)(CH$_3$) or —CH$_2$CH$_2$SCH$_3$ and, therefore, the compound of the invention of formula (IV) contains leucine or methionine as a sub-unit, the latter are in their proteinogenic (or natural) configuration. The present invention covers all diasteroisomers that inhibit the interaction between VCAM-1 and fibronectin with integrin VLA-4.

Pharmaceutically acceptable salts of the compounds of formulae (II), (III) and (IV) include acid addition salts such as salts formed with mineral acids, for example, hydrogen halides such as hydrogen chloride and hydrogen bromide, sulphonic and phosphonic acids; and salts formed with organic acids, especially citric, maleate, acetic, oxalic, tartaric, mandelic, p-toluenesulphonic, methanesulphonic acids and the like. In another aspect, suitable salts are base salts such as alkali metals salts, for example, sodium and potassium; alkaline earth metal salts such as magnesium and calcium; aluminium and ammonium salts; and salts with organic bases such as ethanolamine, methylamine, diethylamine, isopropylamine, trimethylamine and the like. Such salts may be prepared by any suitable method known in the art.

In vivo hydrolysable esters are those pharmaceutically acceptable esters that hydrolyse in the human body to produce the parent compound. Such esters can be identified by administering, for example intravenously to the test animal, the compound under test and subsequently examining the test animal's body fluids. Suitable in vivo hydrolysable esters for hydroxy include acetyl and for carboxyl include, for example, C$_{1-6}$alkoxy methyl esters for example methoxymethyl, C$_{1-6}$alkanoyloxymethyl esters for example pivaloyloxymethyl, phthalidyl esters, C$_{3-8}$cycloalkoxycarbonyloxyC$_{1-6}$alkyl esters for example 1-cyclohexylcarbonyloxyethyl; 1,3-dioxolan-2-ylmethyl esters for example 5-methyl-1,3-dioxolan-2-ylmethyl; and C$_{1-6}$alkoxycarbonyloxyethyl esters for example 1-methoxycarbonyloxyethyl.

The activities of the compounds of this invention to inhibit the interaction between VCAM-1 and fibronectin with integrin VLA-4 may be determined using a number of in vitro and in vivo screens. They show improved potency compared to prior art compounds.

For example, the compounds according to the invention preferably have an IC$_{50}$ of <10 $\mu$M, more preferably <1 $\mu$M in the MOLT-4 cell/Fibronectin assay hereinafter described.

Preferred compounds have shown activity in a number of in vivo screens in mice, for example, delayed-type hypersensitivity (DTH) responses induced by ovalbumin in the footpad and collagen-induced arthritis.

In order for it to be used, a compound of formulae (II), (III) or (IV) or a pharmaceutically acceptable salt or an in vivo hydrolysable ester thereof is typically formulated as a pharmaceutical composition in accordance with standard pharmaceutical practice.

Thus, according to a further aspect of the invention there is provided a pharmaceutical composition which comprises a compound of formula (II), (III) or (IV) or a pharmaceutically acceptable salt or an in vivo hydrolysable ester thereof and a pharmaceutically acceptable carrier.

The pharmaceutical composition of this invention may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension, or a depot formulation with drug incorporated in a biodegradable polymer. The composition may be in a form suitable for topical administration such as for example creams, ointments and gels. Skin patches are also contemplated. For these purposes, the composition of this invention may be formulated by means known in the art, such as for example, as described in general terms, in Chapter 25.2 of Comprehensive Medicinal Chemistry, Volume 5, Editor Hansch et al, Pergamon Press 1990.

Furthermore, the pharmaceutical composition of the present invention may contain one or more additional pharmacological agents suitable for treating one or more disease conditions referred to hereinabove in addition to the compounds of the present invention. In a further aspect, the additional pharmacological agent or agents may be co-administered, either simultaneously or sequentially, with the pharmaceutical composition of the invention.

The composition of the invention will normally be administered to humans such that the daily dose will be 0.01 to 75 mg/kg body weight and preferably 0.1 to 15 mg/kg body weight. A preferred composition of the invention is one suitable for oral administration in unit dosage form for example a tablet or capsule which contains from 1 to 1000 mg and preferably 10 to 500 mg of a compound according to the present invention in each unit dose.

Thus, according to yet another aspect of the invention, there is provided a compound of formulae (II), (III) or (IV) or a pharmaceutically acceptable salt or an in vivo hydrolysable ester thereof for use in a method of therapeutic treatment of the human or animal body.

In yet a further aspect of the invention the present invention provides a method of treating a disease mediated by the interaction between VCAM-1 and/or fibronectin and the integrin receptor VLA-4 in need of such treatment which comprises administering to said warm-blooded mammals an effective amount of a compound of formulae (II), (III) or (IV) or a pharmaceutically acceptable salt or an in vivo hydrolysable ester thereof.

The present invention also provides the use of a compound of formulae (II), (III) or (IV) or a pharmaceutically acceptable salt or an in vivo hydrolysable ester thereof in the production of a medicament for use in the treatment of a disease or medical condition mediated by the interaction between fibronectin and/or VCAM-1 (especially VCAM-1) and the integrin receptor VLA-4.

In one embodiment of the invention the manumal in need of treatment is suffering from multiple sclerosis, rheumatoid arthritis, asthma, coronary artery disease or psoriasis.

In another aspect of the invention, there is provided a process for preparing a compound of formula (II) where R$^{11}$ is COOH or a pharmaceutically acceptable salt or an in vivo hydrolysable ester thereof which process comprises coupling together i) a compound of formula (V)

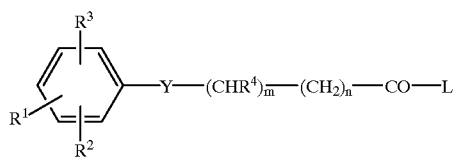

(V)

and a compound of formula (VI)

NHR$^5$—CHR$^6$—CONH—CHR$^7$—CH$_2$—COOH (VI)

or ii) a compound of formula (VII)

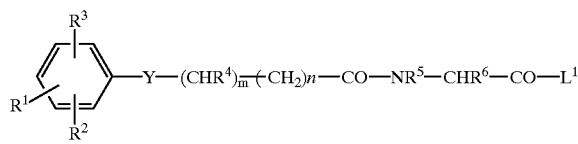

(VII)

and a compound of formula (VIII)

NH$_2$—CHR$^7$—CH$_2$—COOH     (VIII)

wherein L and L$^1$ are leaving groups and any functional group is optionally protected; and thereafter, if necessary:

a) removing any protecting group; and
b) forming a pharmaceutically acceptable salt or in-vivo hydrolysable ester.

The reactions of (V) and (VI) or (VII) and (VIII) are performed under standard coupling conditions for forming peptide bonds. They can be performed either on a solid support (Solid Phase Peptide Synthesis) or in solution using normal techniques used in the synthesis of organic compounds. With the exception of the solid support, all the other protecting groups, coupling agents, deblocking reagents and purification techniques are similar in both the solid phase and solution phase peptide synthesis techniques.

During the reaction, amino acid functional groups may, if necessary, be protected by protecting groups, for example Boc. Such groups can be cleaved when necessary using standard techniques such as acid or base treatment.

Suitable protecting groups for the protection of the carboxyl groups include esters.

Coupling reagents for forming peptide bonds include the commonly used azide, symmetrical anhydride, mixed anhydride and various active esters and carbodiimides. In the case of carbodiimides, additives such as 1-hydroxybenzotriazole and N-hydroxysuccinimide may also be added. Other coupling reagents include 1H-benzotriazole-1-yl-oxy-tris-pyrrolidinophosphonium hexafluorophosphate (PyBOP), (2-(1H-benzotriazole-1-yl)-1,1,3,3-tetramethyluronium tetrafluoroborate (TBTU), (2-(1H-benzotriazole-1-yl)-1,1,3,3-tetramethyluronium hexafluorophosphate (HBTU)] and O-(7-azabenzotriazol-1-yl)-1,1,3,3-tetramethyluronium hexafluorophosphate (HATU).

The coupling reactions can be performed at temperatures between −20° C. to 40° C. The time of the reaction can vary such as between 10 minutes and 24 hours. Suitable purification methods for the intermediates and final products include chromatographic techniques such as high pressure liquid chromatography (HPLC) along with many other standard techniques used in organic chemistry (e.g. solvent extraction and crystallisation).

The following abbreviations are used:

| | |
|---|---|
| Boc | tert-butoxycarbonyl |
| DIPEA | diisopropylethyamine |
| DMF | dimethylformamide |
| DMSO | dimethylsulphoxide |
| Et$_3$N | triethylamine |
| HATU | O-(7-azabenzotriazol-1-yl)-1,1,3,3-tetramethyluronium hexafluorophosphate |
| HOBT | 1-hydroxybenzotriazole |
| Su | succinimido |
| TFA | trifluoroacetic acid |
| THF | tetrahydrofuran |
| WSCDI | 1-(3-dimethylaminopropyl)-3-ethylcarbodiimide methoiodide or methochloride |

Preferred coupling conditions for reacting compounds of formula (V) and (VI) or (VII) and (VIII) are, in particular, a) HATU/DIPEA/DMF
b) HOBT/WSCDI/DIPEA/DMF
c) HOBT/WSCDI/DIPEA/N-methylmorpholine Compounds of formula (VI) may be prepared by reacting a compound of formula (IX)

NHR$^5$CHR$^6$COL'     (IX)

with a compound of formula (VIII). Preferably the compound of formula (IX) is in the form of Boc-amino acid or Boc-amino acid-OSu and the coupling reagents are selected from d) HATU/DMF/DIPEA;
e) HOBT/WSCDI/DIPEA/DMF/CH$_2$Cl$_2$; and
f) Et$_3$N/CH$_2$Cl$_2$;

The protecting group may be removed using any suitable reagent known in the art, a particularly preferred example of which is trifluoroacetic acid Compounds of formula (VI) may be prepared by reacting a compound of formula (V) and a compound of formula (IX) in a standard manner.

Exemplary methods of preparing compounds of formula (VIII) are as follows. When R$^7$ is aryl or 1,3-benzodioxol-5-yl, the following method may used.

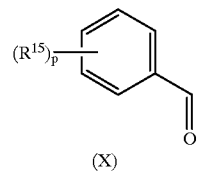

(X)

Ph$_3$P═CHCO$_2$CH$_3$/THF

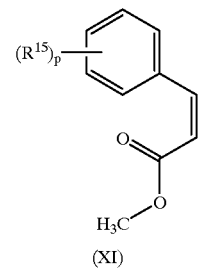

(XI)

THF can be replaced by other inert solvent such as DMF.

N-Benzyl-l-phenylethylamine
n-BuLi
−70°

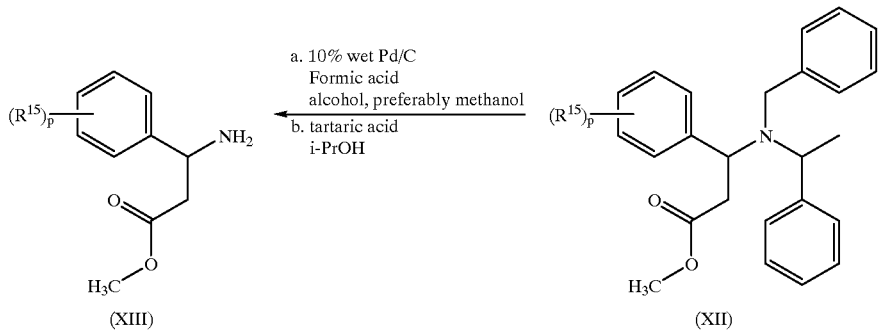

where $R^{15}$ is a substituent selected from $C_{1-4}$ alkoxyl, $C_{1-6}$ alkyl, cyano, halogeno and trifluoromethyl; or

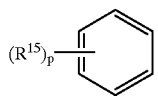

forms 1,3-benzodioxol-5-yl and p is an integer from 1 to 4.

When $R^7$ is $C_{2-6}$ alkenyl the following method may be used

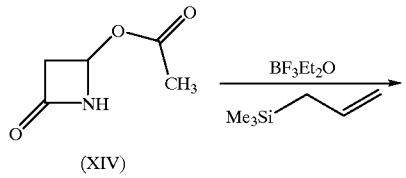

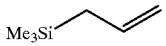

As will be appreciated from the art $BF_3Et_2O$ can be replaced by other known Lewis acids, replaced by, for example, by allyl bromide, and HCl/MeOH may be replaced by, for example, HBr/acetic acid.

An exemplary method of preparing a compound of formula (V) where Y is oxygen, m is 0, n is 1 and $R^8$ is a 6 membered aromatic ring is as follows, where $R^{16}$ and $R^{17}$ are independently selected from hydrogen, $C_{1-6}$ alkyl, $C_{1-4}$ alkoxy, $C_{1-4}$alkylthio, $C_{1-6}$alkyl$C_{1-4}$alkoxy, $C_{1-6}$alkylamino$C_{1-6}$alkyl, hydroxy, —$CO_2H$, —$(CH_2)_pOH$ where p is 1 or 2, cyano, halogeno and trifluoromethyl:

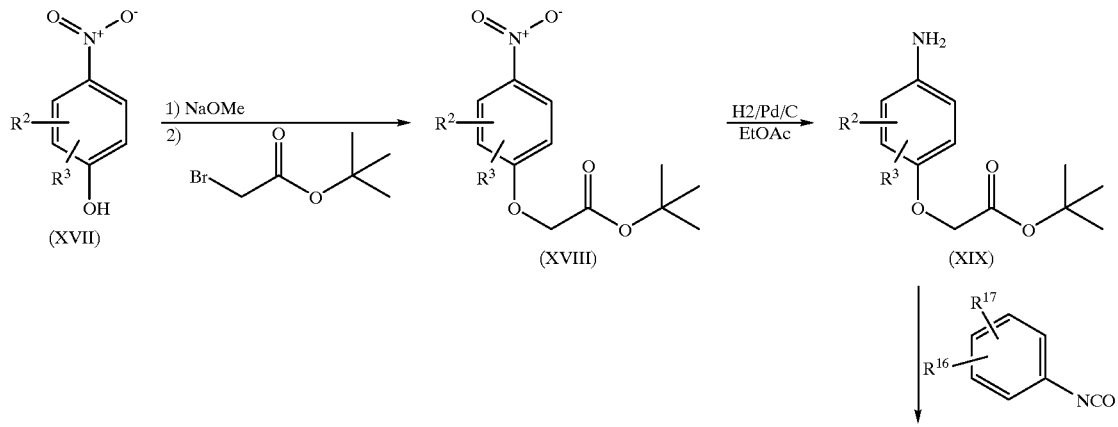

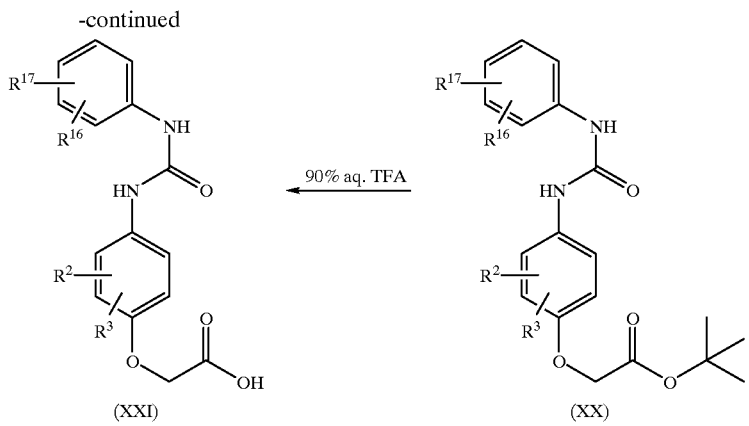

(XXI)    (XX)

In the first step of the reaction bases other than sodium methoxide may be used and esters other t-butyl esters could be used but these will typically require a final basic rather than acid hydrolysis to form the final product. For compounds of formula (V) where m is 0 and n is 2 the phenoxide ion (XVII) will be added to an acrylic ester. A further route for preparing compounds of formula (XXI) involves reacting a compound of formula (XIX) with triphosgene and then an amine of formula (XXII). Alternatively the triphosgene can be reacted with amine (XXII) and then the compound of formula (XIX).

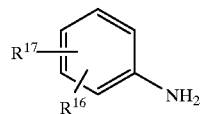

(XXII)

Compounds of formula (XXI) may also be prepared according to the following reaction:

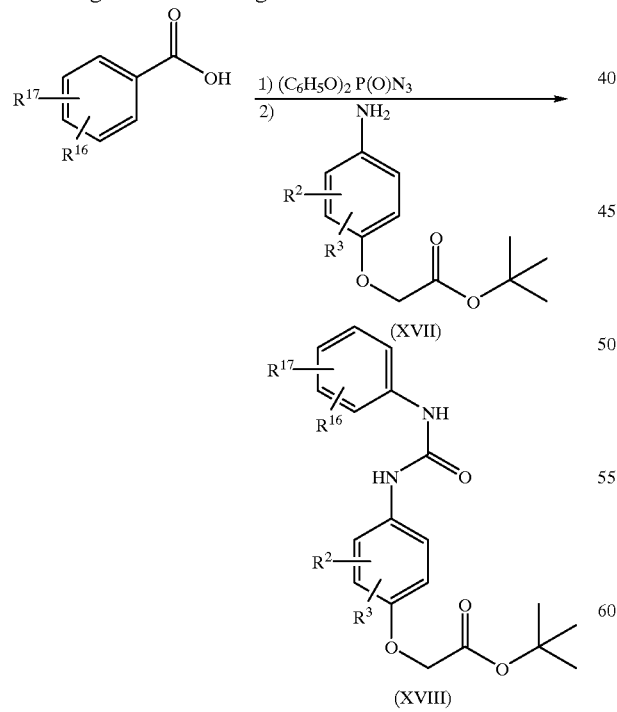

When Y is sulphur an exemplary method of preparing the compounds of invention is as follows. A compound of formula (V) can be formed by reacting phenyl isocyanate, optionally substituted on the phenyl ring, with a 2-(4-aminophenylthio)acetic acid. To this is added a coupling reagent and a compound of formula (VI) and (VII).

When Y is sulphonyl an exemplary method of preparing the compounds of the invention is as follows. A compound of formula (II) in which Y=S is oxidised by treatment with Oxone, m-chloroperbenzoic or other suitable oxidant. In the process the intermediate sulphoxide (Y=SO) may be isolated initially and further more vigorous conditions employed to give the sulphonyl derivatives.

When $R^{11}$ is acyl sulphonamide (—CONHSO$_2$R$^x$) in a compound of formula (II) an exemplary method of preparing these compounds is as follows. A compound of formula (II) in which $R^{11}$ is —CO$_2$H is treated with a sulphonamide of formula R$^x$SO$_2$NH$_2$ in the presence of 4-dimethylaminopyridine and a carbodiimide.

Compounds of the invention may contain more than two units which are to be joined together by the formation of amide links. Where such units are present, the person skilled in the art will be aware of the preferred order of joining such units together.

The invention is further illustrated by the following biological test methods, data and non-limiting Examples.

Table 1 refers to examples 13 to 76. It gives the structure of the final materials and their analysis. It also refers to the method by which they were prepared by reference to a code.

EXAMPLES

Example 1

Preparation of 4-(N'-(2-methylphenyl)urea)-phenoxyacetyl(methionine-3-amino-3,4-(methylenedioxy)phenylpropionic acid)amide

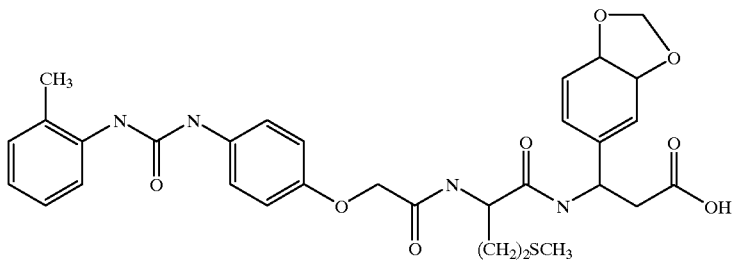

A suspension of 4-(N'-(2-methylphenyl)urea) phenoxyacetyl(methyl methionine-3-amino-3-(3,4-methylenedioxyphenyl)propionate)amide (1.3 g, 2 mmol) in a mixture of methanol (250 mL) and THF (100 ml) was treated with 1N LiOH (12.3 ml, 12 mmol). The reaction was stirred at room temperature for two hours. Water (75 ml) and DMF (10 ml) were added and the reaction was stirred for a further two hours. The reaction mixture was then concentrated to ¼ volume and the solution acidified to pH 2 with 1M citric acid giving a white solid. The solid was filtered, washed with water and then ether to give the acid (615 mg, 48%) as a white solid.

1H NMR (DMSO d6, 300 MHz, ppm) 8.80 (s, 1H), 8.46 (d, 1H), 8.00 (d, 1H), 7.80 (d, 2H), 7.36 (d, 2H), 7.08–7.18 (m, 2H), 6.72–6.96 (m, 6H), 5.98 (s, 2H), 5.10 (q, 1H), 4.48 (s, 2H), 4.40 (q, 1H), 2.56–2.74 (m, 2H), 2.18–2.28 (m, 5H), 1.70–1.90 (m, 2H); ESPMS (M+H) 623; HPLC-Dynamax 60A column C18 acetonitrile/water/0.1%TFA 10%–70% over 20 min Rt 17.35 min.

a) Preparation of methyl N-(t-butoxycarbonyl) methionine-3-amino-3-(3,4-methylenedioxyphenyl) propionate This was prepared according to the method described below (example 3a) for the preparation of methyl N-(t-butoxycarbonyl)leucine-3-amino-5-hexenoate except methyl 3-amino-3-(3,4-methylenedioxyphenyl)propionate (prepared according to the method described in WO96/22966 (Biogen) at pages 52 to 55 and incorporated herein by reference) was used in place of methyl 3-amino-5-hexenoate hydrochloride and N-(t-butoxycarbonyl)methionine was used in place of N-(t-butoxycarbonyl)leucine. Methyl N-(t-butoxycarbonyl)methionine-3-amino-3-(3,4-methylenedioxyphenyl)propionate. 1H NMR (DMSO-d6, 300 MHz, ppm): 1.3(9H,m), 1.6–1.8(2H,m), 2.0 (3H,s), 2.3–2.4(2H,t), 2.7–2.8(2H,m), 3.5(3H,s), 3.9–4.0(1H,m), 5.1(1H,m), 5.9(2H,s), 6.7–6.9(4H,m), 8.2(1H,d): m/Z 455 (M+H).

b) Preparation of methyl methionine-3-amino-3-(3,4-methylene dioxyphenyl)propionate This was prepared according to the method described below (example 3b) for the preparation of methyl leucine-3-amino-5-hexenoate except methyl N-(t-butoxycarbonyl) methionine-3-amino-3-(3,4-methylenedioxyphenyl) propionate was used in place of methyl N-(t-butoxycarbonyl)leucine-3-amino-5-hexenoate. Methyl methionine-3-amino-3-(3,4-methylene dioxyphenyl) propionate 1H NMR (DMSO-d6, 300 MHz, ppm): 1.8–1.9 (2H,m), 2.0 (3H,s), 2.2–2.4(2H,m), 2.7–2.9(2H,m), 3.5(3H,s), 3.7(1H,t), 5.1(1H,b), 6.0(2H,s), 6.7–6.9(3H,m), 7.1–7.4 (2H,b), 8.8(1H,d): m/Z 355 (M+H).

c) Preparation of t-butyl 4-nitrophenoxyacetate

A stirred solution of 4-nitrophenol (23 g) in methanol (200 ml) was treated at ambient temperature with a solution of sodium methoxide (9.3 g) in methanol (50 ml). The solution was evaporated to dryness under reduced pressure and the residue was suspended in toluene (100 ml). The toluene suspension was evaporated to dryness under reduced pressure and the residue washed by decantation with isohexane. The resulting solid was dissolved in dimethylformamide (250 ml) and the resulting stirred suspension was treated at ambient temperature over 10 minutes with undiluted t-butyl bromoacetate(35 g). The mixture was heated to 60° C. for 2 hours and then diluted with ice and water (400 ml). The mixture was extacted with ethyl acetate (3×150 ml) and the combined extracts washed with 2N potassium hydroxide (2×100 ml) at 0° C., water (100 ml) and saturated brine. The extract was dried (MgSO$_4$) and evaporated. The residue was triturated with isohexane and the crystals filtered off and washed with isohexane.

t-butyl 4-nitrophenoxyacetate 36.3 g (86%). mp 83–84° C. 1H NMR (DMSO-d6, 300 MHz, ppm): 1.45(9H,s), 4.88(2H,s), 7.10 (2H, d), 8.17(2H,d): m/Z 254 (M+H).

d) Preparation of t-butyl 4-(N'-(2-methylphenyl) urea)phenoxyacetate

At ambient temperature a rapidly stirred solution of t-butyl 4-nitrophenoxyacetate (10 g) in ethyl acetate (200 ml) containing 5% palladium on carbon (1 g) was exposed to an atmosphere of hydrogen. When uptake of hydrogen had ceased the solution was filtered and the filter cake washed with ethyl acetate. The combined filtrates were cooled to 5° C. and treated with stirring with undiluted 2-methylphenylisocyanate (7.9 g). The solution was heated to 60° C. for 2 hours. The solution was then chilled to 0° C. and the precipitate filtered and washed with cold ethyl acetate to give t-butyl 4-(N'-(2-methylphenyl)urea) phenoxyacetate 8.1 g (57%) mp 177–78° C. 1H NMR (DMSO-d6, 300 MHz, ppm): 1.43 (9H,s), 2.21(3H,s), 4.58 (2H,s), 6.83 (2H,d), 6.91(2H,t), 7.15 (2H, q), 7.37(2H, d), 7.8(1H,s), 8.8(1H,s): m/Z 357(M+H).

e) Preparation of 4(N'-(2-methylphenyl)urea) phenoxyacetic acid

A stirred solution of t-butyl 4-(N'-(2-methylphenyl)urea) phenoxyacetate (5 g) in methylene chloride (50 ml) at 0° C. was treated with 95% (v/v) trifluoroacetic acid (50 ml). Stirring was continued for two hours during which time the solution reached ambient temperature. The volatile solvents were removed by distillation at reduced pressure and the residue was diluted with water (200 ml). The precipitate was collected by filtration and washed with water. The crude material was recrystallised from isopropanol to give 4-(N'-(2-methylphenyl)urea)phenoxyacetic acid. 3.1 g. (73%) mp 216–218° C. 1H NMR (DMSO-d6, 300 MHz, ppm): 1H NMR (DMSO-d6, 300 MHz, ppm): 2.21 (3H, s), 4.54(2H, s), 6.83 (2H, d), 6.90 (2H,t), 7.15(2H,q), 7.8 (1H, s), 8.80(1H, s): m/Z 301 (M+H).

f) Preparation of 4-(N'-(2-methylphenyl)urea) phenoxyacetyl-(methyl methionine-3-amino-3-(3,4-methylenedioxyphenyl)propionate)amide A solution of the 4-(N'-(2-methylphenyl)urea) phenoxyacetic acid (710 mg, 2 mmol) in DMF (6 mL) was treated with the methyl methionine-3-amino-3-(3,4-methylene dioxyphenyl) propionate (600 mg, 2 mmol), (O-(7-azabenzotriazol-1-yl)-1,1,3,3-tetramethyluronium hexafluorophosphate) (760 mg, 2 mmol) and diisopropyl-ethylamine (0.7 ml, 4 mmol). The mixture was stirred at room temperature overnight. The mixture was partitioned between EtOAc and water. The EtOAc layer was separated, washed with 1M citric acid, saturated NaHCO$_3$ solution and concentrated in vacuo to a white solid. The solid was washed with water and ether to give the coupled product (1.3 g, 100%) as a white solid.

NMR (DMSO d6, 300 MHz, ppm) 8.88 (s, 1H), 8.48 (d,1H), 8.02 (d, 1H), 7.84 (s, 1H), 7.80 (d, 2H), 7.38 (d, 2H), 7.06–7.18 (m, 2H), 6.84–6.94 (m, 4H), 6.80 (d, 1H), 6.74 (d, 1H), 5.98 (s, 2H), 5.10 (q, 1H), 4.48 (s, 2H), 4.38 (q, 1H), 3.52 (s, 3H), 2.70–2.78 (m, 2H), 2.20–2.30 (m, 5H), 1.92 (s, 3H), 1.70–1.88 (m, 2H); ESPMS (M+H) 637; HPLC-Dynamax 60A C18 acetonitrile/water/0.1%TFA 10%–70% over 20 min Rt 19.04 min.

Example 2

Preparation of 4-(N'-(2-methylphenyl)urea) phenoxyacetyl (leucine-3-amino-(3,4-methylenedioxy)phenylpropionic acid)amide This was prepared according to example 1 except 4-(N'-(2-methylphenyl)urea)phenoxyacetyl(methyl leucine-3-amino-3-(3,4-methylenedioxyphenyl)propionate)amide was used in place of 4-(N'-(2-methylphenyl)urea)-phenoxyacetyl (methyl methionine-3-amino-3-(3,4-(methylenedioxy) phenylpropionate)amide.

1H NMR (DMSO-d6, 300 MHz, ppm): 0.9(6H, m), 1.2(3H,m), 2.1(3H,s), 2.5(2H,m), 4.3 (1H, m), 4.4(2H,S), 5.0(1H, m), 5.9(2H,s), 6.6(6H,m), 7.0–7.1(2H,dd), 7.3–7.4 (2H,d), 7.9(1H,d), 8.0(1H,d), 8.2(1h,s), 8.9(1H,d), 9.1(1H, s): m/Z 603 (M–H). HPLC Dynamax 60A C18 column; acetonitrile/water/0.1%TFA 10–70% over 20 min Rt 17.5 min a) Preparation of methyl N-(t-butoxycarbonyl) leucine-3-amino-3-(3,4-methylenediosyphenyl) propionate This was prepared according to the method described below (example 3a) for the preparation of methyl N-(t-butoxycarbonyl)leucine-3-amino-5-hexenoate except methyl 3-amino-3-(3,4-methylenedioxyphenyl)propionate (see example 1) was used in place of methyl 3-amino-5-hexenoate hydrochloride.

1H NMR (DMSO-d6, 300 MHz, ppm): 0.9(6H, m), 1.3–1.5(3H,m), 2.7(2H,m), 3.5(3H,s), 4.8–4.9(1H,m), 5.1–5.2(1H, m), 5.9(2H,s), 6.7–6.9(4H,m), 8.2(1h,d),: m/Z 437 (M+H).

b) Preparation of methyl leucine-3-amino-3-(3,4-methylene dioxyphenyl)propionate This was prepared according to the method described below (example 3b) for the preparation of methyl leucine-3-amino-5-hexenoate except methyl N-(t-butoxycarbonyl) leucine-3-amino-3-(3,4-methylenedioxyphenyl)propionate was used in place of methyl N-(t-butoxycarbonyl)leucine-3-amino-5-hexenoate.

1H NMR (DMSO-d6, 300 MHz, ppm): 0.8(6H, m), 1.3–1.5(2H,m), 1.5–1.6(1H,m), 2.7(2H,m), 3.3–3.4(1H,m), 3.5(3H,s), 4.9–5.3(2H,b), 5.1–5.2(1H, m), 6.0(2H,s), 6.7–6.9(3H,m), 8.4–8.5(1H,d),: m/Z 337 (M+H).

c) Preparation of 4-(N'-(2-methylphenyl)urea) phenoxyacetyl-(methyl leucine-3-amino-3-(3,4-methylenedioxyphenyl)propionate)amide This was prepared according to example 1f except methyl leucine-3-amino-3-(3,4-methylenedioxyphenyl)propionate was used in place of methyl methionine-3-amino-3-(3,4-methylenedioxyphenyl)propionate.

1H NMR (DMSO-d6, 300 MHz, ppm): 0.9(6H, m), 1.3–1.4(3H,m), 2.2(3H,s), 2.7(2H,m), 3.5(3H,s), 4.3 (1H, m), 4.4(2H,S), 5.0(1H, m), 5.9(2H,s), 6.7–6.9(6H,m), 7.0–7.1(2H,q), 7.3–7.4(2H,d), 7.7–7.8(2H,m), 8.0(1H,d), 8.4–8.5(1h,d), 8.9(1H,s): m/Z 619 (M+H). HPLC Dynamax 60A C18 column; acetonitrile/water/0.1%TFA 10–70% over 20 min Rt 19.0 min.

Example 3

Preparation of 4-(N'-(2-methylphenyl)urea) phenoxyacetyl (leucine-3-amino-5hexenoicacid) amide This was prepared according to example 1 except 4-(N'-(2-methylphenyl)urea)phenoxyacetyl(methyl leucine-3-amino-5-hexenoate)amide was used in place of 4-(N'-(2-methylphenyl)urea)-phenoxyacetyl (methyl methionine-3-amino3-(3,4-methylenedioxyphenyl)propionate)amide.

1H NMR (DMSO-d6, 300 MHz, ppm): 0.9(6H, m), 1.3–1.5(3H,m), 2.0–2.2(2h,m), 2.2(3H,s), 2.3(2H,d), 4.0 (1H,m), 4.3 (1H, m), 4.4(2H,S), 4.9–5.0(2H, dd), 5.6–5.7 (1H,m), 6.8–6.9(3H,m), 7.1–7.2(2H,m), 7.3–7.4(2H,d), 7.8 (2H,d), 7.9–8.0(2H,m), 8.8(1H,s), 12.2(1H,b): m/Z 523 (M–H). HPLC Dynamax 60A C18 column; acetonitrile/water/0.1%TFA 10–70% over 20 min Rt 16.8 min a) Preparation of methyl N-(t-butoxycarbonyl) leucine-3-amino-5-hexenoate

HOBT (255 mg) was added to a solution of N-(t-butoxycarbonyl)leucine (297 mg) in DMF (5 ml), followed by 1-(3-Dimethylaminopropyl)-3-ethylcarbodiimide hydrochloride (273 mg) and the solution stirred for 15 min. Methyl 3-amino-5-hexenoate hydrochloride (185 mg) was dissolved in DMF (5 ml) and triethylamine (140 μl) and the resultant solution added to the solution of the N-(t-butoxycarbonyl)leucine activated ester followed by diisopropylethylamine (100 μl). The mixture was stirred overnight at ambient temperature. The mixture was added to ethyl acetate(30 ml), washed with water (2×5 ml), 5% citric acid (3 ml), water (5 ml), saturated sodium bicarbonate solution (5 ml), water (5 ml), saturated brine (5 ml), dried (MgSO$_4$) and evaporated to give methyl N-(t-butoxycarbonyl)leucine-3-amino-5-hexenoate (335 mg); NMR (CDCl$_3$): 0.9 (6H, d), 1.4(10H, m), 1.6–1.8 (2H, m), 2.2–2.3 (2H,m), 2.5(2H,d), 3.6(3H,s), 4.0–4.1(1H, m), 4.2–4.3 (1H,m), 4.8–4.9(1H,b), 5.0–5.1 (2H,d), 5.6–5.8 (1H, m), 6.5–6.6(1H,m): m/Z 357 (M+H)

b) Preparation of methyl leucine-3-amino-5-hexenoate

Methyl N-(t-butoxycarbonyl)leucine-3-amino-5-hexenoate (10 g) was treated with 90% TFA in water(100 ml). The mixture was stirred for 30 min and the TFA and water were then removed by evaporation. The residue was purified by preparative HPLC on a C18 silica column eluting with acetonitrile/water/0.1% TFA to give a gummy solid on evaporation of appropriate fractions. This was dissolved in ethyl acetate (50 ml) and washed twice with saturated sodium bicarbonate solution(10 ml), once with saturated brine(10 ml), dried (MgSO$_4$) and evaporated to give 1.6 g of a single diastereoisomer of methyl leucine-3-amino-5-hexenate as a pale blue oil. HPLC Dynamax 60A C18 column; acetonitrile/water/0.1%TFA 10–70% over 20 min Rt 10.7 min; 1H NMR (DMSO-d6, 300 MHz, ppm): 0.9(6H, m), 1.4–1.5 (2H, m), 1.5–1.7 (1H, m), 2.1–2.3(2H, m), 2.3–2.5(2H, m), 3.5 (3H, s), 3.6–3.7(1H, m), 4.1–4.2(1H, m), 4.4–4.6 (2H, b), 5.0–5.1 (2H, dd), 5.6–5.8 (1H, m), 8.4 (1H, d): m/Z 257 (M+H).

c) Preparation of 4-(N'-(2-methylphenyl)urea) phenoxyacetyl(methyl leucine-3-amino-5hexenoate) amide This was prepared according to example 1f except methyl leucine-3-amino-5-hexenoate was used in place of methyl methionine-3-amino-3-(3,4-methylenedioxyphenyl) propionate. 4-(N'-(2-methylphenyl)urea)phenoxyacetyl-(methyl leucine-3-amino-5-hexenoate)amide. m/Z 539 (M+H). HPLC Dynamax 60A C18 column; acetonitrile/water/0.1%TFA 10–70% over 20 min Rt 17.7 min (92% pure) used without rigorous drying or further characterisation.

Example 4

Preparation of 4-(N'-(2-methylphenyl)urea)-2-trifluoromethylphenoxyacetyl (leucine-3-amino-3-(3,4-methylenedioxyphenyl)propionic acid)amide This was prepared according to example 1 except 4-(N'-(2-methylphenyl)urea)-2-trifluoromethylphenoxyacetyl (methyl leucine-3-amino-3-(3,4-methylenedioxyphenyl) propionate) amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 9.35 (d, 1H), 8.50 (d, 2H), 8.30 (d, 1H), 7.75 (d, 1H), 7.60 (d, 1H), 7.05–7.30 (m, 4H), 6.90–7.00 (m, 1H), 6.85 (s, 1H), 6.70–6.80 (m, 2H), 5.95 (s, 2H), 4.88–5.00 (m, 1H), 4.65 (s, 2H), 4.24–4.40 (m, 1H), 2.35–2.45 (m, 2H), 2.25 (s, 3H), 1.40–1.60 (m, 3H), 0.70–0.90 (m, 6H); ESPMS (M+H) 673; HPLC-Vydac 201HS54 column acetonitrile/water/0.1%TFA 10%–90% over 20 min Rt 15.94 min.

a) Preparation of t-butyl 4-(N'-(2-methylphenyl) urea)-2-trifluoromethyl phenoxyacetate t-butyl 4-(N'-(2-methylphenyl)urea)-2-trifluoromethylphenoxyacetate was prepared in analogous manner to t-butyl 4-(N'-(2-methylphenyl)urea) phenoxyacetate (see examples 1c and 1d)

1H NMR (DMSO d6, 300 MHz, ppm) 8.28 (d, 2H), 7.75 (d, 1H), 7.60 (d, 1H), 7.04–7.22 (m, 4H), 6.92 (t, 1H), 4.72 (s, 2H), 2.20 (s, 3H), 1.40 (s, 9H); ESPMS (M+H) 425.

b) Preparation of 4-(N'-(2-methylphenyl)urea)-2-trifluoromethyl phenoxyacetic acid This was prepared in an analogous manner to 4-(N'-(2-methylphenyl)urea)phenoxyacetic acid (see example 1e).

1H NMR (DMSO d6, 300 MHz, ppm) 8.30 (d, 2H), 7.75 (d, 1H), 7.60 (d, 1H), 7.04–7.22 (m, 4H), 6.90 (t, 1H), 4.75 (s, 2H), 2.22 (s, 3H)); ESPMS (M–H) 367.

c) Preparation of 4-(N'-(2-methylphenyl)urea)-2-trifluoromethyl phenoxyacetyl (methyl leucine-3-amino-3-(3,4-methylenedioxyphenyl)propionate) amide This was prepared according to example 1f except 4-(N'-(2-methylphenyl)urea)2-trifluoromethylphenoxyacetic acid was used in place of 4-(N'-(2-methylphenyl)urea)-phenoxyacetic acid and methyl leucine-3-amino-3-(3,4-methylenedioxyphenyl)propionate (examples 2a and 2b) was used in place of methyl methionine-3-amino-3-(3,4-methylenedioxyphenyl)propionate.

1H NMR (DMSO d6, 300 MHz, ppm) 8.52 (s, 1H), 8.45 (s, 1H), 8.20 (d, 1H), 7.75 (d, 1H), 7.58 (d, 1H), 7.05–7.22 (m, 5H), 6.86–6.96 (m, 2H), 6.80 (d, 1H), 6.75 (d, 2H), 5.98 (s, 2H), 5.10 (q, 1H), 4.62 (s, 2H), 4.30–4.40 (m, 1H), 3.52 (s, 3H), 2.68–2.78 (m, 2H), 2.20 (s, 3H), 1.30–1.50 (m, 3H), 0.72–0.84 (m, 6H); ESPMS (M+H) 687; HPLC-Dynamax 60A column C18 acetonitrile/water/0.1%TFA 10%–70% over 20 min Rt 20.05 min Example 5

Preparation of 4-(N'-(2-chlorophenyl)urea)-phenoxyacetyl (leucine-3-amino-3-(3,4-methylenedioxyphenyl)propionic acid)amide This was prepared according to example 1 except 4-(N'-(2-chlorophenyl)urea)-phenoxyacetyl (methyl leucine-3-amino-3-(3,4-methylenedioxyphenyl)propionate)amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 9.30 (s, 1H), 8.60 (d, 1H), 8.25 (s, 1H), 8.15 (d, 1H), 7.95 (d, 1H), 7.42 (d, 1H), 7.35 (d, 2H), 7.25 (t, 1H), 7.00 (t, 1H), 6.75–6.92 (m, 4H), 6.70 (d, 1H), 5.95 (s, 2H), 5.05 (q, 1H), 4.50 (s, 2H), 4.30–4.40 (m, 1H), 2.50–2.65 (m, 2H), 1.30–1.50 (m, 3H), 0.70–0.85 (m, 6H); ESPMS (M+H) 625; HPLC-Vydac 201HS54 column acetonitrile/water/0.1%TFA 10%–90% over 20 min Rt 15.07 min.

b) Preparation of t-butyl 4-(N'-(2-chlorophenyl) urea)phenoxyacetate

It was prepared in analogous manner to t-butyl 4-(N'-(2-methylphenyl)urea)phenoxyacetate (see example 1d) using t-butyl 4-nitro-2-chlorophenoxyacetate which was prepared in an analogous manner to t-butyl 4-nitrophenoxyacetate (see example 1c) t-Butyl 4-nitro-2-chlorophenyoxyacetate 1H NMR (CDCl$_3$, 300 MHz, ppm) 8.32 (d, 1H), 8.15 (d, 1H), 6.85 (d, 1H), 4.72 (s, 2H), 1.45 (s, 9H); ESPMS (M+H) 288.

t-Butyl 4-(N'-(2-chlorophenyl)urea)phenoxyacetate: 1H NMR (DMSO d6, 300 MHz, ppm) 9.24 (s, 1H), 8.30–8.40 (m, 2H), 7.60 (d, 1H), 7.55 (d, 2H), 7.45 (t, 1H), 7.20 (t, 1H), 7.20 (t, 1H), 7.05 (d, 2H), 4.75 (s, 2H), 1.60 (s, 9H); ESPMS (M+H) 377.

c) Preparation of 4-(N'-(2-chlorophenyl)urea)-phenoxyacetic acid

It was prepared in an analogous manner to 4-(N'-(2-methylphenyl)urea)phenoxyacetic acid (see example 1e).

1H NMR (DMSO d6, 300 MHz, ppm) 9.20 (s, 1H), 8.20 (s, 1H), 8.15 (d, 1H), 7.40 (d, 1H), 7.35 (d, 2H), 7.25 (t, 1H), 7.00 (t, 1H), 6.82 (d, 2H), 4.60 (s, 2H); ESPMS (M–H) 319 d) Preparation of 4-(N'-(2-chlorophenyl)urea)-phenoxyacetyl (methyl leucine-3-amino-3-(3,4-methylenedioxyphenyl)propionate)amide This was prepared according to example 1f except 4-(N'-(2-chlorophenyl)urea)-phenoxyacetic acid was used in place of 4-(N'-(2-methylphenyl)urea)-phenoxyacetic acid and methyl leucine-3-amino-3-(3,4 methylenedioxyphenyl) propionate (see examples 2a and 2b) was used in place of methyl methionine-3-amino-3-(3,4-methylenedioxyphenyl) propionate.

1H NMR (DMSO d6, 300 MHz, ppm) 9.20 (s, 1H), 8.45 (d, 1H), 8.20 (s, 1H), 8.15 (d, 1H), 7.95 (d, 1H), 7.42 (d, 1H), 7.35 (d, 2H), 7.25 (t, 1H), 7.00 (t, 1H), 6.85–6.95 (m, 3H), 6.80 (d, 1H), 6.75 (d, 1H), 5.98 (s, 2H), 5.10 (q, 1H), 4.45 (s, 2H), 4.30–4.40 (m, 1H), 3.50 (s, 3H), 2.70–2.76 (m, 2H), 1.30–1.50 (m, 3H), 0.70–0.85 (m, 6H); ESPMS (M+H) 639; HPLC-Dynamax 60A column C18 acetonitrile/water/ 0.1%TFA 20%–80% over 20 min Rt 16.71 min.

Example 6

Preparation of 4-(N'-(2-bromophenyl)urea)-phenoxyacetyl (leucine-3-amino-3-(3,4-methylenedioxyphenyl)propionic acid)amide This was prepared according to example 1 except 4-(N'-(2-bromophenyl)urea)-phenoxyacetyl (methyl leucine-3-amino-3-(3,4-methylenedioxyphenyl)propionate)amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 9.38 (s, 1H), 8.62 (d, 1H), 8.10 (s, 1H), 8.05 (d, 1H), 7.95 (d, 1H), 7.60 (d, 1H), 7.25–7.40 (m, 3H), 6.70–7.00 (m, 6H), 5.95 (s, 2H), 5.05 (q, 1H), 4.45 (s, 2H), 4.30–4.40 (m, 1H), 2.50–2.65 (m, 2H), 1.30–1.50 (m, 3H), 0.70–0.85 (m, 6H); ESPMS (M+H) 671; HPLC-Vydac 201HS54 column acetonitrile/water/0.1%TFA 10%–90% over 20 min Rt 14.85 min.

a) Preparation of t-butyl 4-(N'-(2-bromophenyl) urea)-phenoxyacetate

It was prepared in an analogous manner to t-butyl 4-(N'-(2-methylphenyl)urea)phenoxyacetate (see examples 1c and 1d).

1H NMR (DMSO d6, 300 MHz, ppm) 9.15 (s, 1H), 7.88–7.95 (m, 2H), 7.45 (d, 1H), 7.15–7.25 (m, 3H), 6.78–6.88 (m, 1H), 6.68–6.75 (m, 2H), 4.45 (s, 2H), 1.30 (s, 9H); ESPMS (M+H) 423 b) Preparation of 4-(N'-(2-bromophenyl)urea)-phenoxyacetic acid

It was prepared in an analogous manner to 4-(N'-(2-methylphenyl)urea)phenoxyacetic acid in (example 1e).

1H NMR (DMSO d6, 300 MHz, ppm) 9.25 (s, 1H), 8.00–8.10 (m, 2H), 7.58 (d, 1H), 7.25–7.38 (m, 3H), 6.90–6.98 (m, 1H), 6.80–6.88 (m, 2H), 4.60 (s, 2H); ESPMS (M+H) 365 c) Preparation of 4-(N'-(2-bromophenyl)urea)-phenoxyacetyl (methyl leucine-3-amino-3-(3,4-methylenedioxyphenyl)propionate)amide This was prepared according to example 1f except 4-(N'-(2-bromophenyl)urea)-phenoxyacetic acid was used in place of 4-(N'-(2-methylphenyl)urea)-phenoxyacetic acid and methyl leucine-3-amino-3-(3,4 methylenedioxyphenyl) propionate (see examples 2a and 2b) was used in place of methyl methionine-3-amino-3-(3,4-methylenedioxyphenyl) propionate.

1H NMR (DMSO d6, 300 MHz, ppm) 9.28 (s, 1H), 8.45 (d, 1H), 8.00–8.10 (m, 2H), 7.95 (d, 1H), 7.58 (d, 1H), 7.25–7.40 (m, 3H), 6.85–6.95 (m, 4H), 6.8 (d, 1H), 6.72 (d, 1H), 5.98 (s, 2H), 5.10 (q, 1H), 4.44 (s, 2H), 4.35 (q, 1H), 3.50 (s, 3H), 2.70–2.78 (m, 2H), 1.30–1.50 (m, 3H), 0.75–0.85 (m, 6H); ESPMS (M+H) 683; HPLC-Dynamax 60A column C18 acetonitrile/water/0.1%TFA 20%–80% over 20 min Rt 16.87 min.

Example 7

Preparation of 4-(N'-(2-methylphenyl)urea)-3-chlorophenoxyacetyl (leucine-3-amino-3-(3,4-methylenedioxyphenyl)propionic acid)amide This was prepared according to example 1 except 4-(N'-(2-methylphenyl)urea-3-chlorophenoxyacetyl (methyl leucine-3-amino-3-(3,4-methylenedioxyphenyl)-propionate)amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 9.80 (s, 1H), 8.98 (d, 1H), 8.60 (s, 1H), 7.98 (d, 1H), 7.75 (s, 1H), 7.65 (d, 1H), 7.20 (d, 1H), 7.04–7.15 (m, 2H), 6.85–7.00 (m, 2H), 6.82 (s, 1H), 6.70–6.80 (m, 2H), 5.90 (s, 2H), 5.00 (q, 1H), 4.58 (s, 2H), 4.35 (q, 1H), 2.20 (s, 3H), 1.38–1.55 (m, 3H), 0.70–0.90 (m, 6H); ESPMS (M+H) 639; HPLC-Vydac 201HS54 column acetonitrile/water/0.1%TFA 10%–90% over 20 min Rt 14.97 min.

a) Preparation of t-butyl 4-(N'-(2-methylphenyl) urea)-3-chlorophenoxyacetate

It was prepared in analogous manner to t-butyl 4-(N'-(2-methylphenyl)urea)phenoxyacetate (see examples 1c and 1d).

1H NMR (DMSO d6, 300 MHz, ppm) 8.95 (s, 1H), 7.85 (s, 1H), 7.76 (d, 1H), 7.65 (d, 1H), 7.05–7.20 (m, 3H), 6.88–6.95 (m, 2H), 4.65 (s, 2H), 2.20 (s, 3H), 1.40 (s, 9H); ESPMS (M+H) 391.

b) Preparation of 4-(N'-(2-methylphenyl)urea)-3-chlorophenoxyacetic acid

It was prepared in an analogous manner to 4-(N'-(2-methylphenyl)urea)phenoxyacetic acid (see example 1e).

1H NMR (DMSO d6, 300 MHz, ppm) 8.95 (s, 1H), 7.85 (s, 1H), 7.78 (d, 1H), 7.68 (d, 1H), 7.08–7.20 (m, 3H), 6.88–7.00 (m, 2H), 4.70 (s, 2H), 2.20 (s, 3H); ESPMS (M+H) 335.

c) Preparation of 4-(N'-(2-methylphenyl)urea)-3-chlorophenoxyacetyl (methyl leucine-3-amino-3-(3, 4-(methylenedioxyphenyl)propionic)amide This was prepared according to example 1f except 4-(N'-(2-methylphenyl)urea)-3-chlorophenoxyacetic acid was used in place of 4-(N'-(2-methylphenyl)urea)-phenoxyacetic acid and methyl leucine-3-amino-3-(3,4 methylenedioxyphenyl)propionate (see examples 2a and 2b) was used in place of methyl methionine-3-amino-3-(3,4-methylenedioxyphenyl)propionate.

1H NMR (DMSO d6, 300 MHz, ppm) 9.05 (s, 1H), 8.55 (d, 1H), 7.98 (s, 1H), 7.85 (d, 1H), 7.75 (d, 1H), 7.70 (d, 1H), 7.05–7.20 (m, 3H), 6.90–7.00 (m, 2H), 6.85 (s, 1H), 6.80 (d, 1H), 6.75 (d, 1H), 5.95 (s, 2H), 5.10 (q, 1H), 4.60 (s, 2H), 4.35 (q, 1H), 3.50 (s, 3H), 2.68–2.76 (m, 2H), 2.20 (s, 3H), 1.35–1.45 (m, 3H), 0.75–0.85 (m, 6H); ESPMS (M+H) 653; HPLC-Dynamax 60A column acetonitrile/water/ 0.1%TFA 10%–70% over 20 min Rt 20.45 min.

Example 8

Preparation of 4-(N'-(2-methyl-4-chlorophenyl) urea)-phenoxyacetyl (leucine-3-amino-3-(3,4-methylenedioxyphenyl)propionic acid)amide This was prepared according to example 1 except 4-(N'-(2-methyl-4-chlorophenyl)urea)-phenoxyacetyl (methyl leucine-3-amino-3-(3,4-methylenedioxyphenyl)propionate) amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 10.15 (s, 1H), 9.50–9.60 (m, 1H), 9.10 (s, 1H), 8.25 (d, 1H), 7.90 (d, 2H), 7.60 (d, 1H), 7.30–7.40 (m, 2H), 6.95–7.05 (m, 3H), 6.90 (s, 2H), 6.10 (d, 2H), 5.08–5.18 (m, 1H), 4.65 (s, 2H), 4.42–4.52 (m, 1H), 2.55 (d, 2H), 2.40 (s, 3H), 1.60–1.70 (m, 3H), 0.90–1.10 (m, 6H); ESPMS (M+H) 639; HPLC-Vydac 201HS54 column acetonitrile/water/0.1%TFA 10%–90% over 20 min Rt 15.14 min.

a) Preparation of t-butyl 4-(N'-(2-methyl-4-chlorophenyl)urea)-phenoxyacetate

It was prepared in analogous manner to t-butyl 4-(N'-(2-methylphenyl)urea)phenoxyacetate (see examples 1c and 1d).

1H NMR (DMSO d6, 300 MHz, ppm) 8.82 (s, 1H), 7.82–7.90 (m, 2H), 7.32 (d, 2H), 7.22 (s, 1H), 7.15 (d, 1H), 6.80 (d, 2H), 4.56 (s, 2H) 2.20 (s, 3H); ESPMS (M+H) 391.

b) Preparation of 4-(N'-(2-methyl-4-chlorophenyl)urea)-phenoxyacetic acid

It was prepared in an analogous manner to 4-(N'-(2-methylphenyl)urea)phenoxyacetic acid (see example 1e).

1H NMR (DMSO d6, 300 MHz, ppm) 8.84 (s, 1H), 7.82–7.90 (m, 2H), 7.32 (d, 2H), 7.22 (s, 1H), 7.15 (d, 1H), 6.82 (d, 2H), 4.60 (s, 2H) 2.20 (s, 3H); ESPMS (M–H) 335 c) Preparation of 4-(N'-(2-methyl-4-chlorophenyl)urea)-phenoxyacetyl (methyl leucine-3-amino-3-(3,4-methylenedioxyphenyl)propionate)amide This was prepared according to example 1f except 4-(N'-(2-methyl-4-chlorophenyl)urea)-phenoxyacetic acid was used in place of 4-(N'-(2-methylphenyl)urea)-phenoxyacetic acid and methyl leucine-3-amino-3-(3,4 methylenedioxyphenyl)propionate (see examples 2a and 2b) was used in place of methyl methionine-3-amino-3-(3,4-methylenedioxyphenyl)propionate. It gave 4-(N'-(2-methyl-4-chlorophenyl)urea)-phenoxyacetyl (methyl leucine-3-amino-3-(3,4-methylene dioxyphenyl)propionate)amide.

1H NMR (DMSO d6, 300 MHz, ppm) 9.15 (s, 1H), 8.50 (d, 1H), 8.15 (s, 1H), 7.95 (d, 1H), 7.82 (d, 1H), 7.38 (d, 2H), 7.20 (s, 1H), 7.15 (d, 1H), 6.70–6.90 (m, 5H), 5.98 (s, 2H), 5.10 (q, 1H), 4.45 (s, 2H), 4.35 (q, 1H), 3.50 (s, 3H), 2.68–2.78 (m, 2H), 2.20 (s, 3H), 1.30–1.50 (m, 3H), 0.70–0.90 (m, 6H); ESPMS (M+H) 653; HPLC-Dynamax 60A column C18 acetonitrile/water/0.1%TFA 10%–70% over 20 min Rt 20.53 min.

Example 9

Preparation of 4-(N'-(2-methylphenyl)urea)-2-methylphenoxyacetyl (leucine-3-amino-3-(3,4-(methylenedioxyphenyl)propionic This was prepared according to example 1 except 4-(N'-(2-methylphenyl)urea)-2-methylphenoxyacetyl (methyl leucine-3-amino-3-(3,4-methylene dioxyphenyl)propionate) amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 8.90–9.00 (m, 1H), 8.20 (s, 1H), 8.08 (s, 1H), 7.85 (d, 1H), 7.60 (d, 1H), 7.30 (d, 1H), 6.90–7.04 (m, 2H), 6.50–6.80 (m, 6H), 5.78 (s, 2H), 4.72–4.88 (m, 1H), 4.35 (s, 2H), 4.20–4.42 (m, 1H), 2.00–2.15 (m, 6H), 1.25–1.42 (m, 3H), 0.60–0.80 (m, 6H); ESPMS (M+H) 619; HPLC-Vydac 201HS54 column acetonitrile/water/0.1%TFA 10%–90% over 20 min Rt 14.70 min.

a) Preparation of t-butyl 4-(N'-(2-methylphenyl) urea)-2-methyl phenoxyacetate

It was prepared in analogous manner to t-butyl 4-(N'-(2-methylphenyl)urea)phenoxyacetate (see examples 1c and 1d).

1H NMR (DMSO d6, 300 MHz, ppm) 8.10 (s, 2H), 8.00 (s, 1H), 7.78 (d, 1H), 7.50 (d, 1H), 7.04–7.18 (m, 2H), 6.90 (t, 1H), 6.75 (s, 1H), 6.65 (d, 1H), 4.58 (s, 2H), 2.20 (d, 6H), 1.40 (s, 9H); ESPMS (M+H) 371.

b) Preparation of 4-(N'-(2-methylphenyl)urea)-2-methylphenoxyacetic acid

It was prepared in an analogous manner to 4-(N'-(2-methylphenyl)urea)phenoxyacetic acid in (see example 1e).

1H NMR (DMSO d6, 300 MHz, ppm) 8.10 (s, 2H), 8.00 (s, 1H), 7.75–7.82 (m, 1H), 7.44–7.52 (m, 1H), 7.04–7.20 (m, 2H), 6.84–6.95 (m, 1H), 6.75 (s, 1H), 6.62–6.70 (m, 1H), 4.60 (s, 2H), 2.20 (d, 6H); ESPMS (M–H) 313 c) Preparation of 4-(N'-(2-methylphenyl)urea)-2-methylphenoxyacetyl (methyl leucine-3-amino-3-(3,4-methylenedioxyphenyl)propionate)amide This was prepared according to example 1f except 4-(N'-(2-methylphenyl)urea)-2-methylphenoxyacetic acid was used in place of 4-(N'-(2-methylphenyl)urea)-phenoxyacetic acid and methyl leucine-3-amino-3-(3,4 methylenedioxyphenyl)propionate (see examples 2a and 2b) was used in place of methyl methionine-3-amino-3-(3,4-methylenedioxyphenyl)propionate.

1H NMR (DMSO d6, 300 MHz, ppm) 8.50 (d, 1H), 8.18 (s, 1H), 8.05 (s, 1H), 7.95 (d, 1H), 7.78 (d, 1H), 7.50 (d, 1H), 7.05–7.18 (m, 2H), 6.82–6.95 (m, 2H), 6.70–6.92 (m, 4H), 5.98 (s, 2H), 5.10 (q, 1H), 4.50 (s, 2H), 4.30–4.40 (m, 1H), 3.50 (s, 3H), 2.70–2.78 (m, 2H), 2.20 (d, 6H), 1.30–1.50 (m, 3H), 0.72–0.88 (m, 6H); ESPMS (M+H) 633; HPLC-Dynamax 60A column C18 acetonitrile/water/0.1%TFA 10%–70% over 20 min Rt 18.99 min.

Example 10

Preparation of 4-(N'-(2,4-dichlorophenyl)urea)-phenoxyacetyl (leucine-3-amino-3-(3,4-methylenedioxyphenyl)propionic acid)amide This was prepared according to example 1 except 4-(N'-(2,4-dichlorophenyl)urea)phenoxyacetyl (methyl leucine-3-amino-3-(3,4-methylenedioxyphenyl)propionate)amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 9.70 (s, 1H), 9.15 (d, 1H), 8.68 (s, 1H), 7.95–8.10 (m, 2H), 7.50 (d, 1H), 7.25–7.35 (m, 3H), 6.75–6.85 (m, 3H), 6.65–6.72 (m, 2H), 5.88 (s, 2H), 4.85–4.95 (m, 1H), 4.45 (s, 2H), 4.20–4.35 (m, 1H), 2.33–2.40 (m, 2H), 1.35–1.50 (m, 3H), 0.70–0.85 (m, 6H); ESPMS (M+H) 661; HPLC-Vydac 201HS54 column acetonitrile/water/0.1%TFA 10%–90% over 20 min Rt 15.96 min.

a) Preparation of t-butyl 4-(N'-(2,4-dichlorophenyl)urea)-phenoxyacetate

It was prepared in analogous manner to t-butyl 4-(N'-(2-methylphenyl)urea)phenoxyacetate (see examples 1c and 1d).

1H NMR (DMSO d6, 300 MHz, ppm) 9.20 (s, 1H), 8.25 (s, 1H), 8.15 (d, 1H), 7.50–7.60 (m, 1H), 7.22–7.38 (m, 3H), 6.80 (d, 2H), 4.56 (s,2H), 1.38 (s,9H); ESPMS (M+H) 411.

b) Preparation of 4-(N'-(2,4-dichlorophenyl)urea)-phenoxyacetic acid

It was prepared in an analogous manner to 4-(N'-(2-methylphenyl)urea)phenoxyacetic acid in example 1e.

1H NMR (DMSO d6, 300 MHz, ppm) 9.22 (s, 1H), 8.30 (s, 1H), 8.18 (d, 1H), 7.58 (s, 1H), 7.24–7.40 (m, 3H), 6.80–6.90 (m, 2H), 4.58 (s, 2H); ESPMS (M–H) 353 c) Preparation of 4-(N'-(2,4-dichlorophenyl)urea)-phenoxyacetyl (methyl leucine-3-amino-3-(3,4-methylenedioxyphenyl)propionate)amide This was prepared according to example 1f except 4-(N'-(2,4-dichlorophenyl)urea)-phenoxyacetic acid was used in place of 4-(N'-(2-methylphenyl)urea)-phenoxyacetic acid and methyl leucine-3-amino-3-(3,4 methylenedioxyphenyl) propionate (see examples 2a and 2b) was used in place of methyl methionine-3-amino-3-(3,4-methylenedioxyphenyl) propionate. It gave 4-(N'-(2,4-dichlorophenyl)urea)-phenoxyacetyl (methyl leucine-3-amino-3-(3,4-methylene dioxyphenyl)propionate)amide.

1H NMR (DMSO d6, 300 MHz, ppm) 9.30 (s, 1H), 8.50 (d, 1H), 8.30 (s, 1H), 8.18 (d, 1H), 7.94 (d, 1H), 7.58 (s, 1H), 7.30 (d, 3H), 6.68–6.95 (m, 5H), 5.94 (s, 2H), 5.10 (q, 1H), 4.50 (s, 2H), 4.30–4.40 (m, 1H), 3.52 (s, 3H), 2.62–2.82 (m, 2H), 1.30–1.50 (m, 3H), 0.70–0.90 (m, 6H); ESPMS (M+H) 675; HPLC-Dynamax 60A column C18 acetonitrile/water/0.10/TFA 10%–70% over 20 min Rt 21.90 min Example 11

Preparation of 4-(N'-(2-methylphenyl)urea)-3-chlorophenoxyacetyl (methionine-3-amino-3-(3,4-methylenedioxyphenyl)propionic acid)amide This was prepared according to example 1 except 4-(N'-(2-methylphenyl)urea)-3-chlorophenoxyacetyl (methyl methionine-3-amino-3-(3,4-methylenedioxyphenyl) propionate)amide was used in place of 4-(N'-(2-methylphenyl)urea)-phenoxyacetyl (methyl methionine-3-amino-3-(3,4-methylenedioxyphenyl)propionate)amide.

1H NMR (DMSO d6, 300 MHz, ppm) 8.95 (s, 1H), 8.50 (d, 1H), 7.98 (d, 1H), 7.85 (s, 1H), 7.75 (d, 1H), 7.68 (s, 1H), 7.05–7.20 (m, 3H), 6.98 (d, 1H), 6.90 (t, 1H), 6.82 (s, 1H), 6.80 (d, 1H), 6.75 (d, 1H), 5.95 (s, 2H), 5.05 (q, 1H), 4.60 (s, 2H), 4.40 (q, 1H), 2.60–2.75 (m, 2H), 2.15–2.30 (m, 5H), 1.95 (s, 3H), 1.70–1.90 (m, 2H); ESPMS (M+H) 657; HPLC-Dynamax 60A column C18 acetonitrile/water/ 0.1%TFA 10%–70% over 20 min Rt 17.43 min.

a) Preparation of 4-(N'-(2-methylphenyl)urea)-3-chlorophenoxyacetyl (methyl methionine-3-amino-3-(3,4-methylenedioxyphenyl)propionate)amide This was prepared according to example 1f except 4-(N'-(2-methylphenyl)urea)3-chlorophenoxyacetic acid (see examples 7a and 7b) was used in place of 4-(N'-(2-methylphenyl)urea)-phenoxyacetic acid.

1H NMR (DMSO d6, 300 MHz, ppm) 8.98 (s, 1H), 8.52 (d, 1H), 8.00 (d, 1H), 7.85 (s, 1H), 7.75 (d, 1H), 7.68 (d, 1H), 7.05–7.20 (m, 3H), 6.98 (d, 1H), 6.92 (t, 1H), 6.85 (s, 1), 6.80 (d, 1H), 6.75 (d, 1H), 5.96 (s, 2H), 5.10 (q, 1H), 4.60 (s, 2H), 4.40 (q, 1H), 3.52 (s, 3H), 2.70–2.78 (m, 2H), 2.25 (t, 2H), 2.20 (s, 3H), 1.94 (s, 3H), 1.70–1.90 (m, 2H); ESPMS (M+H) 671; HPLC-Dynamax 60A column C18 acetonitrile/water/0.1%TFA 10%–70% over 20 min Rt 19.47 min.

Example 12

Preparation of 4-(N'-(2-methylphenyl)urea) phenthioacetyl (leucine-3-amino-(3,4-methylenedioxy)phenylpropionic acid)amide A mixture of (4-(N'-(2-methylphenyl)urea)phenthioacetyl (leucine-3-amino-(3,4-methylenedioxy)phenylpropionate) amide (150 mg), MeOH(5 ml), THF(2 ml) and 2N NaOH(2 ml) was stirred at 50° C. for 2 h then acidified with HOAc. The mixture was concentrated to ca. 3 ml under vacuum then diluted with water and the insoluble solid collected and washed with water and EtOAc to give 4-(N'-(2-methylphenyl)urea)phenthioacetyl (leucine-3-amino-(3,4-methylenedioxy)phenylpropionic acid)amide(110 mg,74%), mp207–210° C. 1HNMR (d6-DMSO, 300 MHz, ppm): 9.05 (s,1H); 8.4 (d,1H); 8.05 (d,1H); 7.9 (s,1H); 7.8 (d,1H); 7.4 (d,2H); 7.3 (d,2H); 7.1 (m,2H); 6.95 (m,1H); 6.7–6.9 (m,3H); 5.95 (s,2H); 5.05(m,1H); 4.25(m,1H); 3.6(dd,2H); 2.6(m,2H); 2.2(s,3H); 1.2–1.4(m,3H); 0.75(m,6H). MS: (ES–) m/e 619.5(MH)– a) Preparation of 4-N'-(2-methylphenyl)urea) phenylthioacetic acid

A suspension of 2-(4-aminophenylthio)acetic acid (3.07 g) in acetonitrile(120 ml) was stirred at reflux while adding 2-methylphenyl isocyanate(2.1 ml) and the mixture was stirred at reflux for 1 h. The resulting solution was cooled and the pale grey solid which crystallised was collected to give 4-N'-(2-methylphenyl)urea)phenylthioacetic acid(4.93 g,93%),mp182–183° C.

b) Preparation of (4-(N'-(2-methylphenyl)urea) phenthioacetyl (leucine-3-amino-(3,4-methylenedioxy)phenylpropionate)amide A mixture of 4-N'-(2-methylphenyl)urea)phenylthioacetic acid(364 mg), DMF(7 ml), methyl-2-(1,3-benzodioxol-5-yl)-2-(leucinylamino)propionate (336 mg),1-hydroxybenotriazole(156 mg), 1-(3-dimethylaminopropyl)-3-ethylcarbodiimide hydrochloride(220 mg) and N-methylmorpholine(116 mg) was stirred at room temperature for 4 days. The mixture was diluted with EtOAc and water and the precipitate collected and washed with water and EtOAC to give (4-(N'-(2-methylphenyl)urea) phenthioacetyl (leucine-3-amino-(3,4-methylenedioxy) phenylpropionate)amide(500 mg,79%) as an off-white solid.

Examples 13 to 76 were prepared as described below and in Table 1.

Example 14

Preparation of 4-(N'-(2-methylphenyl)urea) phenylsulphonylacetyl (leucine-3-amino-(3,4-methylenedioxy)phenylpropionic acid)amide This was prepared according to example 1 except that methyl-2-(1,3-benzodioxol-5-yl)-2-(2-{[4-(2-methylphenylureido)phenylsulphonyl]acetyl leucinylamino}propionate was used in place of 4-(N'-(2-methylphenyl)urea)phenoxyacetyl (methyl methionine-3-amino-3-(3,4-methylenedioxyphenyl)propionate)amide.

a) Preparation of methyl-2-(1,3-benzodioxol-5-yl)-2-(2-{[4-(2-methylphenylureido)phenylsulphonyl] acetyl leucinylamino}propionate A mixture of methyl-2-(1,3-benzodioxol-5-yl)-2-(2-{[4-(2-methylphenylureido) phenylthio]acetyl leucinylamino}propionate(Example 12 b 0.35 g), DMF(2 ml), methanol(8 ml), Oxone®(1 g) and water(4 ml) was stirred at room temperature for 24 hr. The mixture was diluted with water and extracted with ethyl acetate and the organic phase was dried and evaporated to dryness. The residue was triturated with ether and the insoluble solid collected to give methyl-2-(1,3-benzodioxol-5-yl)-2-(2-{[4-(2-methylphenylureido)phenylsulphonyl]acetyl leucinylamino}propionate(0.32 g). [m/e 667 (M+H)$^+$]

Example 16

Preparation of 2-(4-(N'-(2-methylphenyl)urea) phenoxy)butyryl (leucine-3-amino-(3,4-methylenedioxy)phenylpropionic acid)amide This was according to example 2 except that in 2c and 1f 2-(N'-(2-methylphenyl)urea)-phenoxy)butyric acid was used in place of 4-(N'-(2-methylphenyl)urea)-phenoxyacetic acid.

a) Preparation of ethyl 2-(4-(N'-(2-methylphenyl) urea)-phenoxy)butyrate

Potassium carbonate (5.5 g, 0.04 mole) was added to a stirred solution of 4-nitrophenol (5.56 g,0.04 mole) in DMF (20 ml). Ethyl 2-bromobutyrate (7.8 g, 0.04 mole) was then added and the mixture stirred for 48 hrs. At ambient temperature. The mixture was poured into water (60 ml) and extracted with diethyl ether (2 times 70 ml). The organic phase was separated, washed with brine, dried and evaporated to dryness to give an oil (9 g). 10% Pd/C (0.2 g) was added to this oil (2 g. 0.008 mole) in ethanol (20 ml) and the mixture stirred under hydrogen for 2 hr, filtered and evaporated to dryness. The residue in dichloromethane (20 ml) was treated with 2-methylphenylisocyanate (1.05 g, 0.008 mole) and the mixture allowed to stand for 18 hr. The solution was filtered and evaporated to dryness and the residue recrystallised from ethanol to give product (1.3 g).

1H NMR (DMSO d6, 300 MHz, ppm); 1.0 (t), 3H; 1.2 (t), 3H; 2.2 (s), 3H; 4.1 (q), 2H; 4.65 (t), 1H; 6.8 (d), 2H; 6.9 (t), 1H; 7.1 (m), 2H; 7.35 (d), 2H; 7.8 (m), 2H, 8.8 (s), 1H ESPMS (M+H) 357 b) Preparation of 2-(4-(N'-(2-methylphenyl)urea)-phenoxy)butyric acid

2M Aqueous sodium hydroxide solution (3 ml) was added to ethyl 2-(4-(N'-(2-methylphenyl)urea)-phenoxy)butyrate (1.2 g, 0.0034 mole) in dimethyl sulphoxide (7 ml) the mix stirred for 1 hr at ambient temperature. Water (10 ml) added and the pH adjusted to ~2 with 2N hydrochloric acid and the product filtered, washed with water and dried to give product (1.0 g).

1H NMR (DMSO d6, 300 MHz, ppm); 1.0 (t), 3H; 2.2 (s), 3H; 4.5 (t), 1H; 6.8 (d), 2H; 6.9 (t), 1H; 7.1 (m), 2H; 7.35 (d), 2H; 7.8 (m), 2H, 8.8 (s), 1H 1H ESPMS (M–H) 327.

Example 23

Preparation of 4-(2-methylphenylureido)-phenylacetylamino-(2-[methylsulphonylethyl] glycinyl)aspartic acid-α-(2,dimethylpentyl)ester A mixture of 4-(2-methylphenylureido)-phenylacetylamino-S-(2-[methylsulphonylethyl]glycinyl) aspartic acid-α-(2,5-dimethylpentyl)-β-benzyl diester(65 mg), DMF(5 ml) and 10% Pd on carbon catalyst (20 mg) was stirred under hydrogen at room temperature and atmospheric pressure for 4 hr. The mixture was filtered, the filtrate evaporated to dryness and the residue triturated with ethyl acetate to give 2-(2-phenylamino-benzoxazol-6-yl)-acetylamino-(2-[methylsulphonylethyl]glycinyl)-aspartic acid-α-(2,5-dimethylpentyl)ester(52 mg, 91%) as an off white solid.

a) Preparation of BOC-aspartic acid-α-(2,5-dimethylpentyl)-β-benzyl diester

A mixture of BOC-aspartic acid-β-benzyl ester(3.23 g), dichloromethane(20 ml), 2,4-dimethylpentanol (1.51 g) and dicyclohexylcarbodiimide(2.06 g) was stirred and treated with 4-dimethylaminopyridine(20 mg). The mixture was stirred for 1 hr, filtered and the filtrate was evaporated to dryness. The residue was purified by flash chromatography on silica using an increasingly polar mixture of dichloromethane and ethyl acetate and the appropriate fractions combined and evaporated to dryness to give product as a gum (3.55 g). [m/e422 (MH)$^+$]

b) Preparation of aspartic acid-α-(2,5-dimethylpentyl)-β-benzyl diester

A solution of BOC-aspartic acid-α-(2,5-dimethylpentyl)-β-benzyl diester(3.4 g) in dichloromethane(10 ml) was treated with trifluoroacetic acid (10 ml) and the mixture was stirred at room temperature for 2 hours then evaporated to dryness. The residue was stied with a mixture of water(10 ml) and ethyl acetate(30 ml) and basified with potassium hydrogen carbonate. The organic phase was separated, washed with brine, dried and evaporated to dryness to give aspartic acid-α-(2,5-dimethylpentyl)-β-benzyl diester as a gum (2.7 g). [m/e322 (MH)$^+$]

c) Preparation of BOC-methioninyl-aspartic acid-α-(2,5-dimethylpentyl)-β-benzyl diester A mixture of aspartic acid-α-(2,5-dimethylpentyl)-β-benzyl diester (0.64 g), BOC-methionine (0.75 g), hydroxybenzotriazole (0.41 g), N-methylmorpholine(1 ml), dichloromethane (10 ml) and 1-(3-dimethylamninopropyl)-3-ethylcarbodiimide hydrochloride(0.57 g) was stirred for 18 hr. The mixture was diluted to 30 ml with dichloromethane and the solution was washed successively with aqueous sodium hydrogen carbonate solution (2 times) and brine and then dried and evaporated to dryness to give BOC-methioninyl-aspartic acid-α-(2,5-dimethylpentyl)-β-benzyl diester as a gum(1.15 g) which was used without further purification.

d) Preparation of methioninyl-aspartic acid-α-(2,5-dimethylpentyl)-β-benzyl diester A mixture of BOC-methioninyl-aspartic acid-α-(2,5-dimethylpentyl)-β-benzyl diester(1 g), dichloromethane(5 ml), triethylsilane(0.5 ml) and trifluoroacetic acid(5 ml) was stirred at room temperature for 1 hr then evaporated to dryness. The residue was partitioned between aqueous potassium carbonate solution and ethyl acetate and the organic phase was separated, dried and evaporated to dryness. The residue was purified by flash chromatography eluting with a 1% solution of triethylamine in ethyl acetate to give methioninyl-aspartic acid-α-(2,5-dimethylpentyl)-β-benzyl diester as a gum(0.32 g) [m/e 453 (MH)$^+$]

e) Preparation of 4-(2-methylphenylureido)-phenylacetylamino-methioninyl-aspartic acid-α-(2,5-dimethylpentyl)-β-benzyl diester A mixture of methioninyl-aspartic acid-α-(2,5-dimethylpentyl)-β-benzyl diester(0.3 g), 4-(2-methylphenylureido)phenylacetic acid(0.28 g), hydroxybenzotriazole(0.13 g), N-methylmorpholine(0.1 ml), dichloromethane(5 ml) and 1-(3-dimethylaminopropyl)-3-ethylcarbodiimide hydrochloride (0.19 g) was stirred for 18 hr. The mixture was diluted with ethyl acetate and washed successively with 1N hydrochloric acid, 1N sodium hydroxide and brine, then dried and evaporated to dryness. The residue was triturated with ethyl acetate to give 4-(2-methylphenylureido)-phenylacetylamino-methioninyl-aspartic acid-α-(2,5-dimethylpentyl)-β-benzyl diester as a white solid (0.4 g). [m/e719 (MH)$^+$]

f) Preparation of 4-(2-methylphenylureido)-phenylacetylamino-(2-[methylsulphonylethyl]glycinyl)aspartic acid-α-(2,5-dimethylpentyl)-β-benzyl diester A mixture of 4-(2-methylphenylureido)-phenylacetylamino-methioninyl-aspartic acid-α-(2,5-dimethylpentyl)-β-benzyl diester(0.12 g), DMF(1 ml), Oxone®[Aldrich](0.25 g) and water(0.5 ml) was stirred at room temperature for 72 hr. The mixture was diluted with water and the insoluble solid collected to give 4-(2-methylphenylureido)-phenylacetylamino-(2-[methylsulphonylethyl]glycinyl)aspartic acid-α-(2,5-dimethylpentyl)-β-benzyl diester(0.11 g) as a white solid. [m/e719 (MH)$^+$]

Example 28

Preparation of 6-(N'-(2-methylphenyl)urea)chroman-2-carboxyl (leucine-3-amino-(3,4-methylenedioxy)phenylpropionic acid)amide This was prepared according to example 2 except that in 2c and 1f 6-(N'-(2-methylphenyl)urea)chroman-2-carboxylic acid was used in place of 4-(N'-(2-methylphenyl)urea)phenoxyacetic acid.

a) Preparation of ethyl 2-(4-(N'-(2-methylphenyl)urea)chroman-2-carboxylate.

2-Methylphenylisocyanate (0.32 g, 0.0024 mole) was added to a stirred solution of ethyl 6-aminochrom-4-one-2-carboxylate (0.5 g, 0.0022 mol), prepared as described in Barker, G.; Ellis, G. P.; J Chem Soc C, 1970, 2230, (incorporated herein by reference) in THF (5 ml) at ambient temperature. The mixture was stirred for 18 hr and the product recovered by filtration, washed with ether to give 0.64 g which was hydrogenated in a mixture of N-methylpyrollidinone (20 ml) and acetic acid (20 ml) at 60° C. in the presence of Pd/C catalyst (0.4 g) for 10 hr, filtered and evaporated to dryness and the residue triturated with water. The solid residue was dried to give the product ethyl 2-(4-(N'-(2-methylphenyl)urea)chroman-2-carboxylate (0.45 g).

NMR (DMSO d6, 300 MHz, ppm); 1.2(t), 3H; 2.1 (m), 2H; 2.2 (s), 3H; 2.7 (m),2H; 4.1 (q), 2H; 4.8 (m), 1H; 6.7 (d),1H; 6.9 (t), 1H; 7.1 (m), 4H; 7.8 (m), 2H; 8.7 (s), 1H. ESPMS (M+H) 355 b) Preparation of 6-(N'-(2-methylphenyl)urea)chroman-2-carboylic acid

Ethyl 2-(4-(N'-(2-methylphenyl)urea)chroman-2-carboxylate (0.43 g, 0.0012 mole) in dimethyl sulphoxide (5 ml) was treated with aqueous sodium hydroxide (1.2 ml) and the mix stirred for 2 hrs, water (10 ml) added and the pH adjusted to ~2 with 2N. hydrochloric acid. The product was filtered off, washed with water and air dried to give the above (0.35 g).

NMR (DMSO d6, 300 MHz, ppm); 2.1(m), 2H; 2.2 (s),3H; 2.7 (m), 2H; 4.7 (m), 1H; 6.7 (d), 1H; 6.9 (t), 1H; 7.1 (m), 4H, 7.8 (m), 2H; 8.7 (s), 1H. ESPMS (M+H)327.

Example 29

Preparation of 4-(N'-(2-thienyl)urea)phenoxyacetyl (leucine-3-amino-(3,4-methylenedioxy)phenylpropionic acid)amide This was prepared according to example 1 except that 4-(N'-(2-thienyl)urea)phenoxyacetyl (methyl leucine-3-amino-(3,4-methylenedioxy)phenylpropionate)amide was used in place 4-(N'-(2-methylphenyl)urea)phenoxyacetyl (methyl methionine-3-amino-3-(3,4-methylenedioxyphenyl)propionate)amide 4-(N'-(2-thienyl)urea)phenoxyacetyl (leucine-3- a) Preparation of 4-(N'-(2-thienyl)urea)phenoxyacetyl (methyl leucine-3-amino-(3,4-methylenedioxy)phenylpropionate)amide Proton-Sponge® (Aldrich) (102 mg) was added to a stirred solution of thiophene-2-carboxylic acid (61 mg) in THF (3 ml) at ambient temperature under argon. After 20 min diphenyl phosphoryl azide (131 mg) were added and the mixture was heated under reflux for 5 hr. The solution was cooled to ambient temperature and a solution of 4-aminophenoxyacetyl (methyl leucine-3-amino-3-(3,4-methylenedioxyphenyl)propionate)amide (243 mg), prepared as in example 30b in THF (5 ml) was added with stirring at ambient temperature and the mixture was refluxed for 12 hr. The cooled mixture was partitioned between ethyl acetate (50 ml) and water (50 ml) and the ethyl acetate phase washed with 1M citric acid, saturated aqueous sodium bicarbonate and brine. Evaporation gave a brown solid which was triturated with ether. The product was isolated by filtration. Yield 43 mg. m/Z (+ve)611.3(M+H) m/Z (–ve) 611.3.

Example 30

Preparation of 4-(N'-phenylurea)-phenoxyacetyl (methyl leucine-3-amino-3-(3,4-methylenedioxyphenyl)propionic acid)amide This was prepared as in Example 1 but using 4-(N'-phenylurea)-phenoxyacetyl(methyl leucine-3-amino-3-(3,4-methylenedioxyphenyl)propionate)amide in place of 4-(N'-(2-methylphenyl)urea)phenoxyacetyl(methyl methionine-3-amino-3-(3,4-methylenedioxy phenyl)propionate)amide.

a) Preparation of 4-nitrophenoxyacetyl (methyl leucine-3-amino-3-(3,4-methylenedioxyphenyl)propionate)amide.

HOBT (1.5 g) was added to a solution of 4-nitrophenoxyacetic acid (1.97 g) in DMF (10 ml), followed by 1-(3-Dimethylaminopropyl)-3-ethylcarbodiimide hydrochloride (2.14 g) and the solution stirred for 15 min. Methyl leucine-3-amino-3-(3,4-methylenedioxyphenyl) propionate (Example 2b) (2.69 g) was dissolved in DMF (10 ml) and the resultant solution added to the solution of the activated ester. The mixture was stirred overnight at ambient temperature. The mixture was added to ethyl acetate(100 ml), washed with water (2 times 10 ml), 5% citric acid (10 ml), water (10 ml), saturated sodium bicarbonate solution (10 ml), water (10 ml), saturated brine (10 ml), dried (MgSO4) and evaporated to give 4-nitrophenoxyacetyl (methyl leucine-3-amino-3-(3,4-methylenedioxyphenyl) propionate)amide 3.02 g.

1H NMR (DMSO-d6, 300 MHz, ppm): 0.9(6H, m), 1.3–1.4(3H,m), 2.7(2H,m), 3.5(3H,s), 4.3–4.4 (1H,s), 4.7 (2H,m), 5.1(1H, m), 5.9(2H,s), 6.7–6.9(3H,m), 7.1(2H,d), 8.2(3H,m), 8.4–8.5(1H,d): m/Z 516 (M+H).

b) Preparation of 4-aminophenoxyacetyl (methyl leucine-3-amino-3-(3,4-methylenedioxyphenyl) propionate)amide At ambient temperature a rapidly stirred solution of 4-nitrophenoxyacetyl (methyl leucine-3-amino-3-(3,4-methylenedioxyphenyl)propionate)amide(3.02 g) in ethyl acetate (60 ml) containing 5% palladium on carbon (0.3 g) was exposed to an atmosphere of hydrogen. When uptake of hydrogen had ceased the solution was filtered and the filter cake washed with ethyl acetate. The combined filtrates were evaporated to dryness to give 2.7 g of 4-aminophenoxyacetyl (methyl leucine-3-amino-3-(3,4-methylenedioxyphenyl)propionate) amide 1H NMR (DMSO-6, 300 MHz, ppm): 0.9(6H, m), 1.3–1.4(3H,m), 2.7(2H,m), 3.5(3H,s), 4.3–4.4 (3H,m),4.7 (2H,m), 5.1(1H, m), 5.9(2H,s), 6.5 (2H,d), 6.7–6.9(5H,m), 7.8(1H,d), 8.4–8.5(1H,d): m/Z 486 (M+H). HPLC Dynamax 60A C18 column; acetonitrile/water/0.1%TFA 20–80% over 20 min Rt 9.7 min used without further purification in the next step.

c) Preparation of 4-(N'-phenylurea)-phenoxyacetyl (methyl leucine-3-amino-3-(3,4-methylenedioxyphenyl)propionate)amide 4-Aminophenoxyacetyl (methyl leucine-3-amino-3-(3,4-methylenedioxyphenyl)propionate) amide (727 mg) and diisopropylethylamine (0.282 ml) were dissolved in dichloromethane (2 ml) and added to a solution of triphosgene (165 mg) in dichloromethane (2 ml) under argon over a period of 30 min. The resultant solution was stirred for 5 min then taken into a syringe and one third of the total volume was added to a solution of aniline (0.042 ml) and diisopropylethylamine (0.093 ml) in dichloromethane (2 ml) under argon. The mixture was stirred overnight at ambient temperature. The mixture was evaporated to dryness then taken up in ethyl acetate(30 ml), washed with water (5 ml), 5% citric acid (5 ml), water (5 ml), saturated sodium bicarbonate solution (5 ml), water (5 ml), saturated brine (5 ml), dried (MgSO4). Evaporation of the solvent and trituration with ether gave 212 mg of 4-(N'-phenylurea)-phenoxyacetyl (methyl leucine-3-amnino-3-(3,4-methylenedioxyphenyl) propionate)amide as a white solid which was hydrolysed without further purification. m/Z 605 (M+H). HPLC Dynamax 60A C18 columnn; acetonitrile/water/0.1%TFA 20–80% over 20 min. Rt 15.8 min. (95% pure).

Example 54

Preparation of 4-(N'-(2-methylphenyl)urea) phenoxyacetyl-(N-(2-methylpropyl) glycine-3-amino-3-(3,4-methylenedioxyphenyl)propionic acid) amide This was prepared as in example 1 but using 4-(N'-(2-methylphenyl)urea)phenoxyacetyl-(methyl N-(2-methylpropyl) glycine-3-amino-3-(3,4-methylenedioxyphenyl)propionate) amide in place of 4-(N'-(2-methylphenyl)urea)phenoxyacetyl (methyl methionine-3-amino-3-(3,4-methylenedioxyphenyl)propionate)amide.

a) Preparation of t-butyl N-(2-methylpropyl) glycine t-Butyl bromoacetate (8.4 ml, 10.1 g) was added under an atmosphere of argon to a solution of isobutylamine (50 ml, 36.8 g) in diethyl ether (100 ml) at −40° C. with stirring over 5 min. The solution was stirred at this temperature for 1 hr and then at ambient temperature for 18 hr. The mixture was filtered and the filtrate distilled at ambient pressure to remove ether and subsequently excess isobutylamine (b.p. 64–66° C.) and then under reduced pressure to give the product Yield 82% b.p. 68° C./3 mm NMR (CDCl$_3$ 300 MHz, ppm) 3.28(2H, s), 2.4(2H, d), 1.72(1H, m), 1.48(9H, s), 0.92(6H,d). m/Z 188.3 (M+H).

b) Preparation of 4-(N'-(2-methylphenyl)urea) phenoxyacetyl-{t-butyl N-(2-methylpropyl) glycine}amide A solution of the 4-(N'-(2-methylphenyl)urea)-phenoxyacetic acid (1.5 g, 5 mmol) in DWF (6 ml) was treated with the t-butyl N-(2-methylpropyl)glycine) (936 mg, 5 mmol), (O-(7-azabenzotriazol-1-yl)-1,1,3,3-tetramethyluronium hexafluorophosphate) (2.28 g, 6 mmol) and diisopropylethylamine (1.9 ml, 11 mmol). The mixture was stirred at room temperature overnight. The mixture was partitioned between EtOAc and water. The EtOAc layer was separated, washed with 1M citric acid, saturated NaHCO$_3$ solution and concentrated in vacuo to a white solid. The solid was purified by chromatography on KP-Sil Ô (Biotage UK Ltd.) with ethyl acetate elution to give the coupled product (1.8 g, 76%) as a white solid.

NMR (100degC., DMSO d6, 300 MHz, ppm) 8.52(1H,s), 7.73(1H,d), 7.66(1H,s), 7.33(2H,d) 7.1(2H,q) 6.92(1H, t) 6.84(2H,d), 4.7(2H, broad s), 4.0(2H, broad s), 3.18(2H, d), 2.24(3H,s), 1.88(1H, m), 1.48(9H,s), 0.85–0.96(6H,s broad). ESPMS (M+NH4) 487.5 c) Preparation of 4-(N'-(2-methylphenyl)urea) phenoxyacetyl-N-(2-methylpropyl) glycine This was prepared according to example 1e using 4-(N'-(2-methylphenyl)urea)phenoxyacetyl-{t-butyl N-(2-methylpropyl)glycine}amide in place of t-butyl 4-(N'-(2-methylphenyl)urea)phenoxyacetate.

4-(N'-(2-methylphenyl)urea)phenoxyacetyl-N-(2-methylpropyl) glycine. m/Z 414.3 (M+H).

d) 4-(N'-(2-methylphenyl)urea)phenoxyacetyl-(methyl N-(2-methylpropyl) glycine-3-amino-3-(3, 4-methylenedioxyphenyl)propionate)amide A solution of the 4-(N'-(2-methylphenyl)urea) phenoxyacetyl-N-(2-methylpropyl) glycine (1.5 g, 3.6 mmol) in a mixture of methylene chloride and DMF 9:1 v/v (70 ml) was treated with methyl 3-amino-3-(3,4-methylenedioxyphenyl)propionate (prepared according to the method described in WO96/22966 (Biogen) at pages 52 to 55 and incorporated herein by reference)(1.6 g, 7.2 mmol), 1-(3-dimethylaminopropyl)-3-ethylcarbodiimide hydrochloride (2.22 g, 7.2 mmol), HOBT (972 mg,7.2 mmol) and diisopropylethylamine (1.3 ml, 7.2 mmol). The mixture was stirred at room temperature overnight. The mixture was partitioned between EtOAc and water. The EtOAc layer was separated, washed with 1M citric acid, saturated NaHCO$_3$ solution and concentrated in vacuo to a translucent gum. The gum was purified by chromatography on KP-Sil Ô (Biotage UK Ltd.) with toluene/ethyl acetate elution to give the coupled product (1.3 g, 58%) as a white solid.

4-(N'-(2-methylphenyl)urea)phenoxyacetyl-(methyl N-(2-methylpropyl) glycine-3-amino-3-(3,4-methylenedioxyphenyl)propionate)amide.

NMR (DMSO d6, 300 MHz, ppm) 0.73–0.93(6H,m), 1.75–1.83(1H,m), 2.21(3H,s), 2.75(2H,t), 3.0–3.2 (2H,m), 3.52(3H,s), 3.82(2H,d), 4.70(2H,d), 5.18(1H, m), 5.95(2H, s), 6.7–6.9(6H,m), 7.0–7.1(2H,q), 7.3 (2H,d), 7.8(2H,d), 8.24–8.67(1h,dd), 8.79(1H,d). m/Z 619.4 (M+H).

Example 66

Preparation of 4-(N'-(2-methylphenyl)urea) phenoxyacetyl-(2-(2-methoxyethyl) glycine-3-amino-3-(3,4-methylenedioxyphenyl)propionic acid) amide This was prepared according to example 54 except that in 54b methyl 2-(2-methoxyethyl)glycine was used in place of t-butyl N-(2-methylpropyl) glycine. Methyl 2-(2-methoxyethyl)glycine was prepared by the method described in European Patent Application No. 618 221. Hydrolysis of the substituted glycine ester in example 54c was achieved using LiOH as described in example 1.

Example 67

4-(N'-(2-methylphenyl)urea)-3-methoxy phenoxyacetyl (leucine-3-amino-(3,4-methylenedioxy)phenylpropionic acid)amide This was prepared according to example 1 except that 4-(N'-(2-methylphenyl)urea)-3-methoxyphenoxyacetyl (methyl leucine-3-amino-3-(3,4-methylenedioxyphenyl) propionate)amide was used in place of 4-(N'-(2-methylphenyl)urea)-phenoxyacetyl (methyl methionine-3-amino-3-(3,4-(methylenedioxy)phenylpropionate)amide and in 1c 4-nitro-3-methoxyphenol was used in place of 4-nitrophenol.

a) 4-Nitro-3-methoxyphenol

A solution of sodium hydroxide was added to a stirred solution of 4-fluoro-2-methoxynitrobenzene (11.1 g.) in DMSO (60 ml.) at ambient temperature and the mixture was heated at 85 degC. for 2.5 hr. The cooled solution was diluted with water (100 ml.) and extracted with ether (3×100 ml.) The combined ethereal solution was extracted with 2n NaOH (3×75 ml.) and the combined aqueous phase brought to pH 2 by the addition of 2N HCl. The precipitated product was collected and washed with water. The product was dried over phosphorous pentoxide. Yield 7.4 g. m/Z 170.1(M+H). It was used without further purification in the next step (cf Example 1c).

Example 69

Preparation of 4-(N'-(pyrid-3-yl)urea)-phenoxyacetyl (methyl leucine-3-amino-3-(3,4-methylenedioxyphenyl)propionic acid)amide This was prepared as in Example 1 but using 4-(N'-(pyrid-3-yl) urea)-phenoxyacetyl (methyl leucine-3-amino-3-(3,4-methylenedioxyphenyl)propionate)amide in place of 4-(N'-(2-methylphenyl)urea)phenoxyacetyl (methyl methionine-3-amino-3-(3,4-methylenedioxy phenyl)propionate)amide.

a) Preparation of 4-(N'-(pyrid-3-yl)urea)-phenoxyacetyl (methyl leucine-3-amino-3-(3,4-methylenedioxyphenyl)propionate)amide 3-Pyridyl isocyanate (75 mg. 0.62 mmol) was added to a stirred solution of 4-aminophenoxyacetyl (methyl leucine-3-amino-3-(3,4-methylenedioxyphenyl)propionate) amide (see Example 30b) (280 mg. 0.58 mmol.) in dry ethyl acetate at ambient temperature. The mixture was heated to reflux for 2 hours, and the product collected by filtration. Yield 200 mg. (56%).

$^1$HNMR (DMSOd6, 300 MHz, ppm): 0.78 (6H, t); 1.39 (3H, m); 2.73 (2H, q); 3.52(3H, s); 4.37 (1H, m); 4.47 (2H, s) 5.11 (1H,q); 5.96 (2H, s); 6.72(1H, d); 6.81 (1H, d); 6.87(3H,d); 7.26–7.38 (3H,m); 7.92 (2H,m); 8.15 (1H,d); 8.45 (1H,d); 8.60 (2H, d); 8.76 (1H, s); ESPMS 606.4 (M+H)$^+$ Example 71

Preparation of 7-(N'-(2-methylphenyl)urea)-2,3-dihydrobenzofuranyl-4-oxyacetyl(leucine-3-amino-(3,4-methylenedioxy)phenylpropionic acid)amide This was prepared as in example 1 but, in 1e, using t-butyl 7-(N'-(2-methylphenyl)urea)-2,3-dihydrobenzofuranyl-4-oxyacetate in place of t-butyl 4-(N'-(2-methylphenyl)urea) phenoxyacetate and in 1f using methyl leucine-3-amino-3-(3,4-methylenedioxy phenyl)propionate in place of methyl methionine-3-amino-3-(3,4-methylenedioxy phenyl) propionate.

a) Preparation of 4-hydroxy-dihyrobenzofuran

At ambient temperature a rapidly stirred solution of 4-hydroxybenzofuran (2.0 g) (prepared by the method of G. Keen & P. Maddocks Syn. Comm., 16(13), 1635–1640 (1986)) in glacial acetic acid (30 ml) containing 30% palladium on carbon (0.2 g) was exposed to an atmosphere of hydrogen. When uptake of hydrogen had ceased the solution was filtered and the filter cake washed with glacial acetic acid. The combined filtrates were evaporated to dryness to give of 4-hydroxy-dihydrobenzofuran (2.05 g) 1H NMR (DMSO-d6, 300 MHz, ppm): 3.0(2H,t), 4.5(2H,t), 6.2(1H.d), 6.3(1H,d), 6.8(1H,t), 9.5(1H,b) m/Z 135 (M−H).

b) Preparation of 4-hydroxy,7-(hydrazine1,2-dicarboxylic acid bis(2,2,2-trichloroethyl ester)-2,3-dihydrobenzofuran Trifluorosulphonic acid(0.114 ml) was added to a solution of 4-hydroxy-dihydrobenzofuran(1.77 g) in dichloromethane (80 ml) at −70° C. under an atmosphere of argon, followed by bis(2,2,2-trichloroethyl) azodicarboxylate (BTEAD) (6 g). The mixture was stirred at −60° C. for 30 min. then quenched with 25% ammonium acetate solution (30 ml), allowed to warm to ambient temperature and extracted with ethyl acetate(2 times 100 ml), the combined organic extracts were washed with saturated brine(20 ml), dried (MgSO$_4$), evaporated and purified using the Biotage 40M system, eluting with 5% ethyl acetate/toluene to give 4-hydroxy,7-(hydrazine1,2-dicarboxylic acid bis(2,2,2-trichloroethyl ester)-2,3-dihydrobenzofuran (4.73 g) 1H NMR (DMSO-d6, 300 MHz, ppm): 3.0(2H,t), 4.5(2H,t), 4.8(4H,s), 6.2(1H.d), 7.0(1H,d), 9.6(1H,s), 10.75(1H,s) m/Z 515 (M−H).

c) Preparation of t-butyl-7-(hydrazine1,2-dicarboxylic acid bis(2,2,2-trichloroethyl ester)-2,3-dihydrobenzofuranyl-4-oxyacetate t-Butyl bromoacetate(1.62 ml) was added to a solution of 4-hydroxy,7hydrazine1,2-dicarboxylic acid bis(2,2,2-trichloroethyl ester)-2,3-dihydrobenzofuran in butan-2-one (50 ml) containing powdered potassium carbonate(1.63 g) and the mixture was stirred overnight at 80° C. The mixture was evaporated to dryness then taken up in ethyl acetate(50 ml), washed with water (20 ml), the aqueous phase was extracted again with ethyl acetate (20 ml), the combined organic extracts were washed with saturated sodium bicarbonate solution(20 ml) and saturated brine(20 ml), dried (MgSO$_4$). Evaporation gave t-butyl-7-(hydrazine1,2-dicarboxylic acid bis(2,2,2-trichloroethyl ester)-2,3-dihydrobenzofiiranyl-4-oxyacetate(5.4 g) m/Z 266 (M+H) used without ftirther purification in the next step.

d) Preparation of t-butyl-7-amino-2,3-dihydrobenzofuranyl-4-oxyacetate

Zinc dust (2 g) was added to a stirred solution of t-butyl-7-(hydrazine1,2-dicarboxylic acid bis(2,2,2-trichloroethyl ester)-2,3-dihydrobenzofuranyl-4-oxyacetate (2 g) in glacial acetic acid (20 ml) under argon. After for 1 hr 5N sodium hydroxide solution (70 ml) was added and the mixture was extracted with ethyl acetate (3 times 100 ml), dried (Na$_2$SO$_4$). Evaporation and purification by chromatography on a 40S Biotage system eluting with 10% ethyl acetate/toluene gave t-butyl-7-amino-2,3-dihydrobenzofuranyl-4-oxyacetate as a pale yellow solid (341 mg).

1H NMR (CDCl$_3$, 300 MHz, ppm):1.5(9H,s), 3.2(2H,t), 4.4(2H,s), 4.6(2H,t), 6.1(1H,d), 6.5(1H,d),: m/Z 266 (M+H).

e) Preparation of t-butyl 7-(N'-(2-methylphenyl)urea)-2,3-dihydrobenzofuranyl-4-oxyacetate Undiluted 2-methylphenylisocyanate(171 mg. 160 µl) was added to a stirred solution of t-butyl-7-amino-2,3-dihydrobenzofuranyl-4-oxyacetate (341 mg) in methylene chloride (5 ml) under argon at ambient temperature over 2 min. The mixture was stirred for 18 hr and then evaporated. The residue was triturated with ether and the solid filtered. This product was used with out further purification. Yield 74%. 1H NMR (DMSO-d6, 300 MHz, ppm) 1.4(9H,s), 2.2(3H,s), 3.2(2H,t), 4.6(2H,s), 4.7(2H,t), 6.3(1H,d), 6.9 (1H,t) 7.1(1H,t) 7.7(1H,d) 7.8(1H,d) 8.2(1H,s) 8.4(1H,s).

Example 77

Pharmaceutical compositions.

The compounds of the invention may be formulated into tablets together with, for example, lactose Ph.Eur, Croscarmellose sodium, maize starch paste (5% w/v paste) and magnesium stearate for therapeutic or prophylactic use in humans.

In vitro and in vivo Assays

The following abbreviations are used. Suitable sources of materials are listed below. MOLT-4 cells—human T-lymphoblastic leukaemia cells (European Collection of Animal Cell Cultures, Porton Down)

Fibronectin—purified from human plasma by gelatin-sepharose affinity chromatography according to the methods described in E. Nengvall, E. Ruoslahti, Int. J. Cancer, 1977, 20, pages 1–5 and J. Forsyth et al, Methods in Enzymology, 1992, 215, pages 311–316).

RPMI 1640—cell culture medium. (Life technologies, Paisley UK).

PBS—Dulbecco's phosphate buffered saline (Life Technologies).

BSA—Bovine serum albumin, fraction V (ICN, Thame, UK).

CFA—Complete Freund's Adjuvant (Life Technologies).

In the following assays and models references to compound (s) refers to the compounds of formulae (II), (III) and (IV) according to the present invention.

1.1 In vitro Assay 1.1.1 MOLT-4 cell/Fibronectin adhesion assay.

The MOLT-4 cell/fibronectin adhesion assay was used to investigate the interaction of the integrin $\alpha_4$-$\beta_1$ expressed on the MOLT-4 cell membrane with fibronectin. Polystyrene 96 well plates were coated overnight at 4° C. with fibronectin, 100 µl of 10 µg/ml in PBS. Non-specific adhesion sites were blocked by adding 100 µl BSA, 20 mg/ml. After incubating for 1 h at room temperature, the solutions were aspirated. MOLT-4 cells suspended in serum-free RPMI-1640 medium 2E6 cells/ml (50 µl) and solutions of compound diluted in the same medium (50 µl) were added to each well. After incubation for 2 h at 37° C. in a humidified atmosphere of 5% (v/v) CO$_2$, non-adherent cells were removed by gentle shaking followed by vacuum aspiration. Adherent cells were quantified by a colorimetric acid phosphatase assay. To each well was added 100 µl p-nitrophenyl phosphate (6 mg/ml) in 50 mM sodium acetate buffer, pH 5.0, containing 1% Triton X-100. After incubation for 1 h at 37° C., 50 µl sodium hydroxide (1M) was added to each well and the absorbance 405 nm was measured on a microplate spectrophotometer. Compounds which inhibited adhesion gave a lower absorbance reading. Standard, control and test conditions were assayed in triplicate. Percentage inhibition was calculated with respect to total (no inhibitor) and non-specific (no fibronectin) standards on each plate.

1.2 In-vivo Inflammation Models

Activity of a compound can be tested in the following models.

1.2.1 Ovalbumin Delayed Type Hypersensitivity in Mice

Balb/c female mice (20–25 g) are immunised on the flank with an 1:1 (v/v) emulsion of ovalbumin (2 mg/ml) with CFA. Seven days later the mice are challenged by subplantar injection of 1% heat aggregated ovalbumin in saline (30 µl) into the right hind foot pad. Swelling of the foot develops over a 24 hour period following which foot pad thickness is measured and compared with the thickness of the contralateral uninjected foot. The percentage increase in foot pad thickness is calculated. Compounds are dosed orally by gavage to groups of 5 mice at doses ranging from 0.001 mg/kg to 100 mg/kg. Inhibition of the inflammatory response is calculated comparing vehicle treated animals and compound treated groups.

1.2.2. Collagen-induced Arthritis in Mice

DBA/1 male mice are immunised with 0.1 ml of an emulsion prepared from equal volumes of bovine collagen type II in 0.05M acetic acid (2 mg/ml) and CFA. This mixture is injected at the base of the tail. Twenty days later compounds are dosed orally by gavage at doses ranging from 0.001 mg/kg/day to 100 mg/kg/day. On the day following the first dose, each animal receives an intraperitoneal booster injection of 0.1 ml of collagen type II in acetic acid. The mice are assessed for the incidence and severity of arthritis in all four limbs for up to 28 days. Inhibition of arthritis is calculated by comparing vehicle treated and compound treated mice.

TABLE 1
| Ex. No | Structure | Synthetic Method Code — Urea Formation | Synthetic Method Code — Final ester Hydrolysis | Methods for Intermediates | ESPMS M−H | ESPMS M+H | NMR 1H, ppm. d6-DMSO | Reverse Phase HPLC (Run Time = 20 min.) Column Type | Solvent + 0.1% TFA | Rt. min. |
|---|---|---|---|---|---|---|---|---|---|---|
| 13 | 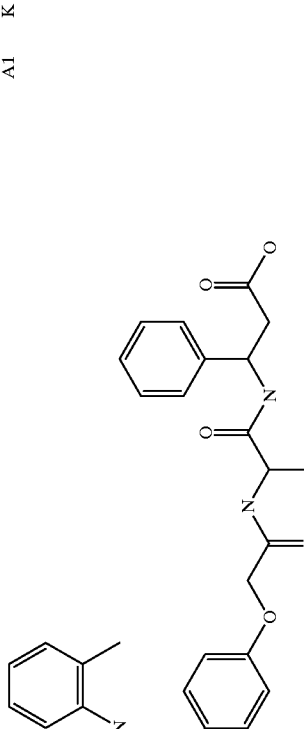 | A1 | | K | 559 | | 0.7–0.9(m, 6H); 1.3–1.6(m, 3H); 2.2(s, 3H); 2.65(m, 2H); 4.3–4.5(m, 3H); 5.15(m, 1H); 6.8–6.95(m, 3H); 7.1(m, 2H); 7.2–7.4(m, 7H); 7.8(m, 2H); 7.9(m, 1H); 8.45–8.55(m, 1H); 8.8(m, 1H). | | | |
| 14 | 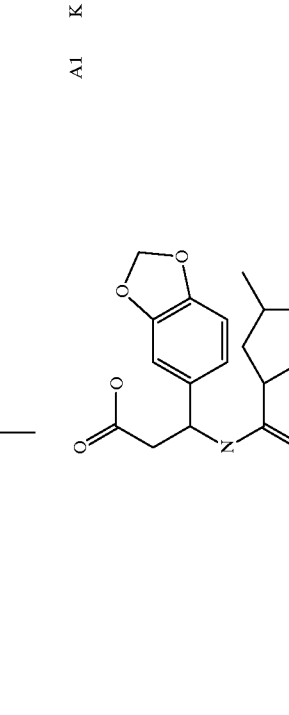 | A1 | | K | 651 | | 0.75(M,6H)1.25(M.3H)2.25(S.3H):2.6 (T.3H):4.1–4.3(M.3H):5.05(Q.1H):5.95 (S.2H):6.7–6.9(M.3H):6.95.(T.1H):7.1–7.2(M.2H):7.6–7.8(M.5H):8.25(D.1H): 8.4(S.1H).9.8(S.1H) | | | |

TABLE 1-continued

| Ex. No | Structure | Synthetic Method Code Urea Formation | Final ester Hydrolysis | Methods for Intermediates | ESPMS M−H | M+H | NMR 1H, ppm. d6-DMSO | Reverse Phase HPLC (Run Time = 20 min.) Column Type | Solvent + 0.1% TFA | Rt. min. |
|---|---|---|---|---|---|---|---|---|---|---|
| 15 | 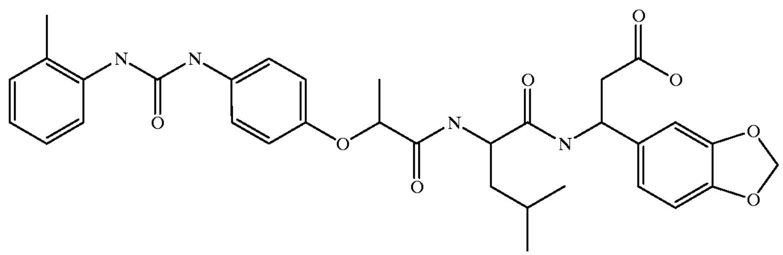 | A1 | K | | | 617 | 0.8(m), 6H; 1.4(m), 6H; 2.2(s), 3H; 2.6(m), 2H; 4.3, (m), 1H; 4.7(m), 1H; 5.05(m), 1H; 5.95(s), 2H; 6.7(m), 1H; 6.8(m), 3H; 6.9(m), 1H; 7.1(m), 2H; 7.3(m), 2H; 7.8(m), 2H; 7.88(d) & 8.1(d), 1H 8.4(m), 1H; 8.9(s), 1H | | | |
| 16 | 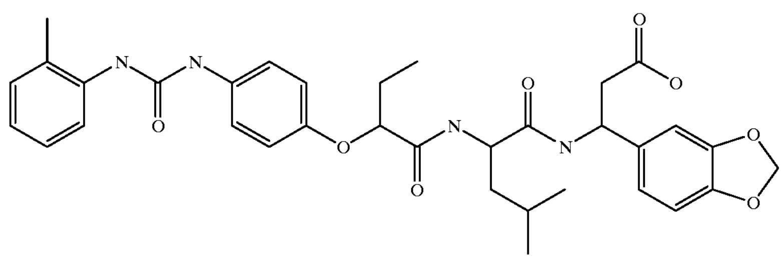 | A1 | K | | | 631 | DMSO: 0.8(m), 6H; 0.95(t), 3H; 1.4(m), 3H; 1.8(m), 2H; 2.2(s), 3H; 2.6(m), 2H; 4.3(m), 1H; 4.5(m), 1H; 5.0(m), 1H; 5.95(s), 2H; 6.8(m), 6H; 7.1(m), 2H; 7.3(m), 2H; 7.8(m), 2H, 7.85(d) & 8.05(d), 1H; 8.3(d) & 8.4(d), 1H, 8.8(s), 1H | | | |

TABLE 1-continued

| Ex. No | Structure | Synthetic Method Code - Urea Formation | Synthetic Method Code - Final ester Hydrolysis | Methods for Intermediates | ESPMS M+H | ESPMS M−H | NMR 1H, ppm. d6-DMSO | Reverse Phase HPLC Column Type | Reverse Phase HPLC Solvent + 0.1% TFA | Reverse Phase HPLC Rt. min |
|---|---|---|---|---|---|---|---|---|---|---|
| 17 | 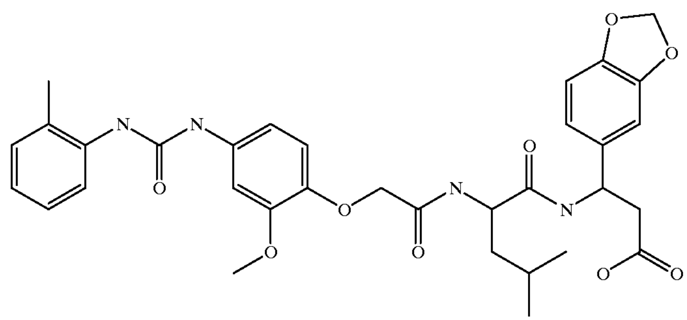 | A1 | K | | 635.5 | | 0.7–0.9(6H, m), 1.3–1.5(3H, m), 2.2(3H, s), 2.5–2.7(2H, m), 3.75(3H, s), 4.2–4.4(1H, m), 4.55(2H, s), 5.0–5.1(1H, m), 5.95(2H, s), 6.7–6.95(6H, m), 7.05–7.15(2H, m), 7.25(1H, s), 7.75–7.85(2H, m), 7.95(1H, s), 8.50–8.60(1H, d), 9.05(1H, s) | Dynamax 60A C18 | MeCN/ H2O 20-80 | 14.4 |
| 18 | 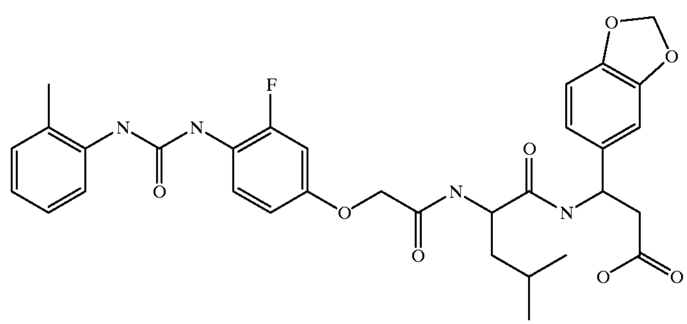 | A1 | K | | 623.4 | | 0.7–0.9(6H, m), 1.3–1.5(3H, m), 2.2(3H, s), 2.5–2.7(2H, m), 4.2–4.4(1H, m), 4.55(2H, s), 5.0–5.1(1H, m), 5.95(2H, s), 6.7–7.95(6H, m), 7.05–7.3(2H, m), 7.75–7.85(1H, d), 7.9–7.95(1H, t), 7.95–8.05(1H, d), 8.2(1H, s), 8.4–8.5(1H, d), 8.75(1H, s) | Dynamax 60A C18 | MeCN/ H2O 20-80 | 14.8 |

TABLE 1-continued
| Ex. No | Structure | Synthetic Method Code Urea Formation | Final ester Hydrolysis | Methods for Intermediates | ESPMS M−H | M+H | NMR 1H, ppm. d6-DMSO | Reverse Phase HPLC (Run Time = 20 min.) Column Type | Solvent + 0.1% TFA | Rt. min. |
|---|---|---|---|---|---|---|---|---|---|---|
| 19 | 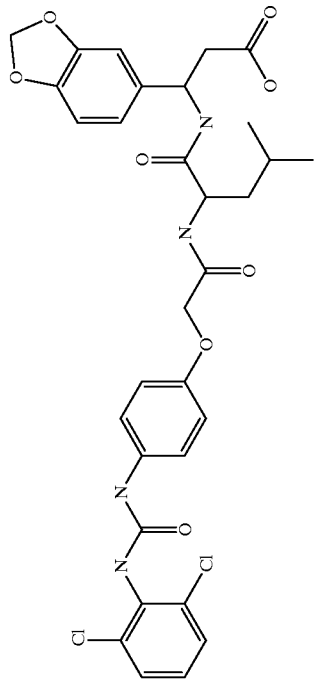 | A1 | K | | | 659.3 | 0.7–0.9(6H, m), 1.3–1.5(3H, m), 2.5–2.7 (2H, m), 4.2–4.4(1H, m), 4.55(2H, s), 5.0–5.1(1H, m), 5.95(2H, s), 6.7–6.95(5H, m), 7.2–7.3(1H, t), 7.3 7.5(4H, m), 7.95–8.05 (1H, d), 8.9–9.0(1H, d), 9.4(1H, s), 9.9 (1H, s) | Dynamax 60A C18 | MeCN/ H2O 20-80 | 13.5 |
| 20 | 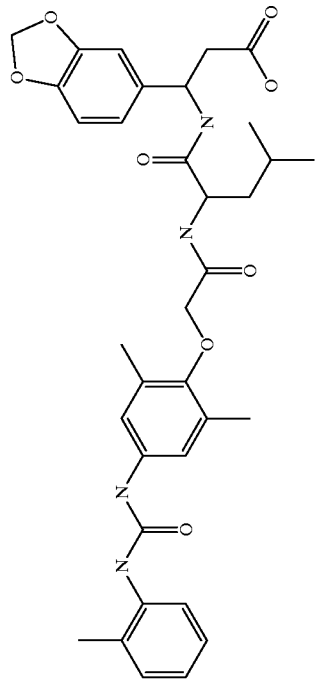 | A1 | K | | | 633.4 | 0.7–0.9(6H, m), 1.3–1.5(3H, m), 2.15(6H, s), 2.25(3H, s), 2.5–2.7(2H, m), 4.15(2H, s), 4.4–4.5(1H, m), 5.0–5.1(1H, m), 5.95(2H, s), 6.7–6.9(4H, m), 7.05–7.15(4H, m), 7.75–7.85(1H, d), 7.9(1H, s), 7.95(1H, s), 8.45–8.5(1H, d), 8.9(1H, s) | Dynamax 60A C18 | MeCN/ H2O 20-80 | 15.3 |

TABLE 1-continued
| Ex. No | Structure | Synthetic Method Code Urea Formation | Final ester Hydrolysis | Methods for Intermediates | ESPMS M−H | M+H | NMR 1H, ppm, d6-DMSO | Reverse Phase HPLC (Run Time = 20 min.) Column Type | Solvent + 0.1% TFA | Rt. min |
|---|---|---|---|---|---|---|---|---|---|---|
| 21 | 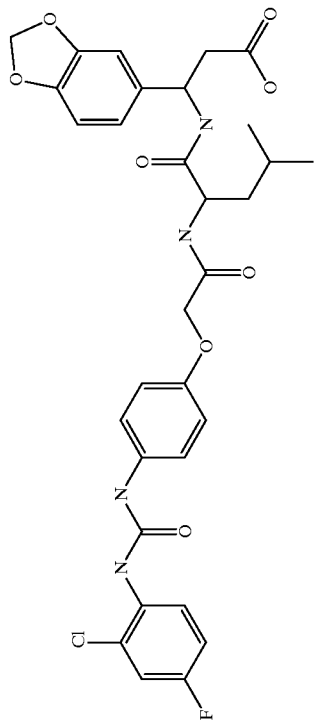 | A2 | | K | | 643.2 | 0.7–0.9(6H, m), 1.3–1.5(3H, m), 2.5–2.7 (2H, m), 4.2–4.4(1H, m), 4.55(2H, s), 5.0–5.1(1H, m), 5.95(2H, s), 6.7–6.9(5H, m), 7.1–7.2(1H, m), 7.3–7.4(3H, m), 7.9–8.1 (2H, m), 8.6(1H, s), 8.9–9.0(1H, d), 9.6–9.7(1H, s) | Dynamax 60A C18 | MeCN/ H2O 20-80 | 15.9 |
| 22 | 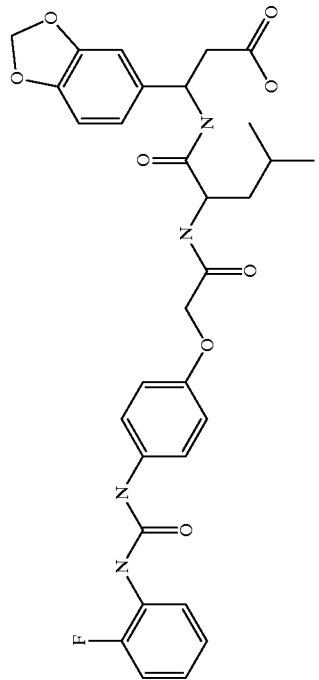 | A1 | | K | | 609.3 | 0.7–0.9(6H, m), 1.3–1.5(3H, m), 2.5–2.7 (2H, m), 4.2–4.4(1H, m), 4.55(2H, s), 5.0–5.1(1H, m), 5.95(2H, s), 6.65–6.95(6H, m), 7.05–7.1(1H, t), 7.1–7.2(1H, m), 7.35–7.3 (2H, m), 7.8–7.9(1H, d), 8.0–8.1(1H, t), 8.35–8.45(2H, m), 8.85(1H, s) | Dynamax 60A C18 | MeCN/ H2O 20-80 | 14.8 |

TABLE 1-continued

| Ex. No | Structure | Synthetic Method Code Urea Formation | Synthetic Method Code Final ester Hydrolysis | Methods for Intermediates | ESPMS M−H | ESPMS M+H | NMR 1H, ppm. d6-DMSO | Reverse Phase HPLC (Run Time = 20 min.) Column Type | Solvent + 0.1% TFA | Rt. min |
|---|---|---|---|---|---|---|---|---|---|---|
| 23 | 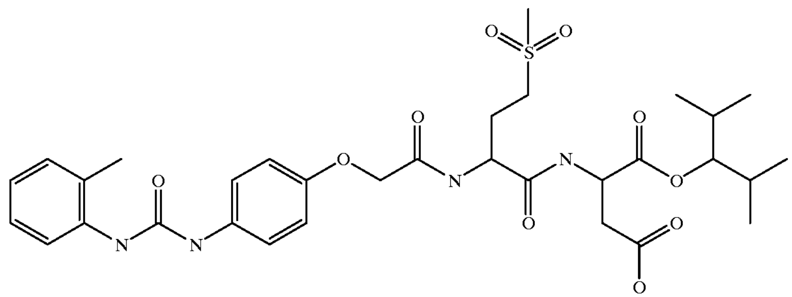 | A1 | | L | 675 | | 0.75(m, 12H); 1.8(m, 2H); 2.0(m, 1H); 2.1 (m, 1H); 2.2(s, 3H); 2.7(m, 2H); 2.95(s, 3H); 3.05(m, 2H); 4.4–4.6(m, 4H); 4.7(q, 1H); 6.8–6.9(m, 3H); 7.0–7.2(m, 2H); 7.35(d, 2H); 7.8(d, 1H); 7.85(s, 1H); 8.2(d, 1H); 8.6 (d, 1H); 8.9(s, 1H). | | | |
| 24 | 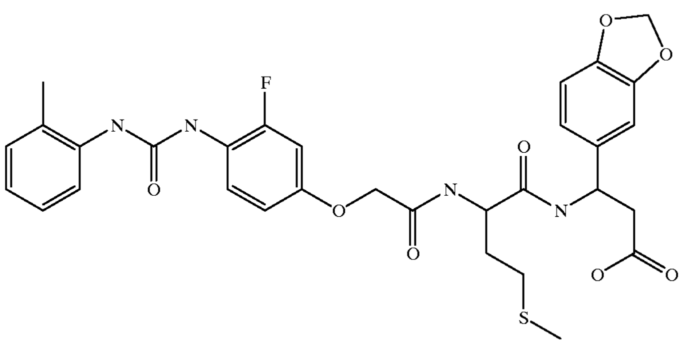 | A1 | | K | | 641.3 | 1.7–1.9(2H, m), 1.95(3H, s), 2.1–2.2(5H, m), 2.6–2.7(2H, m), 4.3–4.4(1H, m), 4.55 (2H, s), 5.0–5.15(1H, m), 5.9(2H, s), 6.7–7.0(6H, m), 7.1–7.2(2H, m), 7.8(1H, d), 7.9–8.0(1H, t), 8.05–8.1(1H, d), 8.2(1H, s), 8.5(1H, d), 8.7(1H, s) | Dynamax 60A C18 | MeCN/ H2O 20-80 | 14.3 |

TABLE 1-continued

| Ex. No | Structure | Synthetic Method Code — Urea Formation | Synthetic Method Code — Final ester Hydrolysis | Methods for Intermediates | ESPMS M−H | ESPMS M+H | NMR 1H, ppm. d6-DMSO | Reverse Phase HPLC (Run Time = 20 min.) Column Type | Solvent + 0.1% TFA | Rt. min. |
|---|---|---|---|---|---|---|---|---|---|---|
| 25 | 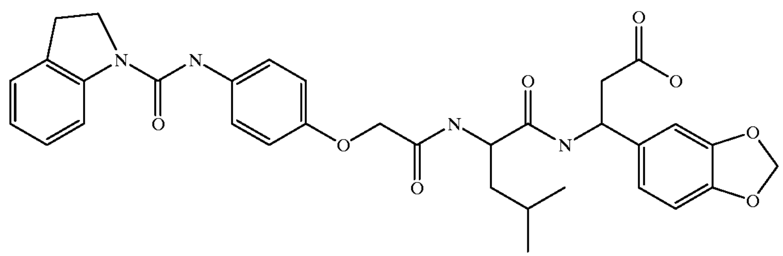 | B |  | K | 616 |  | 0.8–1.0(6H, m), 1.5–1.7(3H, m), 2.6–2.8 (2H, m), 3.2–3.3(2H, t), 4.1–4.2(2H, t), 4.4–4.5(1H, m), 4.6(2H, s), 5.1–5.2(1H, m), 6.1 (2H, s), 6.8–7.0(6H, m), 7.1–7.2(1H, t), 7.2–7.3(1H, d), 7.5–7.6(2H, d), 7.9(2H, d), 8.4 (1H, d), 8.5(1H, d) | Dynamax 60A C18 | MeCN/ H2O 20-80 | 15.4 |
| 26 | 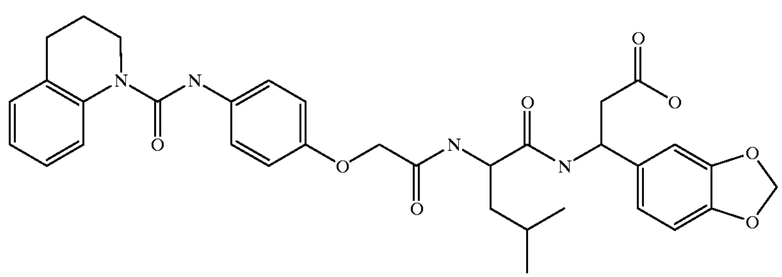 | B |  | K | 629 |  | 0.8–1.0(6H, m), 1.5–1.7(3H, m), 2.0–2.1 (2H, m), 2.6–2.8(2H, m), 3.5–3.6(2H, m), 3.8–3.9(2H, m), 4.4–4.5(1H, m), 4.6(2H, s), 5.1–5.2(1H, m), 6.1(2H, s), 6.8–7.4(9H, m), 7.5–7.6(2H, d), 8.0–8.1(1H, d), 8.7(1H, d), 9.1–9.2(1H, d) | Dynamax 60A C18 | MeCN/ H2O 20-80 | 15.6 |
| 27 | 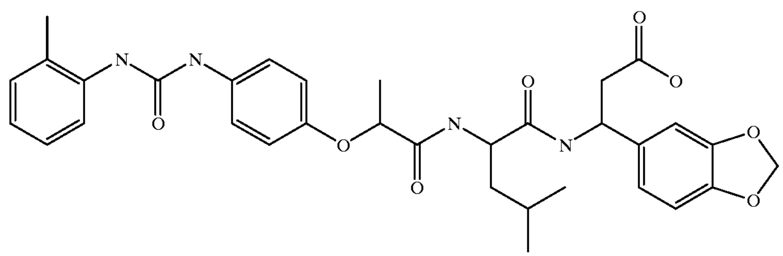 | A1 |  | K | 617 |  | 0.7(m), 6H; 1.4(m), 6H; 2.2(s), 3H; 2.6(m), 2H; 4.3, (m), 1H; 4.7(m), 1H; 5.05(m), 1H; 5.95(s), 2H; 6.8(m), 6H; 7.1(m), 2H, 7.3(m), 2H; 7.8(m), 3H; 8.4(s), 1H; 8.8(s), 1H |  |  |  |

TABLE 1-continued

| Ex. No | Structure | Synthetic Method Code Urea For-ma-tion | Final ester Hy-drol-ysis | Meth-ods for Inter-medi-ates | ESPMS M−H | M+H | NMR 1H, ppm. d6-DMSO | Reverse Phase HPLC (Run Time = 20 min.) Column Type | Sol-vent + 0.1% TFA | Rt. min. |
|---|---|---|---|---|---|---|---|---|---|---|
| 28 | 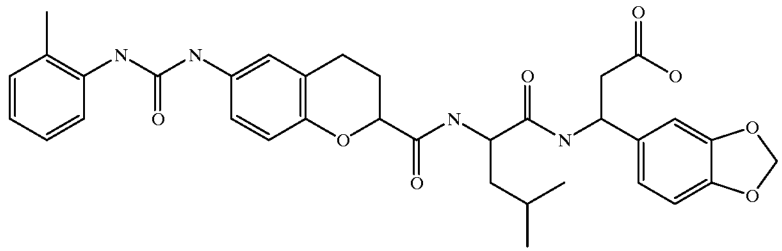 | A1 | K | | 629 | | 0.8(m), 6H; 1.4(m), 3H; 1.9(m); 1H, 2.1 (m), 2H; 2.2 (s), 3H; 2.6(m), 2H; 2.8(m), 1H; 4.4(m), 1H; 4.5(m), 1H; 5.05(m), 1H; 5.95(s), 2H; 6.8 (m), 5H; 7.1(m), 4H; 7.6 (d) & 7.8(d), 1H; 7.75(m), 2H; 8.4(d) & 8.5 (d), 1H; 8.8(s), 1H | | | |
| 29 | 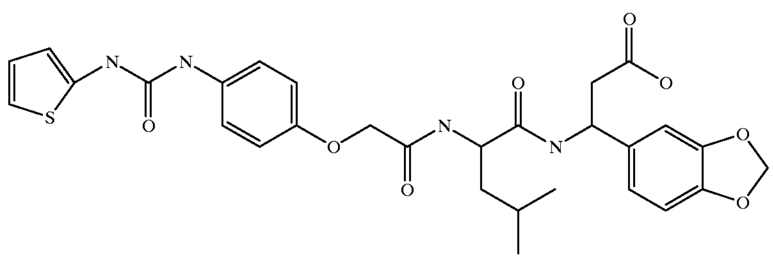 | A2 | K | | | 597.2 | 0.7–0.9(6H, m), 1.3–1.5(3H, m), 2.5–2.7 (2H, m), 4.3–4.5(3H, m), 5.0–5.1(1H, m), 5.95(2H, s), 6.5(1H, s), 6.65–6.9(6H, m), 7.2(1H, m), 7.3–7.35(2H, d), 7.9–7.95(1H, d), 8.4–8.45(1H, d), 8.5(1H, s), 9.5(1H, s) | Dynamax 60A C18 | MeCN/ H2O 20-80 | 13.8 |
| 30 | 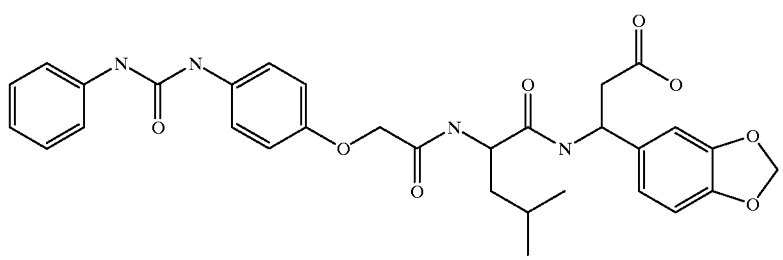 | C1 | K | | 589 | | 0.7–0.9(6H, m), 1.3–1.5(3H, m), 2.5–2.7 (2H, m), 4.2–4.4(1H, m), 4.5(2H, s), 4.9–5.1(1H, m), 5.9(2H, s), 6.6–6.9(6H, m), 7.2 (2H, t), 7.3–7.4(2H, d), 7.5(2H, d), 8.0(1H, d), 8.8(1H, d), 9.3–9.6(2H, d) | Dynamax 60A C18 | MeCN/ H2O 20-80 | 14.2 |

TABLE 1-continued

| Ex. No | Structure | Synthetic Method Code Urea For- mation | Final ester Hy- drol- ysis | Meth- ods for Inter- medi- ates | ESPMS M−H | M+H | NMR 1H, ppm. d6-DMSO | Reverse Phase HPLC (Run Time = 20 min.) Column Type | Sol- vent + 0.1% TFA | Rt. min. |
|---|---|---|---|---|---|---|---|---|---|---|
| 31 | 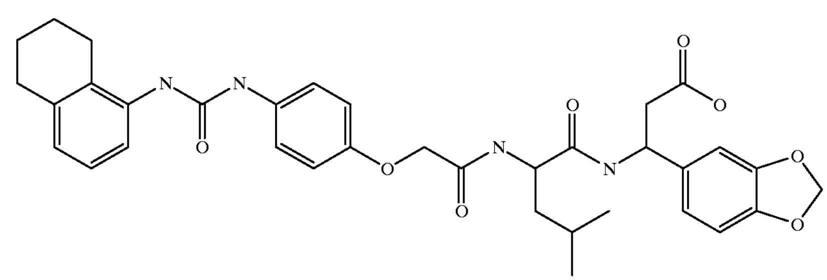 | C1 | | K | 643 | | 0.7–0.9(6H, m), 1.3–1.5(3H, m), 1.7(4H, m), 2.4(2H, m), 2.5–2.6(2H, m), 2.7(2H, m), 4.2–4.4(1H, m), 4.5(2H, s), 4.9–5.1(1H, m), 5.9(2H, s), 6.6–6.9(6H, m), 7.0(1H, t), 7.3–7.4(2H, d), 7.5(1H, d), 8.0(1H, d), 8.3(1H, s), 9.1(1H, m), 9.5(1H, s) | Dynamax 60A C18 | MeCN/ H2O 20-80 | 16.8 |
| 32 | 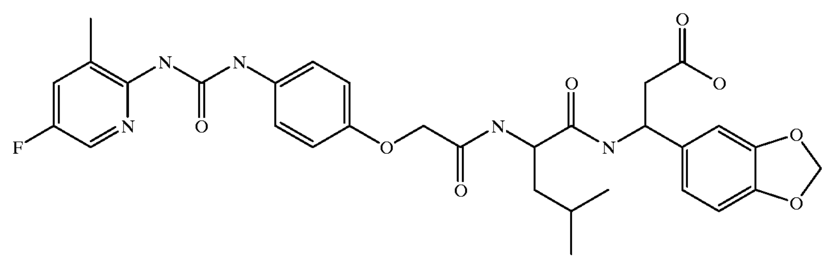 | C1 | | K | 621 | | 0.7–0.9(6H, m), 1.3–1.5(3H, m), 2.2(3H, s), 2.5–2.6(2H, m), 4.2–4.4(1H, m), 4.5(2H, s), 4.9–5.1(1H, m), 5.9(2H, s), 6.6–7.0(7H, m), 7.3–7.4(2H, d), 7.6(1H, m), 8.0(1H, d), 8.6(1H, s), 8.9(1H, d), 9.5(1H, s) | Dynamax 60A C18 | MeCN/ H2O 20-80 | 14.8 |
| 33 | 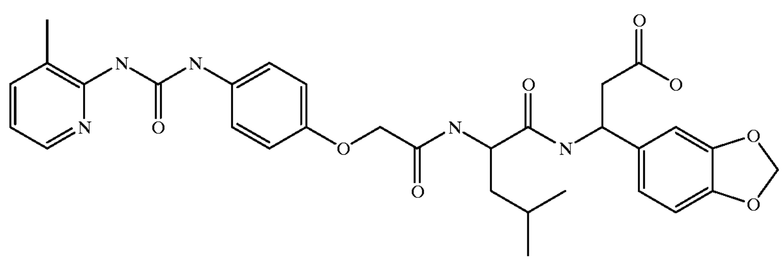 | C1 | | K | 604 | | 0.7–0.9(6H, m), 1.3–1.5(3H, m), 2.2(3H, s), 2.5 2.6(2H, m), 4.2–4.4(1H, m), 4.5(2H, s), 4.9–5.1(1H, m), 5.9(2H, s), 6.6–7.0(6H, m), 7.3–7.4(2H, d), 7.6(1H, d), 8.0(1H, d), 8.2 (1H, d), 8.4(2H, m) | Dynamax 60A C18 | MeCN/ H2O 20-80 | 11.3 |

TABLE 1-continued

| Ex. No | Structure | Synthetic Method Code - Urea Formation | Synthetic Method Code - Final ester Hydrolysis | Methods for Intermediates | ESPMS M−H | ESPMS M+H | M+ NMR 1H, ppm. d6-DMSO | Reverse Phase HPLC (Run Time = 20 min.) Column Type | Solvent + 0.1% TFA | Rt. min |
|---|---|---|---|---|---|---|---|---|---|---|
| 34 | 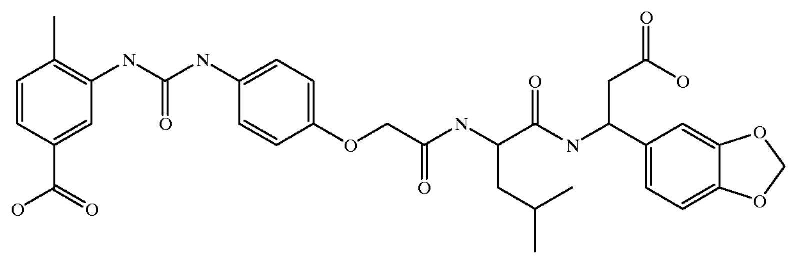 | C1 | | K | 647 | | 0.7–0.9(6H, m), 1.3–1.5(3H, m), 2.3(3H, s), 2.5 2.6(2H, m), 4.2–4.4(1H, m), 4.5(2H, s), 4.9–5.1(1H, m), 5.9(2H, s), 6.6–6.9(5H, m), 7.3–7.4(3H, m), 7.5(1H, d), 7.9(1H, d), 8.0 (1H, s), 8.4(2H, m), 8.9(1H, s) | Dynamax 60A C18 | MeCN/ H2O 20-80 | 12.6 |
| 35 | 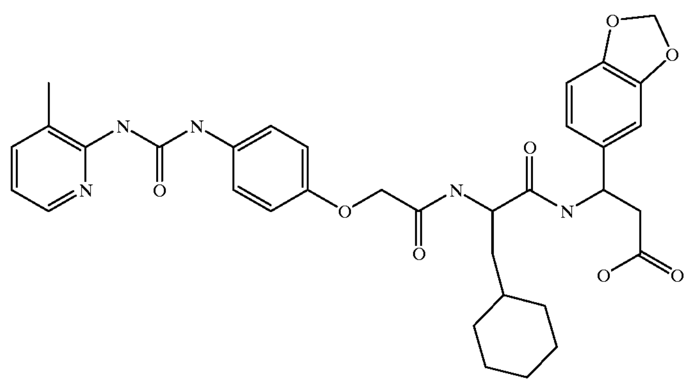 | A1 | | K | | 645.5 | 0.65–0.8(2H, m), 0.9–1.15(4H, m), 1.2–1.4 (2H, m), 1.5–1.65(5H, m), 2.2(3H, s), 2.5– 2.7(2H, m), 4.2–4.4(1H, m), 4.55(2H, s), 5.0–5.1(1H, m), 5.95(2H, s), 6.65–6.95(6H, m), 7.05 7.15(2H, m), 7.3–7.4(2H, d), 7.75– 7.8(1H, d), 7.85–7.95(2H, m), 8.5(1H, d), 8.95(1H, s) | Dynamax 60A C18 | MeCN/ H2O 20-80 | 16.5 |

TABLE 1-continued

| Ex. No | Structure | Synthetic Method Code Urea Formation | Final ester Hydrolysis | Methods for Intermediates | ESPMS M−H | M+H | NMR 1H, ppm. d6-DMSO | Reverse Phase HPLC (Run Time = 20 min.) Column Type | Solvent + 0.1% TFA | Rt. min |
|---|---|---|---|---|---|---|---|---|---|---|
| 36 | 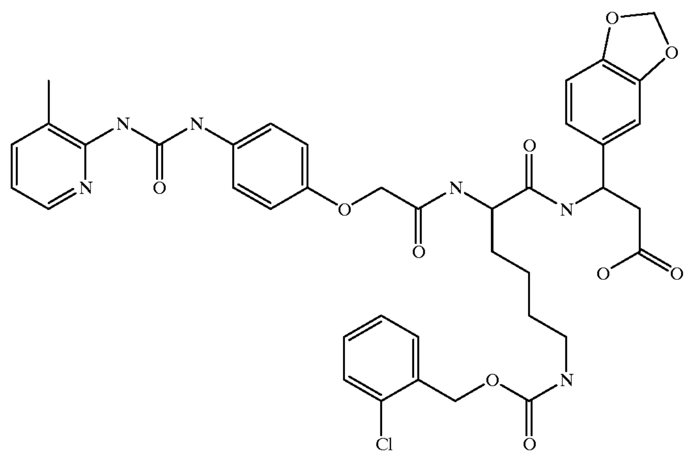 | A1 | K | | | 786.3 | 1.0–1.2(2H, m), 1.2–1.4(2H, m), 1.4–1.6 (2H, m), 2.2(3H, s), 2.5–2.7(2H, m), 2.8–3.0 (2H, b), 4.2–4.4(1H, m), 4.5(2H, s), 5.0–5.1 (3H, m), 5.9(2H, s), 6.7–6.9(6H, m), 7.0–7.1 (2H, m), 7.2–7.3(1H, m), 7.3–7.4(4H, m), 7.4–7.5(2H, m), 7.8(2H, m), 7.9(1H, d), 8.5 (1H, d), 8.95(1H, s) | Dynamax 60A C18 | MeCN/ H2O 20-80 | 16.7 |
| 37 | 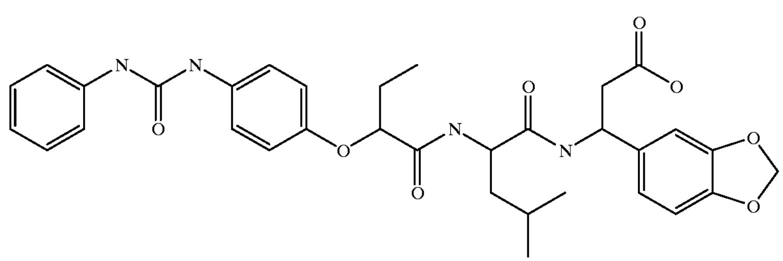 | A1 | K | | | 629 | 0.8(m), 6H; 1.4(m), 3H; 1.9(m); 1H, 2.1(m), 2H; 2.2(s), 3H; 2.6(m), 2H; 2.8(m); 1H; 4.4 (m), 1H; 4.5(m), 1H; 5.05(m), 1H; 5.95(s), 2H; 6.8(m), 5H; 7.1(m), 4H; 7.6(d) & 7.8 (d), 1H; 7.75(m), 2H; 8.4(d) & 8.5(d), 1H; 8.8(s), 1H | | | |

TABLE 1-continued

| Ex. No | Structure | Synthetic Method Code Urea Formation | Final ester Hydrolysis | Methods for Intermediates | ESPMS M−H | M+H | NMR 1H, ppm. d6-DMSO | Reverse Phase HPLC (Run Time = 20 min.) Column Type | Solvent + 0.1% TFA | Rt. min. |
|---|---|---|---|---|---|---|---|---|---|---|
| 38 | 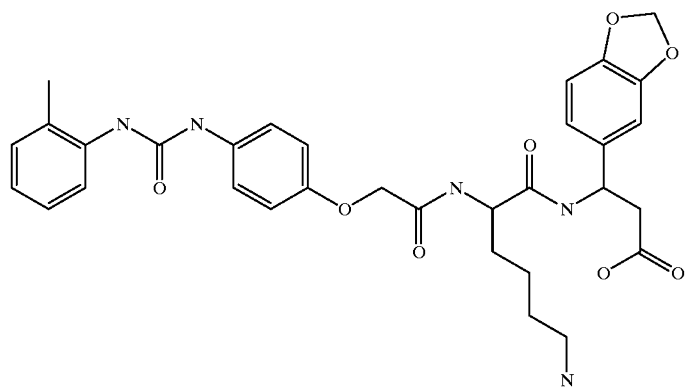 | A1 | | K | | 620.3 | 1.0–1.2(2H, m), 1.4–1.6(4H, m), 2.2(3H, s), 2.5–2.7(4H, m), 4.2–4.4(1H, m), 4.55(2H, s), 5.0–5.1(1H, m), 5.95(2H, s), 6.65–6.95 (6H, m), 7.1–7.2(2H, m), 7.4(2H, d), 7.7 (2H, b), 7.8(1H, d), 7.9(1H, d), 8.1(1H, s), 8.5(1H, d), 8.95(1H, s) | Dynamax 60A C18 | MeCN/ H2O 20-80 | 10.5 |
| 39 | 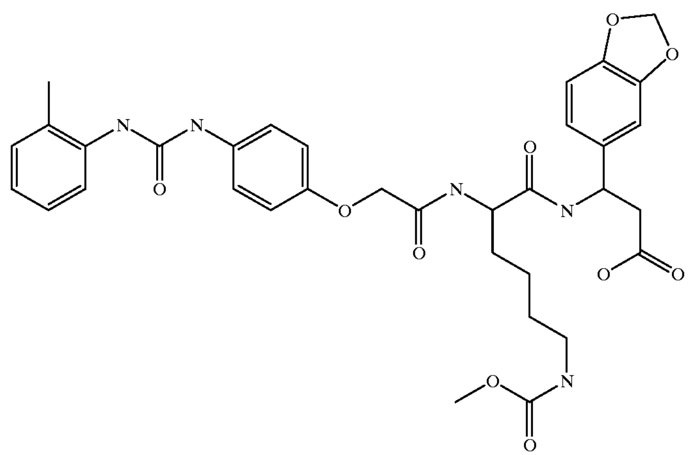 | A1 | | K | | 676.4 | 1.0–1.2(2H, m), 1.2–1.4(2H, m), 1.4–1.6 (2H, m), 2.2(3H, s), 2.5–2.7(2H, m), 2.8–2.9 (2H, m), 3.3(3H, s), 4.3(1H, m), 4.6(2H, s), 5.0–5.1(1H, m), 5.95(2H, s), 6.7–7.0(6H, m), 7.0–7.1(2H, m), 7.3–7.4(2H, d), 7.7–7.8 (2H, d), 7.8–7.9(1H, d), 8.5(1H, d), 8.95 (1H, s) | Dynamax 60A C18 | MeCN/ H2O 20-80 | 12.8 |

TABLE 1-continued

| Ex. No | Structure | Synthetic Method Code Final Urea Formation | Synthetic Method Code ester Hydrolysis | Methods for Intermediates | ESPMS M−H | ESPMS M+H | NMR 1H, ppm. d6-DMSO | Reverse Phase HPLC (Run Time = 20 min.) Column Type | Reverse Phase HPLC Solvent + 0.1% TFA | Reverse Phase HPLC Rt. min. |
|---|---|---|---|---|---|---|---|---|---|---|
| 40 | 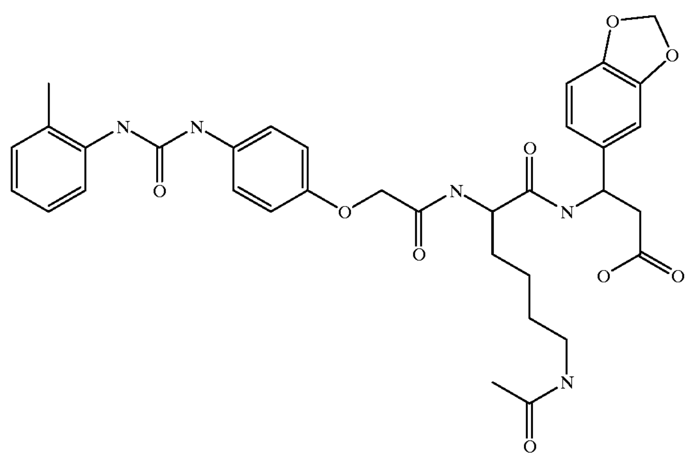 | A1 | | K | 660.4 | | 1.0–1.2(2H, m), 1.2–1.4(2H, m), 1.4–1.6 (2H, m), 1.8(3H, s), 2.2(3H, s), 2.5–2.7(2H, m), 2.8–2.9(2H, m), 4.3(1H, m), 4.5(2H, s), 5.0–5.1(1H, m), 5.95(2H, s), 6.7–7.0(5H, m), 7.0–7.1(2H, m), 7.3–7.4(2H, d), 7.7(1H, m), 7.8–7.85(2H, d), 7.8–7.9(1H, d), 8.5(1H, d), 8.95(1H, s) | Dynamax 60A C18 | MeCN/ H2O 20–80 | 11.6 |
| 41 | 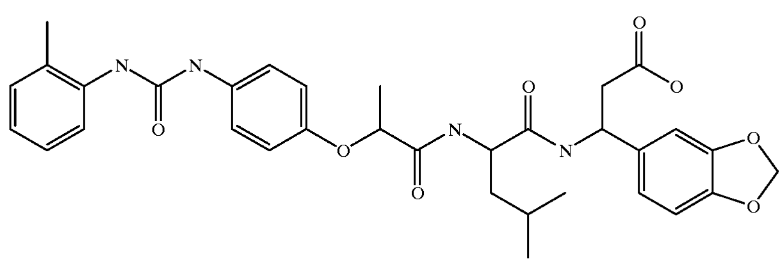 | A1 | | K | 617 | | 0.8(q), 6H; 1.4(m), 6H; 2.2(s), 3H; 2.6(m), 2H; 4.3, (m), 1H; 4.7(q), 1H; 5.05(q), 1H; 5.95(s), 2H; 6.7(d), 1H; 6.8(t), 4H; 6.9(t), 1H; 7.1(m), 2H; 7.3(d), 2H; 7.8(m), 2H; 8.05(d), 1H; 8.4(d), 1H; 8.9(s), 1H | | | |

TABLE 1-continued

| Ex. No | Structure | Synthetic Method Code Urea Formation | Final ester Hydrolysis | Methods for Intermediates | ESPMS M−H | M+H | NMR 1H, ppm. d6-DMSO | Reverse Phase HPLC (Run Time = 20 min.) Column Type | Solvent + 0.1% TFA | Rt. min |
|---|---|---|---|---|---|---|---|---|---|---|
| 42 | 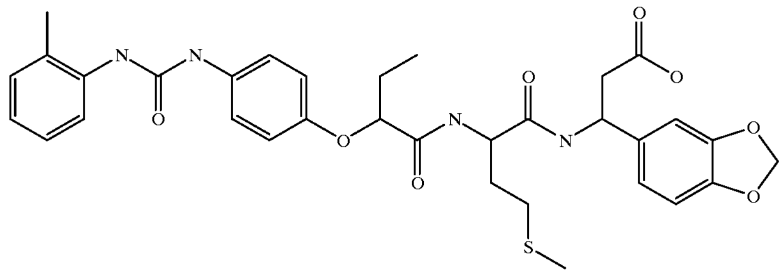 | A1 | | K | 649 | | 0.9(t), 3H; 1.8(m), 5H; 1.8(s) & 1.95(s), 3H; 2.05(m), 1H; 2.2(s), 3H; 2.6(m), 2H; 4.4 (m), 1H; 4.5(m), 1H; 5.05(m), 1H; 5.95(s), 2H; 6.8(m), 6H; 7.1(m), 2H; 7.3(m), 2H; 7.8 (m), 2H; 7.9(d) & 8.1(d), 1H; 8.3(d) & 8.4 (d), 1H; 8.8(d), 1H | | | |
| 43 | 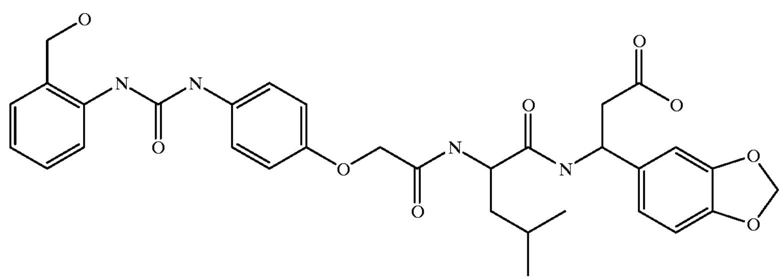 | B | | K | 619 | | 0.7–0.9(6H, m), 1.3–1.5(3H, m), 2.5–2.7 (2H, m), 4.2–4.4(1H, m), 4.5(2H, s), 4.55 (2H, d), 4.9–5.1(1H, m), 5.3(1H, b), 5.9(2H, s), 6.6–6.9(5H, m), 6.9–7.0(1H, t), 7.1–7.2 (1H, t), 7.2–7.3(1H, d), 7.3–7.4(2H, d), 7.8 (1H, d), 8.0(1H, d), 8.1(1H, s), 8.5(1H, d), 9.1(1H, s) | Dynamax 60A C18 | MeCN/ H2O 20–80 | 12.5 |
| 44 | 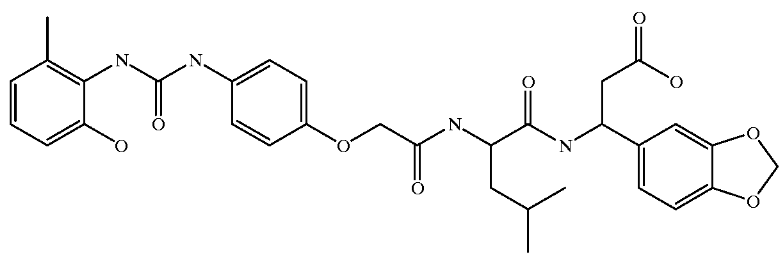 | B | | K | 619 | | 0.7–0.9(6H, m), 1.3–1.5(3H, m), 2.1(3H, s), 2.5–2.7(2H, m), 4.2–4.4(1H, m), 4.5(2H, s), 4.9–5.1(1H, m), 5.9(2H, s), 6.6–6.9(7H, m), 7.3–7.4(2H, d), 7.5(1H, s), 8.0(1H, d), 8.4– 8.5(1H, d), 8.7(1H, s), 9.4(1H, s) | Dynamax 60A C18 | MeCN/ H2O 20–80 | 13.4 |

TABLE 1-continued

| Ex. No | Structure | Synthetic Method Code - Urea Formation | Synthetic Method Code - Final ester Hydrolysis | Methods for Intermediates | ESPMS M−H | ESPMS M+H | NMR 1H, ppm. d6-DMSO | Reverse Phase HPLC Column Type | Solvent + 0.1% TFA | Rt. min. (Run Time = 20 min.) |
|---|---|---|---|---|---|---|---|---|---|---|
| 45 | 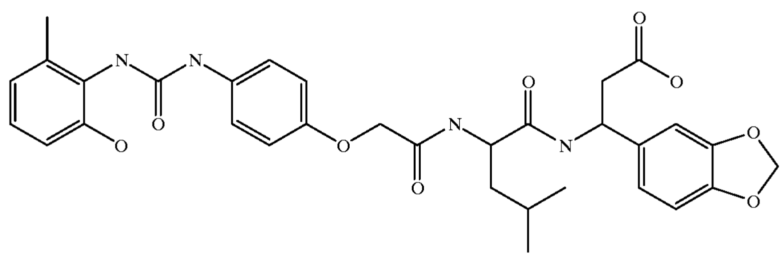 | B | | K | | 617 | 0.9–1.1(6H, m), 1.5–1.7(3H, m), 2.35(6H, s), 2.6–2.7(2H, m), 4.4–4.6(1H, m), 4.65 (2H, s), 5.1–5.2(1H, m), 6.1(2H, s), 6.9–7.1 (5H, m), 7.2(3H, m), 7.5–7.6(2H, d), 8.1– 8.2(1H, d), 8.6(1H, s), 9.1–9.3(1H, d), 9.5 (1H, s) | Dynamax 60A C18 | MeCN/ H2O 20-80 | 11.7 |
| 46 | 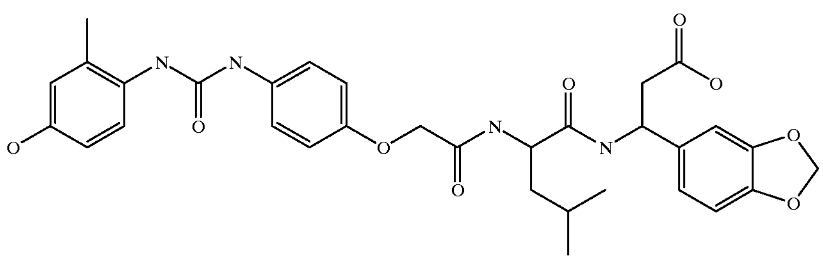 | B | | K | | 619 | 0.7–0.9(6H, m), 1.3–1.5(3H, m), 2.1(3H, s), 2.5–2.7(2H, m), 4.2–4.4(1H, m), 4.5(2H, s), 4.9–5.1(1H, m), 5.9(2H, s), 6.4–6.6(2H, m), 6.6–6.9(5H, m), 7.3–7.4(3H, d), 7.6(1H, s), 8.0(1H, d), 8.4(1H, s), 8.5(1H, s), 9.0 (1H, s) | Dynamax 60A C18 | MeCN/ H2O 20-80 | 16.5 |
| 47 | 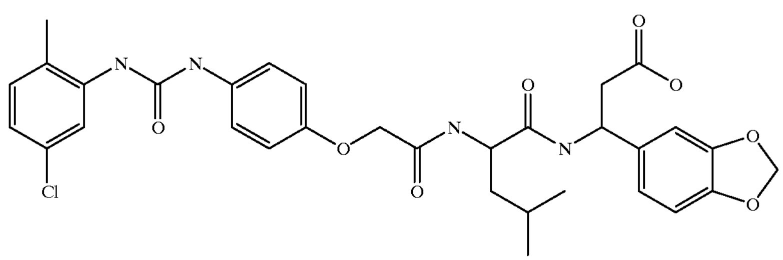 | B | | K | | 637 | 0.7–0.9(6H, m), 1.3–1.5(3H, m), 2.2(3H, s), 2.5–2.7(2H, m), 4.2–4.4(1H, m), 4.5(2H, s), 4.9–5.1(1H, m), 5.9(2H, s), 6.6–6.9(5H, m), 6.9–7.0(1H, m), 7.1(1H, d), 7.3–7.4(2H, d), 8.0(2H, d), 8.4(1H, s), 8.7(1h, m), 9.3 (1H, s) | Dynamax 60A C18 | MeCN/ H2O 20-80 | 14.5 |

| Ex. No | Structure | Synthetic Method Code Urea Formation | Final ester Hydrolysis | Methods for Intermediates | ESPMS M−H | M+H | NMR 1H, ppm, d6-DMSO | Reverse Phase HPLC (Run Time = 20 min.) | | |
|---|---|---|---|---|---|---|---|---|---|---|
| | | | | | | | | Column Type | Solvent + 0.1% TFA | Rt. min |
| 48 | 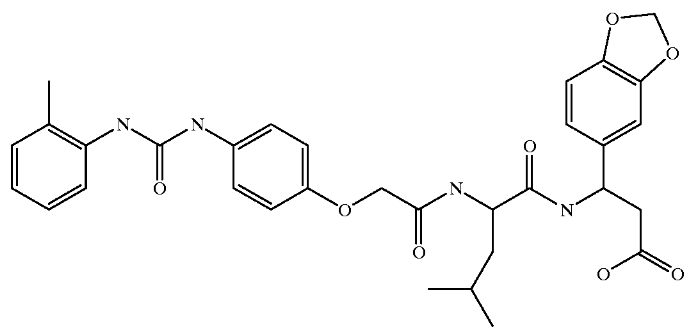 | A1 | K | | 619.4 | | 0.7–0.9(6H, m), 1.2–1.4(1H, m), 1.4–1.6 (2H, t), 2.2(3H, s), 2.5–2.7(2H, m), 2.8(3H, s), 4.7–4.9(2H, m), 4.9–5.0(1H, m), 5.0–5.1 (1H, m), 5.95(2H, s), 6.7–7.0(6H, m), 7.0–7.2(2H, m), 7.2–7.4(2H, d), 7.8–7.9(2H, m), 8.2(1H, d), 8.8(1H, s) | Dynamax 60A C18 | MeCN/ H2O 20-80 | 15.1 |
| 49 | 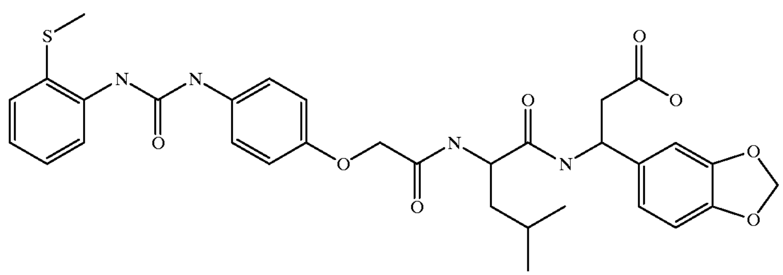 | C1 | K | | 635 | | 0.7–0.9(6H, m), 1.3–1.5(3H, m), 2.4(3H, m), 2.5 2.7(2H, m), 4.2–4.4(1H, m), 4.5(2H, s), 4.9–5.1(1H, m), 5.9(2H, s), 6.6–6.9(5H, m), 7.0–7.1(1H, m), 7.1–7.2(3H, t), 7.3–7.4 (3H, m), 7.9(2H, d), 8.1(1h, s), 8.5(1H, d), 9.2(1H, s) | Dynamax 60A C18 | MeCN/ H2O 20-80 | 15.5 |

TABLE 1-continued

| Ex. No | Structure | Synthetic Method Code Urea Formation | Final ester Hydrolysis | Methods for Intermediates | ESPMS M−H | M+H | NMR 1H, ppm. d6-DMSO | Column Type | Solvent + 0.1% TFA | Rt. min |
|---|---|---|---|---|---|---|---|---|---|---|
| 50 | *structure with 2-methyl-3-fluorophenyl urea* | C1 | K | | 621 | | 0.7–0.9(6H, m), 1.3–1.5(3H, m), 2.1(3H, m), 2.5 2.7(2H, m), 4.2–4.4(1H, m), 4.5(2H, s), 4.9–5.1(1H, m), 5.9(2H, s), 6.6–6.9(6H, m), 7.1(1H, m), 7.3–7.4(2H, d), 7.6(1H, d), 8.0(1H, d), 8.1(1H, s), 8.5(1H, m), 9.0(1H, s) | Dynamax 60A C18 | MeCN/ H2O 20–80 | 15.3 |
| 51 | *structure with benzothiazol-2-yl urea* | C1 | K | | 646 | | 0.7–0.9(6H, m), 1.3–1.5(3H, m), 2.5–2.7(2H, m), 4.2–4.4(1H, m), 4.5(2H, s), 4.9–5.1(1H, m), 5.9(2H, s), 6.6–6.9(5H, m), 7.2(1H, t), 7.3–7.4(3H, m), 7.6(1H, d), 7.9(1H, d), 8.0(1H, d), 8.5(1H, d), 9.0(1H, d), 11.0–12.5(2H, b) | Dynamax 60A C18 | MeCN/ H2O 20–80 | 15.4 |
| 52 | *structure with 5-methylisoxazol-3-yl urea* | C1 | K | | 594 | | 0.7–0.9(6H, m), 1.3–1.5(3H, m), 2.3(3H, s), 2.5–2.7(2H, m), 4.2–4.4(1H, m), 4.5(2H, s), 4.9–5.1(1H, m), 5.9(2H, s), 6.5(1H, s), 6.6–6.9(5H, m), 7.3–7.4(2H, d), 8.0(1H, d), 8.4(1H, d), 8.7(1H, s), 9.4(1H, s) | Dynamax 60A C18 | MeCN/ H2O 20–80 | 13.1 |

TABLE 1-continued

| Ex. No | Structure | Synthetic Method Code - Urea Formation | Synthetic Method Code - Final ester Hydrolysis | Methods for Intermediates | ESPMS M-H | ESPMS M+H | NMR 1H, ppm. d6-DMSO | Reverse Phase HPLC Column Type | Solvent + 0.1% TFA | Rt. min. |
|---|---|---|---|---|---|---|---|---|---|---|
| 53 | 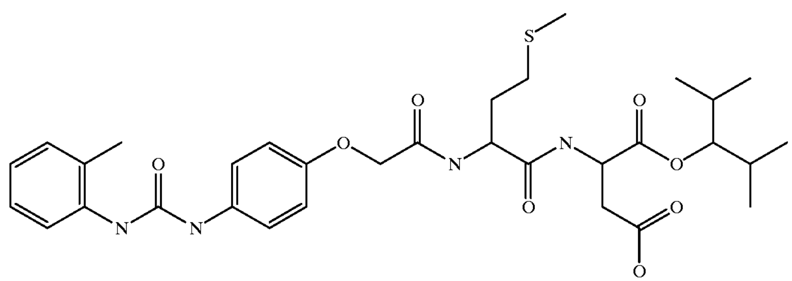 | A1 | | L | 643 | | 0.75(m, 12H); 1.1.75–1.95(m, 4H); 2.0(s, 3H); 2.2(s, 3H); 2.3–2.6(m, 4H); 4.4–4.55 (m, 4H); 4.6(q, 1H); 6.8–6.9(m, 3H); 7.0–7.2(m, 2H); 7.35(d, 2H); 7.75(d, 1H); 8.05 (d, 1H); 8.25(s, 1H); 8.6(d, 1H); 9.25(s, 1H). | | | |
| 54 | 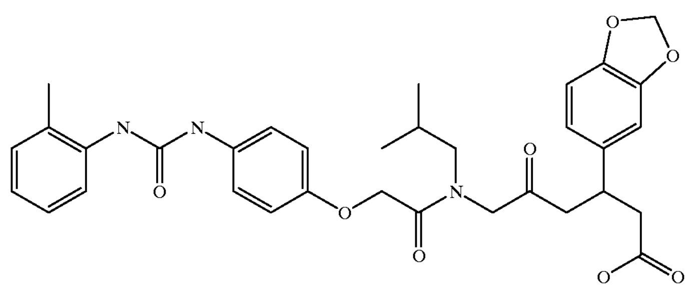 | A1 | | K | 605.3 | | 0.7–0.9(6H, m), 1.7–1.9(1H, m), 2.2(3H, s), 2.5–2.7(2H, m), 2.8(2H, s), 3.0–3.2(2H, m), 3.9(2H, d) 4.7(2H, d) 4.9–5.0(1H, m), 4.9–5.0(1H, m), 5.0–5.1(1H, m), 5.95(2H, s), 6.7–7.0(6H, m), 7.0–7.2(2H, m), 7.2–7.4 (2H, m), 7.8 7.9(2H, m), 8.5(1H, d), 8.8 (1H, s) | Dynamax 60A C18 | MeCN/ H2O 20-80 | 14.0 |
| 55 | 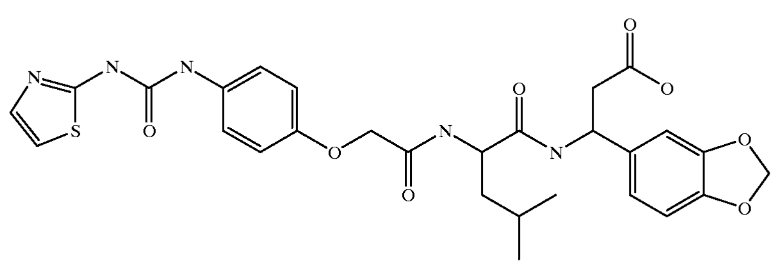 | C1 | | K | 596 | | 0.7–0.9(6H, m), 1.3–1.5(3H, m), 2.5–2.7 (2H, m), 4.2–4.4(1H, m), 4.5(2H, s), 4.9–5.1 (1H, m), 5.9(2H, s), 6.6–6.9(5H, m), 7.1(1H, s), 7.3–7.4(3H, m), 8.0(1H, d), 8.4(1H, d), 8.8(1H, s) | Dynamax 60A C18 | MeCN/ H2O 20-80 | 12.5 |

TABLE 1-continued

| Ex. No | Structure | Synthetic Method Code Urea Formation | Synthetic Method Code Final ester Hydrolysis | Methods for Intermediates | ESPMS M−H | ESPMS M+H | NMR 1H, ppm. d6-DMSO | Reverse Phase HPLC (Run Time = 20 min.) Column Type | Reverse Phase HPLC Solvent + 0.1% TFA | Reverse Phase HPLC Rt. min |
|---|---|---|---|---|---|---|---|---|---|---|
| 56 | 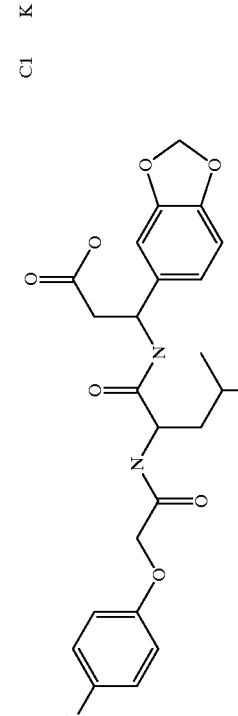 | C1 | K | | | 642 | 0.7–0.9(6H, m), 1.3–1.5(3H, m), 2.5–2.7 (2H, m), 4.2–4.4(1H, m), 4.5(2H, s), 4.9–5.1 (1H, m), 5.9(2H, s), 6.6–6.9(5H, m), 7.3–7.4 (2H, d), 7.4(1H, b), 7.5(2H, d), 7.6(1H, t), 7.8(2H, t), 8.0(2H, m), 8.2(1H, b), 8.4(1H, d), 8.6(1H, d), 9.8(1H, b) | Dynamax 60A C18 | MeCN/ H2O 20-80 | 12.9 |
| 57 | 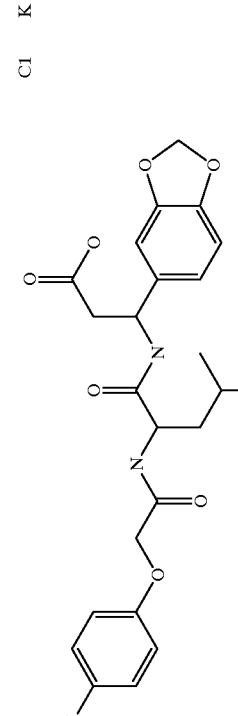 | C1 | K | | | 603 | 0.7–1.9(6H, m), 1.3–1.5(3H, m), 2.5–2.7 (2H, m), 3.2(3H, s), 4.2–4.4(1H, m), 4.5(2H, s), 4.9–5.1(1H, m), 5.9(2H, s), 6.6–6.9(5H, m), 7.2–7.4(7H, m), 8.0(1H, d), 8.1(1H, s), 8.5(1H, d) | Dynamax 60A C18 | MeCN/ H2O 20-80 | 15.7 |
| 58 | 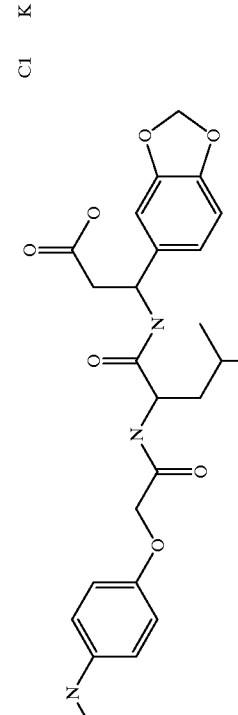 | C1 | K | | | 643 | 0.7–0.9(6H, m), 1.3–1.5(3H, m), 2.5–2.7 (2H, m), 3.5(3H, s), 4.2–4.4(1H, m), 4.5(2H, s), 4.9–5.1(1H, m), 5.9(2H, s), 6.6–6.9(5H, m), 7.0–7.2(2H, m), 7.3–7.4(2H, m), 7.5 (2H, d), 8.0(1H, d), 8.4(1H, d) | Dynamax 60A C18 | MeCN/ H2O 20-80 | 12.8 |

TABLE 1-continued

| Ex. No | Structure | Synthetic Method Code Final Urea For-ma-tion | Synthetic Method Code ester Hy-drol-ysis | Methods for Inter-mediates | ESPMS M−H | ESPMS M+H | NMR 1H, ppm, d6-DMSO | Reverse Phase HPLC (Run Time = 20 min.) Column Type | Solvent + 0.1% TFA | Rt. min. |
|---|---|---|---|---|---|---|---|---|---|---|
| 59 | 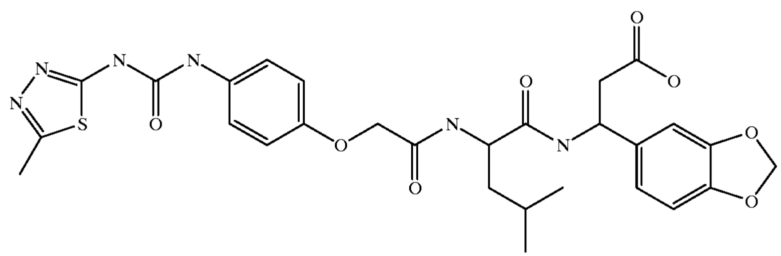 | C1 | | K | 611 | 613 | 0.7–0.9(6H, m), 1.3–1.5(3H, m), 2.5(3H, s), 2.5–2.7(2H, m), 4.2–4.4(1H, m), 4.5(2H, s), 4.9–5.1(1H, m), 5.9(2H, s), 6.6–6.9(5H, m), 7.3–7.4(2H, d), 8.0(1H, d), 8.4(1H, d), 9.0(1H, s) | Dynamax 60A C18 | MeCN/ H2O 20-80 | 12.3 |
| 60 | 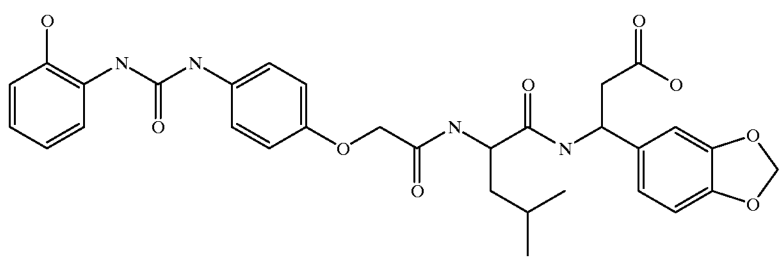 | C1 | | K | 605 | | 0.7–0.9(6H, m), 1.3–1.5(3H, m), 2.5–2.7(2H, m), 4.2–4.4(1H, m), 4.5(2H, s), 4.9–5.1(1H, m), 5.9(2H, s), 6.6–7.0(8H, m), 7.3–7.4(2H, d), 7.9(1H, d), 8.0(1H, s), 8.1(1H, s), 8.4(1H, d), 9.0(1H, s), 9.8(1H, s) | Dynamax 60A C18 | MeCN/ H2O 20-80 | 14.7 |
| 61 | 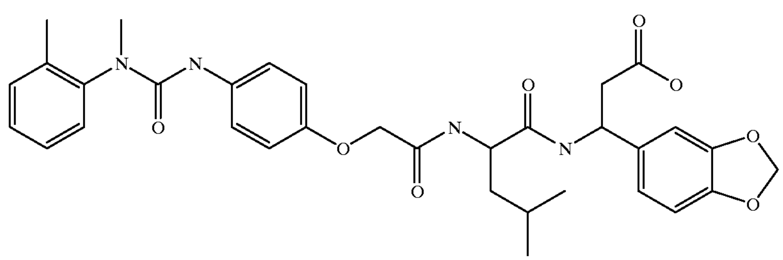 | B | | K | 617 | | 0.7–0.9(6H, m), 1.3–1.5(3H, m), 2.2(3H, s), 2.5–2.7(2H, m), 3.1(3H, s), 4.2–4.4(1H, m), 4.5(2H, s), 4.9–5.1(1H, m), 5.9(2H, s), 6.6–6.9(5H, m), 7.3–7.4(6H, m), 7.5(1H, s), 8.0(1H, d), 8.4(1H, s) | Dynamax 60A C18 | MeCN/ H2O 20-80 | 16.3 |

TABLE 1-continued

| Ex. No | Structure | Synthetic Method Code - Urea Formation | Synthetic Method Code - Final ester Hydrolysis | Methods for Intermediates | ESPMS M−H | ESPMS M+H | NMR 1H, ppm, d6-DMSO | Reverse Phase HPLC Column Type | Reverse Phase HPLC Solvent + 0.1% TFA | Rt. min. |
|---|---|---|---|---|---|---|---|---|---|---|
| 62 | 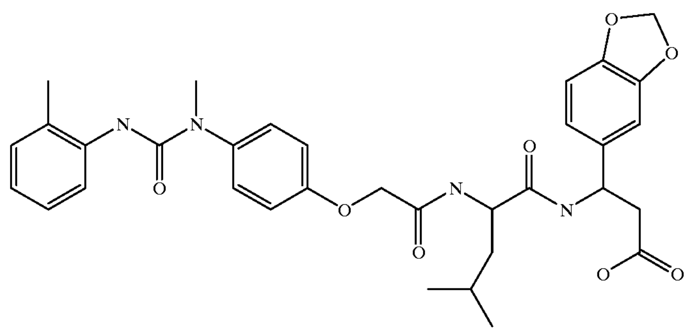 | A1 | K | | 619.5 | | 0.7–0.9(6H, m), 1.3–1.5(3H, m), 2.0(3H, s), 2.5–2.7(2H, m), 3.2(3H, s), 4.3–4.4(1H, m), 4.6(2H, s), 5.0–5.1(1H, m), 5.95(2H, s), 6.7–7.1(9H, m), 7.2–7.3(2H, m), 7.4–7.5(1H, d), 8.1–8.2(1H, d), 8.5–8.6(1H, d) | Dynamax 60A C18 | MeCN/ H2O 20–80 | 15.9 |
| 63 | 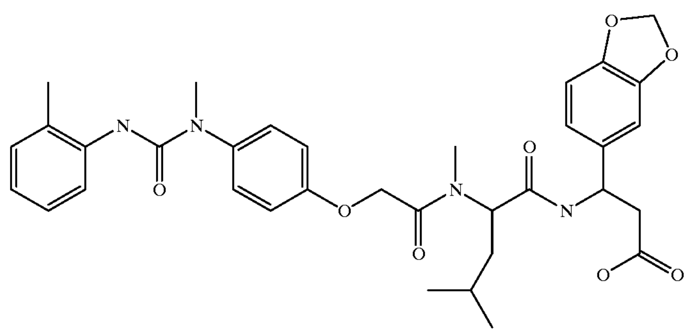 | A1 | K | | 633.5 | | 0.7–0.9(6H, m), 1.3–1.5(3H, m), 2.0(3H, s), 2.5–2.7(2H, m), 2.8(3H, s), 3.2(3H, s), 4.3–4.4(1H, m), 4.8–5.0(2H, m), 5.0–51(1H, m), 5.95(2H, s), 6.7–7.0(7H, m), 7.0–7.1(2H, m), 7.2–7.3(2H, m), 7.4–7.5(1H, d), 8.1–8.2(1H, d) | Dynamax 60A C18 | MeCN/ H2O 20–80 | 16.8 |

TABLE 1-continued

| Ex. No | Structure | Synthetic Method Code | | | ESPMS | | NMR 1H, ppm. d6-DMSO | Reverse Phase HPLC (Run Time = 20 min.) | | |
|---|---|---|---|---|---|---|---|---|---|---|
| | | Urea Formation | Final ester Hydrolysis | Methods for Intermediates | M − H | M + H | | Column Type | Solvent + 0.1% TFA | Rt. min. |
| 64 | 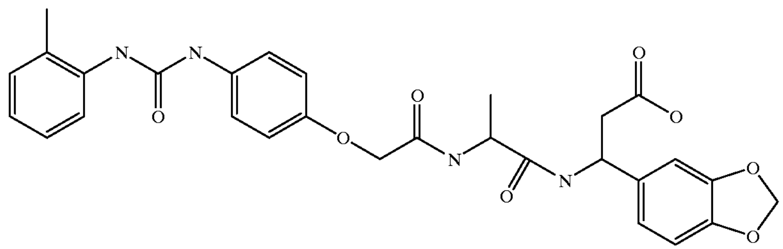 | A1 | K | | 561 | | 1.2(d), 3H; 2.2(s), 3H; 2.6(m), 2H; 4.3(m), 1H; 4.4(s), 2H; 5.1(m), 1H; 5.95(s), 2H; 6.8 (m), 6H; 7.1(m), 2H; 7.3(d), 2H; 7.8(d), 1H; 7.85(s); 1H; 7.95(d), 1H; 8.4(d), 1H; 8.9 (s), 1H | | | |
| 65 | 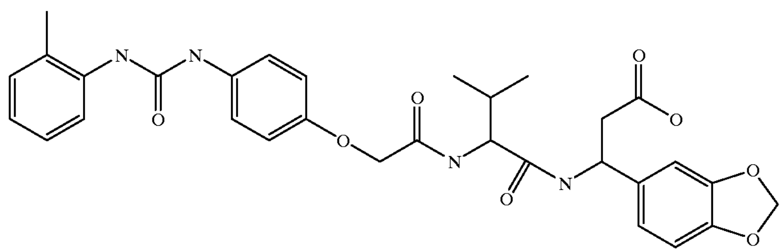 | A1 | K | | 589 | | 0.7(d), 3H; 2.2(s), 3H; 2.6(m), 2H; 4.2(m), 1H; 4.6(s), 1H; 5.05(q), 1H; 5.95(s), 2H; 6.8 (m), 6H; 7.05(m), 2H; 7.4(d), 2H; 7.7(d); 1H; 7.8(s), 2H; 8.5(d), 1H; 8.8(s), 1H | | | |
| 66 | 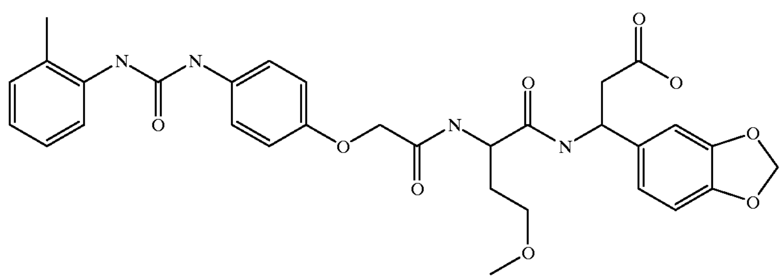 | A1 | K | | 607.4 | | 8.80(s, 1H), 8.46(d, 1H), 8.00(d, 1H), 7.80 (d, 2H), 7.36(d, 2H), 7.08–7.18(m, 2H), 6.72–6.96(m, 6H), 5.98(s, 2H), 5.10(q, 1H), 4.48(d, 2H), 4.3–4.5(m, 1H), 3.18–3.24(t, 2H), 3.12(s, 3H), 2.58–2.75(m, 2H), 2.14(s, 3H), 1.70–1.90(m, 2H) | Dynamax 60A C18 | MeCN/ H2O 20-80 | 12.9 |

TABLE 1-continued

| Ex. No | Structure | Synthetic Method Code Urea Formation | Synthetic Method Code Final ester Hydrolysis | Methods for Intermediates | ESPMS M−H | ESPMS M+H | NMR 1H, ppm, d6-DMSO | Reverse Phase HPLC (Run Time = 20 min.) Column Type | Solvent + 0.1% TFA | Rt. min |
|---|---|---|---|---|---|---|---|---|---|---|
| 67 | 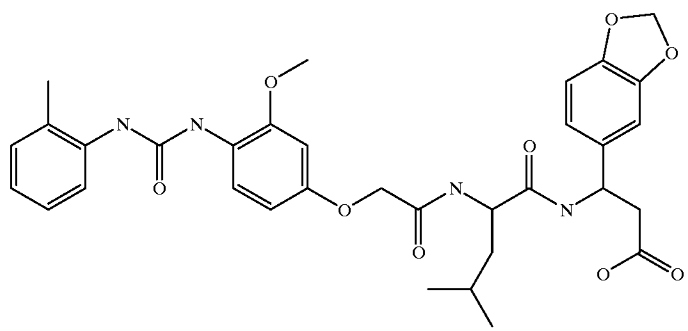 | A1 | | K | 633 | 635 | 0.7–0.9(6H, m), 1.3–1.5(3H, m), 2.2(3H, s), 2.5–2.7(2H, m), 3.8(3H, s), 4.2–4.4(1H, m), 4.5(2H, s), 4.9–5.1(1H, m), 5.9(2H, s), 6.4–6.5(1H, dd), 6.6–7.0(5H, m), 7.0–7.2(2H, m), 7.8(1H, d), 7.9(1H, d), 8.0(1H, d), 8.4–8.5(2H, d) | Dynamax 60A C18 | MeCN/ H2O 20-80 | 16.8 |
| 68 | 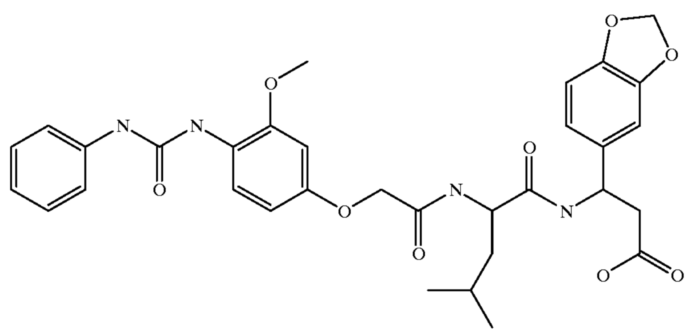 | A1 | | K | 619.4 | 621.4 | 0.7–0.9(6H, m), 1.3–1.5(3H, m), 2.5–2.7 (2H, m), 3.8(3H, s), 4.3–4.4(1H, m), 4.6(2H, s), 5.0–5.1(1H, m), 5.95(2H, s), 6.4–6.5(1H, dd), 6.7–7.0(5H, m), 7.2–7.3(2H, t), 7.4–7.5 (2H, d), 7.9(2H, d), 8.0(1H, s), 8.5–8.6(1H, d), 9.1(1H, s) | Dynamax 60A C18 | MeCN/ H2O 20-80 | 16.6 |

TABLE 1-continued

| Ex. No | Structure | Synthetic Method Code - Urea Formation | Synthetic Method Code - Final ester Hydrolysis | Methods for Intermediates | ESPMS M−H | ESPMS M+H | 1H NMR, ppm. d6-DMSO | Reverse Phase HPLC Column Type | Solvent + 0.1% TFA | Rt. min |
|---|---|---|---|---|---|---|---|---|---|---|
| 69 | 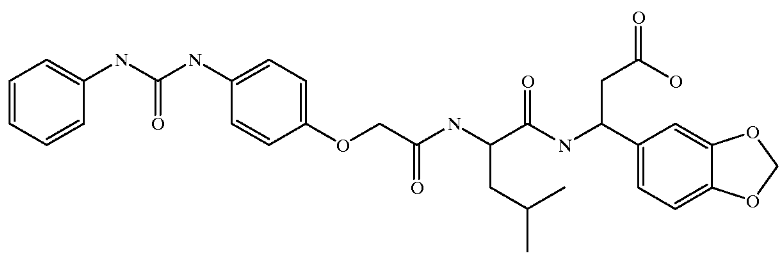 | C2 | K | | 590.4 | | 0.78(6H, t); 1.39(3H, m); 2.63(2H, m); 4.37 (1H, m); 4.47(2H, s); 5.06(1H, q); 5.95(2H, s); 6.72(1H, d); 6.81(1H, d); 6.84(1H, s); 6.89(2H, d); 7.36(3H, m); 7.93(2H, t); 8.18 (1H, d); 8.45(1H, d); 8.63(1H, d); 8.70(1H, s); 8.91(1H, s) | Waters spherisorb S5ODS2 | 80/20 MeOH/ H2O | 4.14 ELS, 4.43 u.v. |
| 70 | 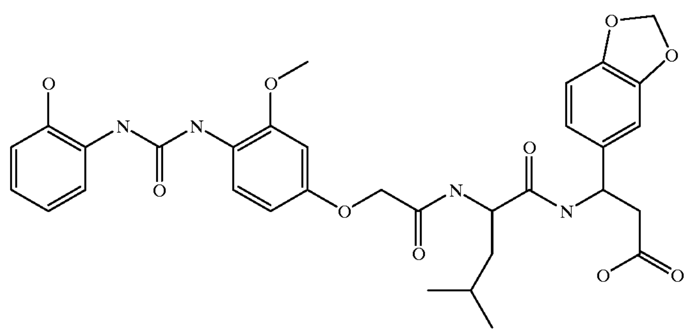 | A1 | K | Q | 653.3 | 655.3 | 0.7–0.9(6H, m), 1.3–1.5(3H, m), 2.5–2.7 (2H, m), 3.8(3H, s), 4.3–4.4(1H, m), 4.6(2H, s), 5.0–5.1(1H, m), 5.95(2H, s), 6.4(1H, dd), 6.6–6.8(3H, m), 6.9(1H, s), 7.0–7.1(1H, t), 7.2(1H, t), 7.4–7.5(1H, d), 7.8(1H, d), 8.1–8.2(2H, m), 8.8(2H, d), 9.0(1H, d) | Dynamax 60A C18 | MeCN/ H2O 20-80 | 18.1 |

TABLE 1-continued

| Ex. No | Structure | Synthetic Method Code Urea Formation | Final ester Hydrolysis | Methods for Intermediates | ESPMS M−H | M+H | NMR 1H, ppm, d6-DMSO | Reverse Phase HPLC (Run Time = 20 min.) Column Type | Solvent + 0.1% TFA | Rt. min. |
|---|---|---|---|---|---|---|---|---|---|---|
| 71 | 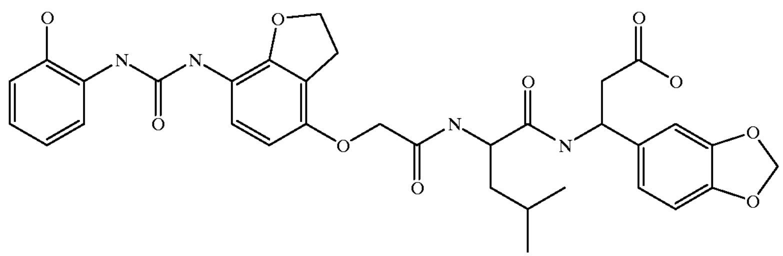 | A1 | K | P | 645 | | 0.7–0.9(6H, m), 1.3–1.5(3H, m), 2.2(3H, s), 2.5–2.7(2H, m), 3.2(2H, t), 4.2–4.4(1H, m), 4.5(2H, s), 4.6(2H, t), 4.9–5.1(1H, m), 5.9 (2H, s), 6.4(1H, d), 6.6–6.9(4H, m), 7.1–7.2 (2H, m), 7.7(1H, d), 7.8(2H, t), 8.2(1H, s), 8.4(1H, s), 8.5(1H, d) | Dynamax 60A C18 | MeCN/ H2O 20-80 | 16.8 |
| 72 | 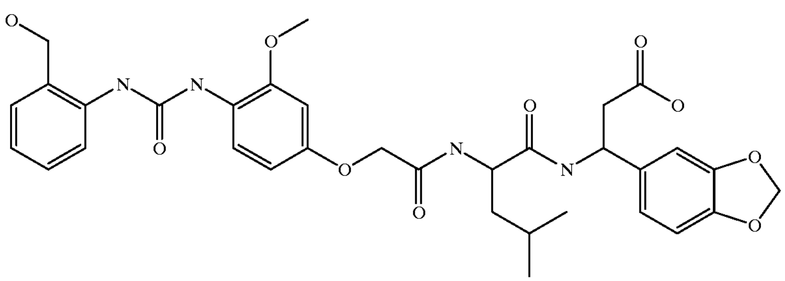 | A1 | K | Q | 649 | | 0.7–0.9(6H, m), 1.3–1.5(3H, m), 2.5–2.7 (2H, m), 3.8(3H, s), 4.2–4.4(1H, m), 4.5(4H, s), 4.9–5.1(2H, m), 5.9(2H, s), 6.5(1H, dd), 6.6–6.9(4H, m), 7.0(1H, t), 7.2(1H, t), 7.3 (1H, d), 7.8(1H, d), 7.9(1H, d), 8.0(1H, d), 8.3(1H, s), 8.4(1H, s), 8.5(1H, d) | Dynamax 60A C18 | MeCN/ H2O 20-80 | 14.2 |
| 73 | 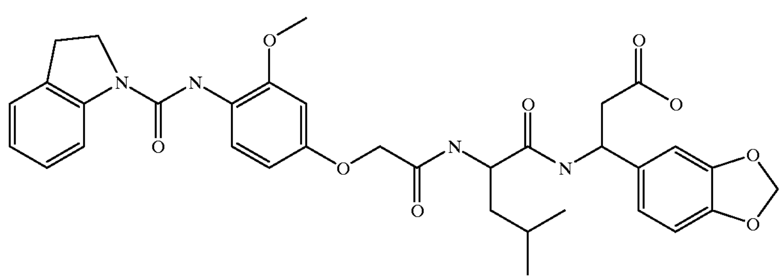 | B | K | Q | 645 | | 0.7–0.9(6H, m), 1.3–1.5(3H, m), 2.5–2.7 (2H, m), 3.2(2H, t), 3.8(3H, s), 4.0(2H, t), 4.2–4.4(1H, m), 4.5(2H, s), 4.9–5.1(1H, m), 5.9(2H, s), 6.5(1H, dd), 6.6–7.0(5H, m), 7.1 (1H, t), 7.2(1H, d), 7.5(1H, d), 7.6(1H, s), 7.8(1H, d), 8.0(1H, d), 8.5(1H, d) | Dynamax 60A C18 | MeCN/ H2O 20-80 | 18.2 |

TABLE 1-continued
| Ex. No | Structure | Synthetic Method Code — Urea Formation | Final ester Hydrolysis | Methods for Intermediates | ESPMS M−H | ESPMS M+H | NMR 1H, ppm, d6-DMSO | Reverse Phase HPLC (Run Time = 20 min.) Column Type | Solvent + 0.1% TFA | Rt. min. |
|---|---|---|---|---|---|---|---|---|---|---|
| 74 | 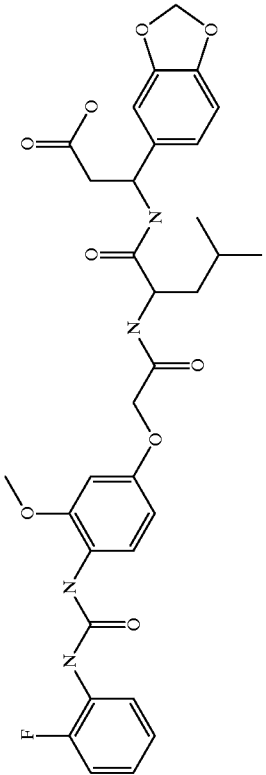 | B | K | Q | | 639.7 | 0.7–0.9(6H, m), 1.3–1.5(3H, m), 2.5–2.7(2H, m), 3.8(3H, s), 4.2–4.4(1H, m), 4.5(2H, s), 4.9–5.1(1H, m), 5.9(2H, s), 6.4–6.5(1H, d), 6.6–7.0(5H, m), 7.0–7.1(1H, t), 7.1–7.2(1H, m), 7.8(1H, d), 7.9(1H, d), 8.1–8.2(1H, t), 8.6(1H, s), 8.8(1H, d), 9.0(1H, s) | Dynamax 60A C18 | MeCN/H2O 20-80 | 17.0 |
| 75 | 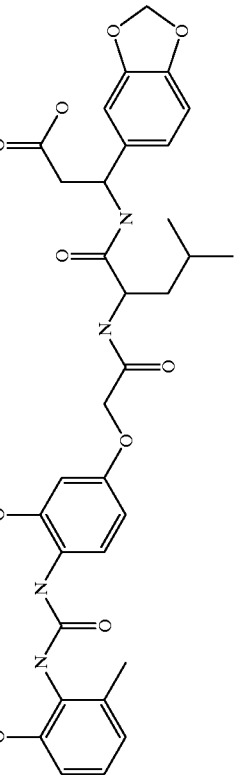 | B | K | Q | | 651.7 | 0.7–0.9(6H, m), 1.3–1.5(3H, m), 2.2(3H, s), 2.5–2.7(2H, m), 3.9(3H, s), 4.2–4.4(1H, m), 4.5(2H, s), 4.9–5.1(1H, m), 6.2(2H, s), 6.5–6.6(1H, d), 6.7–7.0(7H, m), 7.9–8.0(2H, m), 8.0(1H, s), 8.3(1H, s), 8.5–8.6(1H, d) | Dynamax 60A C18 | MeCN/H2O 20-80 | 15.7 |

TABLE 1-continued

| Ex. No | Structure | Synthetic Method Code — Urea Formation | Synthetic Method Code — Final ester Hydrolysis | Synthetic Method Code — Methods for Intermediates | ESPMS M−H | ESPMS M+H | NMR 1H, ppm. d6-DMSO | Reverse Phase HPLC (Run Time = 20 min.) Column Type | Solvent + 0.1% TFA | Rt. min |
|---|---|---|---|---|---|---|---|---|---|---|
| 76 | 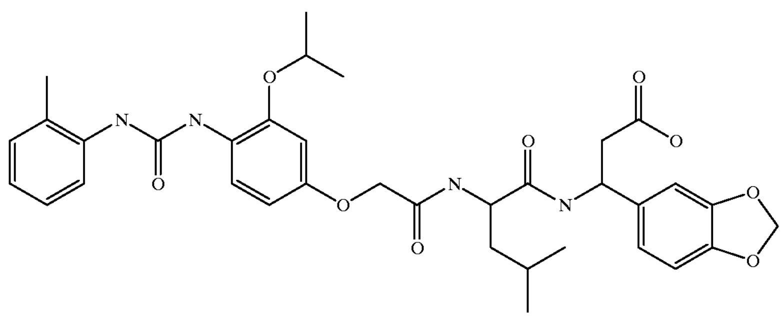 | B | K | Q | | 661.7 | 0.7–0.9(6H, m), 1.2–1.3(6Hm, d), 1.3–1.5(3H, m), 2.2(1H, s), 2.5–2.7(2H, m), 4.2–4.4(1H, m), 4.5(2H, s), 4.5–4.6(1H, m), 4.9–5.1(1H, m), 5.9(2H, s), 6.4–6.5(1H, d), 6.6–7.0(5H, m), 7.1–7.2(2H, m), 7.6(1H, d), 7.8(1H, d), 7.8–7.9(2H, d), 8.0(1H, s), 8.4(1H, s), 8.5(2H, d) | Dynamax 60A C18 | MeCN/ H2O 20–80 | 18.4 |

Method A1 is via the ester of a p-aminophenoxyacetic acid plus isocyanate. (example 1d)
Method A2 is via the ester of a p-aminophenoxyacetic acid plus isocyanate which is generated in solution from a carboxylic acid and diphenyl phosphoryl azide. (example 1d)
Method B is via the ester of the p-aminophenoxyacetic acid with triphosgene then a second amine. (analogous method to that described in example 30c)
Method C1 is via complete N-terminus amine by reaction with triphosgene then a second amine. (example 30c)
Method C2 is via complete N-terminus amine by reaction with an isocyanate (example 69a)
Method K is via hydrolysis of C-terminus methyl ester. (example 1)
Method L is via hydrogenolysis of C-terminus benzyl ester. (example 23)
Method P is the introduction of an amino group via BTEAD into a electron rich phenol. (example 71b)
Method Q is the displacement of an activated arylhalide by a nucleophilic species (example 67a)

What is claimed is:

1. A compound of formula (II)

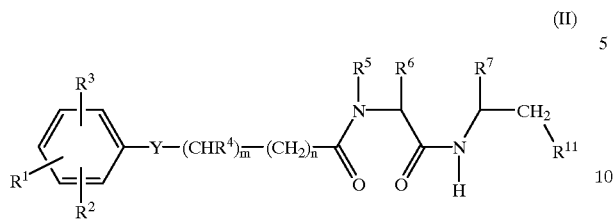

wherein:

$R^1$ is in the para or meta position and is

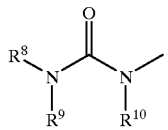

$R^2$ and $R^3$ are each independently selected from hydrogen, nitro, $C_{1-6}$alkyl, $C_{3-6}$cycloalkyl, $C_{2-6}$alkenyl, $C_{2-6}$alkynyl, $C_{1-4}$alkoxy, $C_{1-6}$alkylamino, $C_{1-6}$-dialkylamino, $C_{1-6}$alkyl$C_{1-4}$alkoxyl, $C_{1-6}$alkylamino$C_{1-6}$alkyl, amino, cyano, halogeno, trifluoromethyl, —$CO_2R^{12}$ and —$CONR^{12}R^{13}$, where $R^{12}$ and $R^{13}$ are independently selected from hydrogen or $C_{1-6}$alkyl, or $R^2$ and $R^3$ together with the phenyl to which they are attached form a 9 or 10 membered bicyclic ring system;

$R^4$ is $C_{1-4}$alkyl;

$R^5$ is selected from hydrogen and $C_{1-4}$alkyl;

$R^6$ is selected from $C_{1-6}$ alkyl, $C_{1-4}$alkyl($C_{4-6}$)cycloalkyl, $C_{1-6}$alkyl($C_{1-6}$)alkoxyl, $C_{1-6}$alkylS($C_{1-6}$)alkyl, $C_{1-4}$alkylsulphonyl($C_{1-4}$)alkyl,

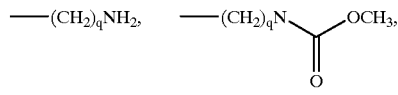

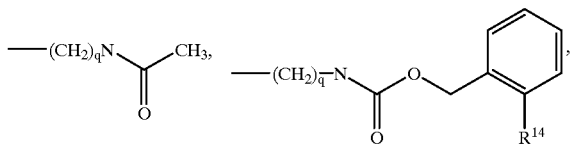

where q is an integer from 1 to 6 and $R^{14}$ is halogeno;

$R^7$ is selected from $C_{1-6}$alkyl, $C_{1-8}$alkoxylcarbonyl, $C_{2-6}$alkenyl, 1,3-benzodioxol-5-yl and aryl each optionally substituted by one or more substituents selected from $C_{1-4}$ alkoxy, $C_{1-6}$alkyl, cyano, halogeno, and trifluoromethyl;

$R^8$ is aryl, heteroaryl, a bicyclic heteroaryl ring system linked to the nitrogen via a ring carbon or a 9 or 10 membered bicyclic ring system linked to the nitrogen via a ring carbon and each ring is optionally substituted with up to two substituents, which may be the same or different, and are selected from $C_{1-6}$alkyl, $C_{1-4}$alkoxy, $C_{1-4}$alkylthio, $C_{1-6}$alkyl$C_{1-4}$alkoxyl, $C_{1-6}$alkylamino$C_{1-6}$alkyl, hydroxy, —$CO_2H$, —$(CH_2)_p$OH where p is 1 or 2, cyano, halogeno, and trifluoromethyl;

$R^9$ and $R^{10}$ are each independently selected from hydrogen and $C_{1-4}$alkyl or $R^8$ and $R^9$ together with the nitrogen to which they are attached form a dihydroindolyl, or a dihydroquinolinyl group;

$R^{11}$ is selected from carboxyl, tetrazolyl, alkyl sulphonylcarbamoyl, sulfo and sulfino;

Y is oxygen, sulphur or sulfonyl;

m is 0 or 1; and n is 0 or an integer from 1 to 4 with the proviso that m and n cannot both be 0, and when m is 1, n is 0;

or a pharmaceutically acceptable salt or in vivo hydrolysable ester thereof.

2. A compound according to claim 1 having the formula

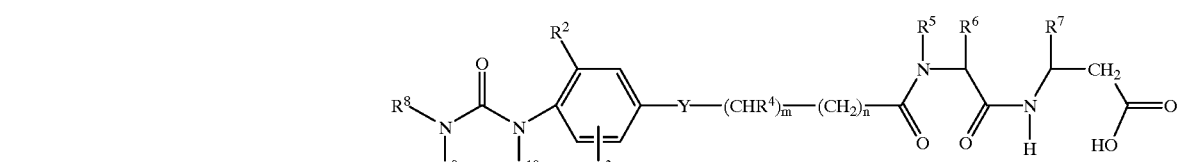

wherein:

$R^2$ is $C_{1-4}$alkoxy;

$R^3$, $R^5$ and $R^{10}$ are each independently hydrogen;

$R^4$ is $C_{1-4}$ alkyl;

$R^6$ is selected from $C_{1-4}$alkyl and $C_{1-4}$alkylS($C_{1-4}$)alkyl;

$R^7$ is selected from $C_{2-6}$ alkenyl and 1,3-benzodioxol-5-yl optionally substituted by at least one substituent selected from $C_{1-4}$ alkoxy, $C_{1-6}$ alkyl, cyano, halogeno, and trifluoromethyl;

$R^8$ is aryl or heteroaryl each optionally substituted with one substituent selected from $C_{1-6}$alkyl, $CH_2OH$, halogeno, and hydroxy; and $R^9$ is hydrogen or $C_{1-4}$alkyl or $R^8$ and $R^9$ together with the nitrogen to which they are attached form a dihydroindolyl or a dihydroquinolinyl group; and m and n are 0 or 1 with the proviso that m and n cannot both be 0 or 1;

or a pharmaceutically acceptable salt or in vivo hydrolysable ester thereof.

3. A compound according to claim 2 wherein $R^2$ is methoxy.

4. A compound selected from 4-(N'-(2-methylphenyl)urea)-3-methoxy phenoxyacetyl (leucine-3-amino-(3,4-methylenedioxy)phenylpropionic acid)amide;

4-(N'-phenylurea)-3-methoxy phenoxyacetyl (leucine-3-amino-(3,4-methylenedioxy)phenylpropionic acid)amide;

4-(N'-(2-chlorophenyl)urea)-3-methoxy phenoxyacetyl (leucine-3-amino-(3,4-methylenedioxy)phenylpropionic acid)amide;

7-(N'-(2-methylphenyl)urea)-2,3-dihydrobenzofuranyl-4-oxyacetyl(leucine-3-amino-(3,4-methylenedioxy) phenylpropionic acid)amide;

4-(N'-(2-hydroxymethylphenyl)urea)-3-methoxy phenoxyacetyl (leucine-3-amino-(3,4-methylenedioxy) phenylpropionic acid)amide;

4-[(2,3-dihydro-1H-indol-1ylcarbonyl)amino]-3-methoxy phenoxyacetyl (leucine-3-amino-(3,4-methylenedioxy) phenylpropionic acid)amide;

4-(N'-(2-fluorophenyl)urea)-3-methoxy phenoxyacetyl (leucine-3-amino-(3,4-methylenedioxy)phenylpropionic acid)amide;

4-(N'-(2-hydroxy-6-methylphenyl)urea)-3-methoxy phenoxyacetyl (leucine-3-amino-(3,4-methylenedioxy) phenylpropionic acid)amide; and 4-(N'-(2-methylphenyl)urea)-3-isopropoxy phenoxyacetyl (leucine-3-amino-(3,4-methylenedioxy)phenylpropionic acid)amide.

5. A compound of formula (IV)

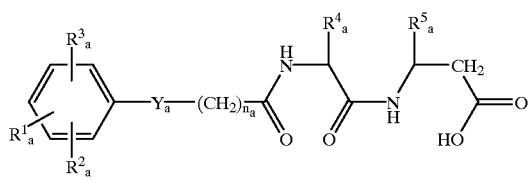

(IV)

wherein:

$R^1_a$ is in the para or meta position and is

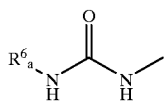

$R^2_a$ and $R^3_a$ are each independently selected from hydrogen, nitro, $C_{1-6}$ alkyl, $C_{3-6}$ cycloalkyl, $C_{2-6}$alkenyl, $C_{2-6}$alkynyl, $C_{1-4}$ alkoxy, $C_{1-6}$ alkylamino, $C_{1-4}$alkoxyl$C_{1-6}$alkyl, $C_{1-6}$alkylamino$C_{1-6}$alkyl, cyano, halogeno, trifluoromethyl, $-CO_2R^7_a$ and $-CON R^7_a R^8_a$ where $R^7_a$ and $R^8_a$ are independently selected from hydrogen or $C_{1-6}$ alkyl;

$R^4_a$ is selected from $C_{1-6}$ alkyl, $C_{1-6}$alkoxy-substituted $(C_{1-6})$alkyl, and $C_{1-6}$alkylS$(C_{1-6})$alkyl;

$R^5_a$ is selected from $C_{1-6}$alkyl, $C_{2-6}$ alkenyl, 1,3-benzodioxol-5-yl and aryl optionally substituted by at least one substituent selected from $C_{1-4}$ alkoxy, $C_{1-6}$ alkyl, cyano, halogeno, and trifluoromethyl;

$R^6_a$ is aryl or heteroaryl and the ring is optionally substituted with up to two substituents, which may be same or different, selected from $C_{1-6}$ alkyl, $C_{1-4}$ alkoxy, $C_{1-4}$alkoxy, $C_{1-4}$alkyl, $C_{1-6}$alkylamino$C_{1-6}$alkyl, cyano, halogeno, and trifluoromethyl;

$Y_a$ is oxygen or sulphur; and $n_a$ is an integer from 1 to 4;

or a pharmaceutically acceptable salt or in vivo hydrolysable ester thereof.

6. A pharmaceutical composition comprising a compound according to any one of claims 1 to 5, or a pharmaceutically acceptable salt thereof in association with a pharmaceutically acceptable diluent or carrier.

7. A process for preparing a compound of formula (II) or a pharmaceutically acceptable salt or an in vivo hydrolysable ester thereof which process comprises coupling together i) a compound of formula (V)

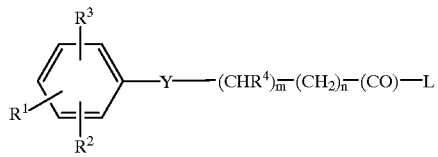

(V)

and a compound of formula (VI)

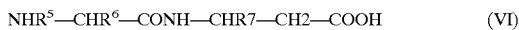

(VI)

or ii) a compound of formula (VII)

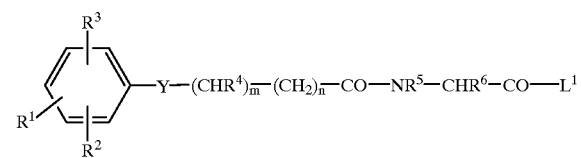

(VII)

and a compound of formula (VIII)

(VIII)

wherein L and $L^1$ are leaving groups and any functional group is optionally protected; and thereafter, if necessary:

a) removing any protecting group; and b) forming a pharmaceutically acceptable salt or in-vivo hydrolysable ester.

8. A method for inhibiting the interaction between VCAM-1 and/or fibronectin and the integrin receptor VLA-4 in mammals in need of such treatment which comprises administering to said warm-blooded mammals an effective amount of a compound according to any one of claims 1 to 5, or a pharmaceutically acceptable salt thereof.

9. A method according to claim 8 for treating multiple sclerosis, rheumatoid arthritis, asthma, coronary artery disease or psoriasis.

* * * * *